United States Patent
First et al.

(10) Patent No.: US 9,777,309 B2
(45) Date of Patent: Oct. 3, 2017

(54) HIGH THROUGHPUT ASSAY FOR MONITORING AMP PRODUCTION AND AMINOACYL-TRNA SYNTHETASE ACTIVITY

(71) Applicant: Board of Supervisors of Louisiana State University and Agricultural and Mechanical College, Baton Rouge, LA (US)

(72) Inventors: Eric A First, Shreveport, LA (US); Charles J Richardson, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 205 days.

(21) Appl. No.: 14/876,349

(22) Filed: Oct. 6, 2015

(65) Prior Publication Data

US 2016/0097075 A1    Apr. 7, 2016

Related U.S. Application Data

(60) Provisional application No. 62/060,059, filed on Oct. 6, 2014, provisional application No. 62/060,037, filed on Oct. 6, 2014.

(51) Int. Cl.
| | | |
|---|---|---|
| *C12Q 1/66* | (2006.01) | |
| *C40B 50/06* | (2006.01) | |
| *C07H 19/10* | (2006.01) | |
| *C12N 9/00* | (2006.01) | |
| *C12Q 1/25* | (2006.01) | |

(52) U.S. Cl.
CPC ....... *C12Q 1/25* (2013.01); *G01N 2333/9015* (2013.01)

(58) Field of Classification Search
CPC . C12N 9/00; C12N 9/93; C07H 19/10; C12Q 1/25; C12Q 1/66; C40B 50/06; G01N 2500/04
See application file for complete search history.

(56) References Cited

PUBLICATIONS

Matt Seaben et al. Development and Validation of a Transcreener Assay for Detection of AMP- and GMP-Producing Enzymes. Assay Drug Dev Technol. Jun. 2010; 8(3): 344-355.*
Matt Staeben et al. Development and Validation of a Transcreener Assay for Detection of AMP—and GMP—Producing Enzymes. Assay Drug Dev Technol. 2010 Jun; 8(3): 344-355.*
Golden et al. The determination of reduced nicotinamide-adenine dinucleotide and metabolic intermediates in picomole amounts with bacterial luciferase. Biochem J. Jun. 15, 1980; 188(3.*

* cited by examiner

*Primary Examiner* — Kagnew H Gebreyesus
(74) *Attorney, Agent, or Firm* — Davis & Bujold, P.L.L.C.; Charles Holoubek

(57) ABSTRACT

A method of conducting an enzymatic reaction assay involving adenosine 5'-monophosphate (AMP) comprising the steps of reacting one or more compounds and producing AMP, deaminating the AMP to produce IMP, and oxidating the IMP by NAD+ to produce XMP and NADH.

18 Claims, 50 Drawing Sheets

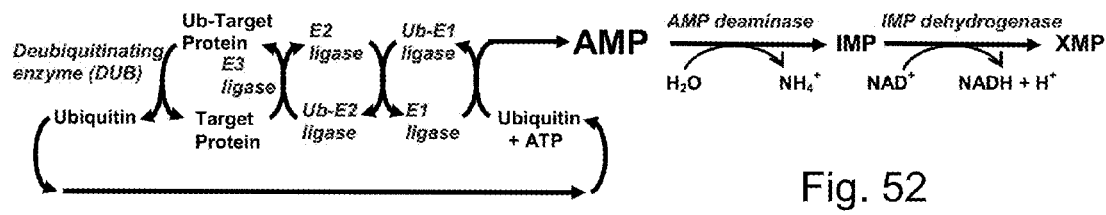
Fig. 52
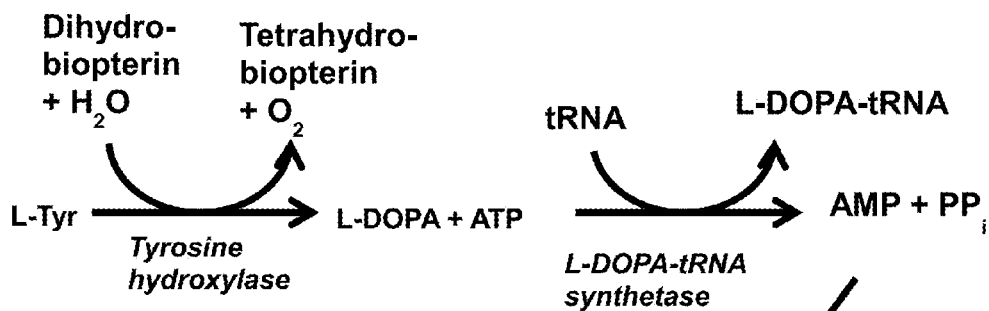
Fig. 53
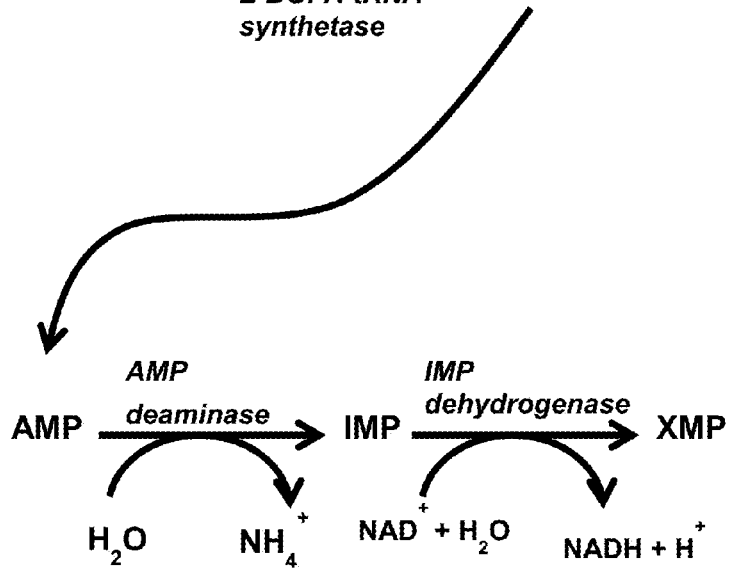

HIGH THROUGHPUT ASSAY FOR MONITORING AMP PRODUCTION AND AMINOACYL-TRNA SYNTHETASE ACTIVITY

CROSS REFERENCE TO RELATED APPLICATIONS

This application claims priority to United States Provisional Patent Application No. 62/060,059, filed Oct. 6, 2014, the contents of which is incorporated herein by reference in its entirety, and claims priority to U.S. Provisional Patent Application No. 62/060,037, filed Oct. 6, 2014, claims priority to the contents of which is incorporated herein by reference in its entirety.

STATEMENT REGARDING FEDERALLY SPONSORED RESEARCH OR DEVELOPMENT

Not applicable.

FIELD OF THE INVENTION

This invention relates generally to enzymatic assays, including continuous spectrophotometric assays for monitoring AMP production and high throughput assays for monitoring aminoacyl-tRNA synthetase activity.

BACKGROUND OF THE INVENTION

High-throughput screening assays are a staple of drug discovery, allowing over 100,000 compounds to be screened per day. Targets of high-throughput screens include G-protein coupled receptors, enzymes, hormones, ion channels, nuclear receptors, and DNA transcription factors. In addition to identifying lead compounds ("hits"), drug development requires high-throughput assays to eliminate false positives, validate the target, prioritize the hits, and elucidate structure-activity relationships. The development of high-throughput assays is also required to keep pace with the rapid growth of genomic and proteomic data.

Enzymes that release AMP as a product play a role in a number of diseases. For example, cAMP phosphodiesterases (PDEs) convert cAMP to AMP and, as a result, regulate signal transduction pathways governing vascular resistance, cardiac output, visceral motility, immune response, inflammation, neuroplasticity, vision, and reproduction. PDE inhibitors prolong or enhance cAMP-mediated signaling pathways and have been used in the treatment of pulmonary arterial hypertension, coronary heart disease, dementia, depression, schizophrenia, and other disorders. Other enzymes that release AMP as a product include the ubiquitin ligase and ubiquitin-like ligase proteins, which catalyze the attachment of ubiquitin and ubiquitin-like proteins (e.g. small ubiquitin-like modifier (SUMO) proteins) to their protein substrates, modifying their function or targeting them for degradation by the proteasome. Like proteasome inhibitors, inhibitors of ubiquitin ligases have potential therapeutic value in treating cancer and other diseases by inducing apoptosis. However, since ubiquitin ligases target specific subsets of proteins for degradation, they are more selective than proteasome inhibitors. Enzymes that remove these protein modifications (e.g. deubiquitinating enzymes) also target selected subsets of proteins, providing additional candidates for therapeutic intervention. Lastly, members of the aminoacyl-tRNA synthetase family release AMP as a product during the aminoacylation of tRNA, a crucial step in protein synthesis. Members of this family are potential targets for the development of novel antibiotics and antifungals. For example, an isoleucyl-tRNA synthetase inhibitor, mupirocin, is used to treat multidrug resistant *Staphylococcus aureus*, while a leucyl-tRNA synthetase inhibitor, Kerydin™, is an antifungal that recently received FDA approval for the topical treatment of onychomycos of the toenails. Furthermore, the essential role that aminoacyl-tRNA synthetases play in protein synthesis makes the human homologs potential targets for chemotherapy agents.

Currently, assays are available to monitor the production of AMP or pyrophosphate, but they either require quenching a reaction to check the AMP/pyrophosphate production a given point in time, and/or they are limited in that they can only be applied to enzymes that form AMP through hydrolysis of ATP. As a result, they cannot be used to follow the activities of enzymes such as phosphodiesterases and ribonucleases, which do not release pyrophosphate as a product. In addition, since the production of inorganic phosphate is being monitored in such assays, they are incompatible with phosphate buffers.

Further, the rise in drug resistant organisms represents a significant world health threat. In the United States, approximately 1.7 million patients acquired an infection while in the hospital, resulting in nearly 100,000 fatalities. Seventy percent of these infections result from antibiotic-resistant bacteria. In addition to increased mortality rates, the rise in antimicrobial resistant organisms increases treatment time and length of stay for hospital patients, hampers medical advancements—including organ transplants, cancer treatment, and surgery—and increases health care costs. Antibiotic resistance adds ~$20 billion/year to health care costs and results in 8 million additional days that patients spend in the hospital.

Aminoacyl-tRNA synthetases (aaRSes) are essential enzymes, which catalyze the attachment of amino acids to their cognate tRNAs. Several properties of the aminoacyl-tRNA synthetases make them attractive candidates for antimicrobial drugs, including: (1) conservation of the catalytic mechanism across bacterial species, (2) loss of biological fitness in bacteria that are resistant to aminoacyl-tRNA synthetase inhibitors, (3) differences in the catalytic mechanism of bacterial and eukaryotic aminoacyl-tRNA synthetase homologs, and (4) the existence of x-ray crystal structures for all 20 aminoacyl-tRNA synthetases, providing a structural framework for designing inhibitors and elucidating their mechanism of action. Known aminoacyl-tRNA synthetase inhibitors include natural products, such as mupirocin and furanomycin (isoleucyl-tRNA synthetase), borrelidin (threonyl-tRNA synthetase), granaticin (leucyl-tRNA synthetase), indolmycin (tryptophanyl-tRNA synthetase), ochratoxin A (phenylalanyl-tRNA synthetase), and cispentacin (prolyl-tRNA synthetase). In addition, a number of pharmaceutical companies have shown interest in aminoacyl-tRNA synthetase inhibitors as potential therapeutics. For example, the leucyl-tRNA synthetase inhibitor, Keryidin™ (Anacor™ Pharmaceuticals, Palo Alto, Calif.), recently received FDA approval for treatment of onychomycosis (toenail fungus), while methionyl-tRNA synthetase inhibitors developed by GlaxoSmithKline™ have been found to inhibit *Trypanosoma brucei* infection in mice. Borrelidin, which initially was found to inhibit bacterial threonyl-tRNA synthetases, is currently being tested as a treatment for malaria, suggesting that inhibitors of bacterial aminoacyl-tRNA synthetases may also be useful in treating protozoan parasites. Similarly, cladosporin, which was originally identified as an antibacterial agent, has been shown to inhibit lysyl-tRNA synthetase from the malaria parasite, *Plasmodium falciparum*. Both the chemical diversity displayed by known aminoacyl-tRNA synthetase inhibitors, and the diversity of their targets, supports the principle that aminoacyl-tRNA synthetases are rich targets for developing novel antimicrobials.

While assays have been developed for monitoring the activity of aminoacyl-tRNA synthetases, a common limitation is their inability to recycle the tRNA substrate. As tRNA is the limiting substrate in these assays, the ability to regenerate it in situ would both increases the sensitivity of the assays, while decreasing the cost of the current technology.

SUMMARY OF THE INVENTION

Wherefore, it is an object of the present invention to overcome the above mentioned shortcomings and drawbacks associated with the prior art.

With this in mind, we have developed a homogenous, continuous, spectrophotometric assay for monitoring the production of AMP. A number of enzymes release AMP as a product, including aminoacyl-tRNA synthetases, cAMP phosphodiesterases, ubiquitin and ubiquitin-like ligases, DNA ligases, CoA ligases, polyA deadenylases, and ribonucleases. Many of these enzymes are either current or potential drug targets for a wide range of diseases and disorders. The assay described in this paper consists of two steps: (1) deamination of AMP to produce IMP and (2) the oxidation of IMP by NAD+, producing XMP and NADH (FIG. 1). These reactions are catalyzed by AMP deaminase and IMP dehydrogenase, respectively. Since the production of NADH is accompanied by an increase in absorbance at 340 nm, the release of AMP can be monitored continuously, allowing it to be used for both high-throughput screening and the subsequent kinetic analysis of lead compounds. In this paper, we validate the use of this assay for monitoring the production of AMP.

The AMP production monitoring assay described here couples the deamination of AMP to the reduction of $NAD^+$. This allows the production of AMP to be monitored by measuring the change in absorbance at 340 nm. This is the first time that the activity of AMP deaminase has been coupled to that of IMP dehydrogenase and the first time that NADH has been used as a read out for the production of AMP. The AMP production monitoring assay continuously monitors the production of AMP, allowing it to be used for both high-throughput drug screening and kinetic analyses. This has several advantages. First, the production of AMP is monitored in real time, simplifying the screening process. Second, as the assay can be used to monitor the time course of the reaction, both the binding affinity and mode of inhibition can be rapidly determined for any lead compound identified in the screen. Third, the AMP production monitoring assay described here is relatively inexpensive, requiring only readily available laboratory reagents and the production of two recombinant proteins. The simplicity of the AMP production monitoring assay makes it equally amenable for use in the research laboratory, high-throughput screening facilities, and high school and undergraduate classrooms. Lastly, while the AMP production monitoring assay described here can be used to accurately monitor AMP levels down to at least 5 µM, its sensitivity can be further increased by coupling the production of NADH to the bacterial luciferase catalyzed oxidation of low molecular weight aldehydes, as described in S. E. Brolin, E. Borglund, L. Tegner, G. Wettermark, "Photokinetic micro assay based on dehydrogenase reactions and bacterial luciferase," *Analytical Biochemistry*, 42 (1971) 124-135; S. Golden, J. Katz, "The determination of reduced nicotinamide-adenine dinucleotide and metabolic intermediates in picomole amounts with bacterial luciferase," *The Biochemical Journal*, 188 (1980) 799-805; P. E. Stanley, "Determination of subpicomole levels of NADH and FMN using bacterial luciferase and the liquid scintillation spectrometer," *Analytical Biochemistry*, 39 (1971) 441-453; such methods incorporated herein by reference. Alternatively, the sensitivity of the assay can be increased by coupling it to the oxidation of NADH by resazurin, producing the red fluorescent resorufin product ($\epsilon_{572}^{resorufin}$=73,000 $M^{-1}$ $cm^{-1}$, $\lambda_{em}$=585 nm, quantum yield=0.74), as described in S. Barnes, J. G. Spenney, "Stoichiometry of the NADH-oxidoreductase reaction for dehydrogenase determinations," *Clin Chim Acta*, 107 (1980) 149-154, such methods incorporated herein by reference.

In addition to monitoring enzymes that release AMP as their product, the AMP production monitoring assay can also be used to monitor enzymes that can be coupled to the production of AMP via phosphodiesterases, ubiquitin and ubiquitin-like ligases, CoA ligases, aminoacyl-tRNA synthetases, or any other enzyme that releases AMP as a product. For example, ubiquitin and ubiquitin-like E2 and E3 ligases, as well as deubiquitinating enzymes, can be coupled to the AMP assay through the E1 ligase, which releases AMP. The activity of adenylyl cyclases can be monitored by coupling the formation of cAMP by adenylyl cyclase to the hydrolysis of cAMP by phosphodiesterase. Lastly, the reversible acetylation of histones, p53, and other proteins, which plays an essential role in gene regulation and protein function, can be monitored by coupling the protein acetylation and deacetylation reactions to acetyl-CoA synthetase, which releases AMP during the formation of acetyl-CoA. By coupling these pathways to the AMP production monitoring assay, one can perform high-throughput kinetic analyses on each enzyme in the pathway. Specific steps in each pathway can be targeted by adjusting the enzyme concentrations such that the rate of the assay is dependent on the enzyme that catalyzes the targeted step. Alternatively, inhibitor screens can be designed to target all of the enzymes in the pathway simultaneously, by adjusting the reaction conditions so that each step occurs at approximately the same rate.

As a further embodiment of the AMP production monitoring assay, the AMP production monitoring assay was adapted to monitor the aminoacylation of $tRNA^{Tyr}$ by tyrosyl-tRNA synthetase. As is the case with other aminoacyl-tRNA synthetase assays of current technology, the inventors initially found that the sensitivity of this assay is limited by the amount of tRNA substrate present in the reaction. A novel way to overcome this problem was to cleave the aminoacyl-tRNA product, thereby regenerating the free tRNA substrate. To test this approach, the inventors included cyclodityrosine synthase in the tyrosyl-tRNA synthetase assay. Cyclodityrosine synthase catalyzes the formation of cyclodityrosine from two molecules of tyrosyl-$tRNA^{Tyr}$, releasing $tRNA^{Tyr}$ as a product. The inventors disclose that by including cyclodityrosine in the assay, the free $tRNA^{Tyr}$ can be regenerated, substantially increasing the sensitivity of the assay. The inventors further disclose that cyclodityrosine accepts L-Tyr-tRNA as a substrate but not D-Tyr-tRNA. Next, the inventors further disclose that the tyrosyl-tRNA synthetase assay can be used to monitor the aminoacylation of tRNA by D-tyrosine if cyclodityrosine synthase is replaced with D-tyrosyl-tRNA deacylase, an enzyme that hydrolyzes D-aminoacyl-tRNAs. The inventors further disclose that the tyrosyl-tRNA synthetase assay can be used to monitor either cyclodityrosine synthase or D-tyrosyl-tRNA deacylase activity by adjusting the enzyme concentrations such that cleavage of Tyr-tRNA is the rate-limiting step. Lastly, the inventors disclose extending the tyrosyl-tRNA synthetase assay to monitor the aminoacylation and post-transfer editing activities in other aminoacyl-tRNA synthetases.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 3 shows time course assays for IMP dehydrogenase at various concentrations of IMP. The assay mix contained 50 mM TRIS, pH 7.2, 100 mM KCl, 0.1 mM dithiothreitol, 5 mM NAD⁺, IMP dehydrogenase (0.76 μM), and varying concentrations of IMP. FIG. 4 shows a plot of reaction rate vs. IMP concentration for IMP dehydrogenase is shown (reaction rates were determined from a linear fit of time course assays in FIG. 3). Data are fit to the Michaelis-Menten equation (equation 1) to calculate $K_m$ and $V_{max}$ values, and to equation 2 to calculate the $k_{cat}$ value. FIG. 5 shows time course assays for IMP dehydrogenase at various concentrations of NAD⁺ are shown. The assay mix contained 50 mM TRIS, pH 7.2, 100 mM KCl, 0.1 mM dithiothreitol, 5 mM IMP, IMP dehydrogenase (0.76 μM), and varying concentrations of NAD⁺. FIG. 6 shows a plot of reaction rate vs. NAD⁺ concentration for IMP dehydrogenase is shown (reaction rates were determined from a linear fit of time course assays shown in FIG. 5). Data in FIGS. 4 and 6 are fit to equations 1, as described below.

FIG. 7 shows time course assays for AMP deaminase at various concentrations of AMP. The assay mix contained 50 mM TRIS, pH 7.2, 100 mM KCl, 2 mM MgATP, 8 mM MgCl₂, 0.1 mM dithiothreitol, 5 mM NAD⁺, IMP dehydrogenase (3 μM), AMP deaminase (0.24 μM), and varying concentrations of AMP. In FIG. 8, a plot of reaction rate vs. AMP concentration for the AMP deaminase is shown (reaction rates were determined from a linear fit of time course assays). Data are fit to equations 1, as described in FIGS. 3-6.

FIG. 15 was used to determine the region of linearity tyrosyl-tRNA synthetase concentration. In these assays, the production of 1 μM of AMP corresponds to an $A_{340}$ reading of 0.0035. Due to mixing and temperature equilibration, the initial time point (t=0) was obtained approximately 1 minute after initiation of the reaction by the addition of tRNA. As a result, the assays shown in FIG. 13 are either near completion (5 μM tRNA) or ~50% complete (15 μM tRNA) prior to recording of the initial time point.

FIG. 16 shows time course assays for tyrosyl-tRNA synthetase at various concentrations of L-tyrosine. FIG. 17 shows a plot of reaction rate vs. L-tyrosine concentration is shown (reaction rates were determined from linear fits of the time course assays shown in FIG. 16). FIG. 18 shows time course assays for tyrosyl-tRNA synthetase at various concentrations of tRNA$^{Tyr}$. FIG. 19 shows a plot of reaction rate vs. tRNA$^{Tyr}$ concentration is shown (reaction rates were determined from linear fits of time course assays shown in FIG. 18). For clarity, only selected substrate concentrations are shown in FIGS. 16 and 18. The data in FIGS. 17 and 19 are fit to equation 1.

FIG. 22 shows time course assays for tyrosyl-tRNA synthetase at various concentrations of D-tyrosine. FIG. 23 shows a plot of reaction rate vs. D-tyrosine concentration for tyrosyl-tRNA synthetase is shown (reaction rates were determined from linear fits of the time course assays shown in FIG. 22). FIG. 24 shows time course assays for tyrosyl-tRNA synthetase at various concentrations of tRNA$^{Tyr}$. FIG. 25 shows a plot of reaction rate vs. tRNA$^{Tyr}$ concentration for tyrosyl-tRNA synthetase is shown (reaction rates were determined from linear fits of the time course assays shown in FIG. 24). For clarity, only selected substrate concentrations are shown in FIGS. 22 and 24. The data in FIGS. 23 and 25 are fit to equation 1.

FIG. 26 shows time course assays for cyclodityrosine synthase at various concentrations of tRNA$^{Tyr}$. FIG. 27 shows a plot of reaction rate vs. tRNA$^{Tyr}$ concentration is shown for cyclodityrosine synthase (reaction rates were determined from linear fits of the time course assays shown in FIG. 26). FIG. 28 shows time course assays for D-tyrosyl-tRNA deacylase at various concentrations of tRNA$^{Tyr}$. FIG. 29 shows a plot of reaction rate vs. tRNA$^{Tyr}$ concentration is shown for D-tyrosyl-tRNA deacylase (reaction rates were determined from linear fits of the time course assays shown in FIG. 28). For clarity, only selected concentrations of tRNA$^{Tyr}$ are shown in FIGS. 26 and 28. The data in FIGS. 27 and 29 are fit to equation 1.

FIG. 36 shows initial rate vs. substrate curve for L-tyrosine. The assay contained 10 mM MgATP, 5 μM tRNA$^{Tyr}$, 50 nM *G. stearothermophilus* tyrosyl-tRNA synthetase, and 8.6 μM *Mycobacterium tuberculosis* cyclodityrosine synthetase. FIG. 37 show initial rate vs. substrate curve for tRNA$^{Tyr}$. The assay contained 10 mM MgATP, 1 mM L-tyrosine, and 200 nM *G. stearothermophilus* tyrosyl-tRNA synthetase. Data were fit to the Michaelis-Menten equation, where M0=substrate concentration, m1=V$_{max}$, and m2=K$_m$.

FIG. 40 shows the reaction scheme for monitoring aminoacylation of tRNA by D-tyrosine. FIG. 41 shows the effect that varying the D-tyrosine concentration has on the rate of the tyrosyl-tRNA synthetase catalyzed tRNA aminoacylation reaction is shown. The assay contains 10 mM MgATP, 2 μM tRNA$^{Tyr}$, 50 nM *G. stearothermophilus* tyrosyl-tRNA synthetase, and 50 μM *T. thermophilus* D-tyrosyl-tRNA deacylase. FIG. 42 shows the effect that varying the tRNA$^{Tyr}$ concentration has on the rate of the tyrosyl-tRNA synthetase catalyzed tRNA aminoacylation reaction is shown. The assay contains 10 mM MgATP, 600 mM D-tyrosine, 50 nM *G. stearothermophilus* tyrosyl-tRNA synthetase, and 50 μM *T. thermophilus* D-tyrosyl-tRNA deacylase. In both assays, the concentration of D-tyrosyl-tRNA deacylase present was 50 μM. Data were fit to the Michaelis-Menten equation to determine K$_m$ and V$_{max}$ values, where M0 is the substrate concentration, m1 is the V$_{max}$, and m2 is the K$_m$.

FIG. 52 is a reaction scheme for monitoring the activity of ubiquitin ligases by recycling the ubiquitin substrate. Deubiquitinating enzymes (DUBs) remove ubiquitin from ubiquinated proteins, allowing it to be recycled. By including DUBs in the assay, ubiquitin is recycled and does not need to be continuously supplied, substantially increasing the sensitivity and decreasing the cost of the assay.

FIG. 53 is a reaction scheme for monitoring the activity of tyrosine hydroxylase by coupling it to the production of NADH via the AMP assay. L-DOPA-tRNA synthetase is an engineered version of tyrosyl-tRNA synthetse that aminoacylates tRNA$^{Tyr}$ with L-DOPA. An analogous reaction scheme can be drawn in which the activity of tyrosine hydroxylase is coupled the production of light by bacterial luciferase (e.g., by coupling the production of NADH to the bacterial luciferase catalyzed oxidation of a low molecular weight aldehyde, as described above).

DETAILED DESCRIPTION OF THE INVENTION

The present invention will be understood by reference to the following detailed description, which should be read in conjunction with the appended drawings. It is to be appreciated that the following detailed description of various embodiments is by way of example only and is not meant to limit, in any way, the scope of the present invention.

Figure 1:
FIG. 1 is a reaction scheme coupling AMP to the production of NADH. AMP deaminase and IMP dehydrogenase are used to couple the production of AMP to the reduction of NAD⁺. AMP production is monitored by following the increase in absorbance at 340 nm that occurs as a result of the reduction of NAD⁺ to NADH ($\epsilon_{340}$=6220 M⁻¹ cm⁻¹). AMP, IMP, and XMP represent adenosine 5'-monophosphate, inosine 5'-monophosphate, and xanthine 5'-monophosphate, respectively.

Turning now to FIG. 1, a brief description concerning the various components of the present invention will now be briefly discussed.

Materials and Methods: AMP production monitoring assay. Materials were obtained from the following sources: *Saccharomyces cerevisiae* clones containing the open reading frames for AMP deaminase and IMP dehydrogenase (Open Biosystems/GE Healthcare Life Sciences, Lafayette, Colo.), TOPO® TA Cloning® Kit (Life Technologies, Grand Island, N.Y.), Wizard® SV Gel and PCR Clean-Up System (Promega, Madison, Wis.), pET30a(+) expression vector and Rosetta™ 2 DE3 *Escherichia coli* cells (EMD Biosciences, Billerica, Miss.), XL2 Blue™ *Escherichia coli* cells (Agilent Technologies, Santa Clara, Calif.), E.Z.N.A.® Plasmid DNA Mini I Kit (Omega Bio-Tek, Norcross, Ga.), T4 DNA ligase, NcoI-HF®, and XhoI (New England Biolabs, Ipswich, Mass.), Taq DNA polymerase (G-Biosciences, St. Louis, Mo.), AMP (Research Products International Corporation, Mount Prospect, Ill.), ATP, IMP, and NAD+, (VWR International, Radnor, Pa.), and oligonucleotides (Integrated DNA Technologies, Coralville, Iowa). All other reagents were obtained from ThermoFisher Scientific (Waltham, Mass.). DNA sequencing was performed by the DNA Lab at Arizona State University (Tempe, Ariz.). Curve fitting and graphing was performed using Grafit™ (Erithacus Software Ltd., Horley, Surrey, UK) and Kaleidograph® (Synergy Software, Reading, Pa.).

Subcloning AMP deaminase and IMP dehydrogenase into the pET30a(+) expression vector—The polymerase chain reaction (PCR) was used to amplify the open reading frames for *Saccharomyces cerevisiae* AMP deaminase and IMP dehydrogenase (Open Biosystems clones YML035C and YLR432W, respectively). Primers were designed such that the amplified DNA contained unique NcoI and XhoI sites at the 5' and 3' ends, respectively. Amplified open reading frames were initially ligated into the PCR2.1-TOPO TA vector and transformed into XL2 Blue cells. Individual colonies were selected and grown overnight in 2 ml of 2×YT media (16 g/L Tryptone, 10 g/L yeast extract, 5 g/L NaCl) followed by PCR screening to identify positive clones. Plasmids were isolated from the positive cultures using an E.Z.N.A. Plasmid DNA Mini I kit and the inserted DNA was sequenced by the Arizona State University DNA Sequencing Facility. The open reading frames were subsequently removed by digestion with NcoI-HF and XhoI, gel purified using the Wizard SV Gel and PCR Clean-Up System, and subcloned into the pET30a(+) vector such that subsequent expression results in a protein containing an amino-terminal S-Tag/His-Tag followed by either AMP deaminase or IMP dehydrogenase. The AMP deaminase and IMP dehydrogenase coding sequences in the pET30a(+) vector were sequenced in their entirety. These plasmids are designated pADA1-WT and pIDH1-WT, respectively. All procedures involving recombinant DNA were performed using NIH biosafety level 1 containment procedures, and were approved by the LSU Health Sciences Center Biosafety Committee.

Protein expression and purification—AMP deaminase and IMP dehydrogenase were expressed in *E. coli* Rosetta 2 DE3 cells harboring the pADA1-WT and pIDH1-WT plasmids, respectively. Purification of the recombinant proteins was carried out by NiNTA affinity chromatography using a procedure analogous to that described previously for the purification of human tyrosyl-tRNA synthetase, such as, for example, in Xu, Y., Zhang, H. T., and O'Donnell, J. M. (2011) "Phosphodiesterases in the central nervous system: implications in mood and cognitive disorders," Handbook of experimental pharmacology, 447-485, and Esposito, K., Reierson, G. W., Luo, H. R., Wu, G. S., Licinio, J., and Wong, M. L. (2009) "Phosphodiesterase genes and antidepressant treatment response: a review," Annals of medicine 41, 177-185, such procedures incorporated herein. Proteins were purified to >95% homogeneity, based on SDS-polyacrylamide gel electrophoresis. Protein concentrations were calculated based on $A_{280}$ measurements ($\epsilon_{280}$=470,320 and 99,480 $M^{-1}$ $cm^{-1}$ for the AMP deaminase and IMP dehydrogenase homotetramers, respectively, as determined by the ExPASy® ProtParam tool). Purified proteins were stored at −70° C. in buffer containing 50 mM Tris, pH 7.5, 20 mM β mercaptoethanol, 10 mM $MgCl_2$, and 10% glycerol (v/v).

Kinetic analyses—IMP dehydrogenase was assayed in buffer containing 50 mM TRIS, pH 7.2, 100 mM KCl, 0.1 mM dithiothreitol and either 5 mM IMP or 5 mM $NAD^+$ (for determination of $K_m^{NAD+}$ and $K_m^{IMP}$, respectively). To determine the $K_m^{NAD+}$ and $K_m^{IMP}$ values, the concentrations of $NAD^+$ and IMP were varied from 0-5 mM, respectively, and the conversion of $NAD^+$ to NADH was monitored at 340 nm ($\epsilon_{340}$=6220 $M^{-1}$ $cm^{-1}$). AMP deaminase was assayed in buffer containing 50 mM TRIS, pH 7.2, 100 mM KCl, 2 mM ATP, 8 mM $MgCl_2$, 0.1 mM dithiothreitol, 5 mM $NAD^+$, and 3 μM IMP dehydrogenase. To determine $K_m^{AMP}$, the concentration of AMP was varied from 0-5 mM and the conversion of $NAD^+$ to NADH was monitored as described above. The pH of all stock solutions (e.g. IMP, $NAD^+$, ATP, and AMP) was adjusted to 7.0 prior to use. All kinetic assays were performed in 96 well microtiter plates at 25° C. using 200 μl of assay mix per well. Under these conditions, the path length is 0.56 cm. All assays were monitored by following the change in absorbance at 340 nm over 10 minutes using a Synergy 4 Hybrid Microplate Reader (BioTek, Winooski, Vt.).

The pH profile for IMP dehydrogenase was determined by assaying the enzyme in the presence of 100 mM KCl, 0.1 mM dithiothreitol, 5 mM IMP, 5 mM $NAD^+$, and 50 mM of either sodium phosphate (pH 5.5-7.5) or TRIS (pH 7.5-9.0).

The pH profile for AMP deaminase was determined by assaying the enzyme in the presence of 100 mM KCl, 0.1 mM dithiothreitol, 5 mM AMP, 2 mM ATP, 8 mM $MgCl_2$, 1.5 µM IMP dehydrogenase, and 50 mM of either sodium phosphate (pH 5.5-7.5) or TRIS (pH 7.5-9.0).

Initial rates for each substrate concentration were determined from a linear fit of the data ($A_{340}$ vs. time). $K_m$ and $V_{max}$ values were determined by fitting a plot of initial rate vs. substrate concentration to the Michaelis-Menten equation:

$$v_o = \frac{V_{max}[S]}{K_m + [S]} \quad (1)$$

where $v_o$ is the initial rate of the reaction, [E] is the total enzyme concentration, and [S] is the substrate concentration. $k_{cat}$ values were calculated from the equation:

$$V_{max} = k_{cat}[E] \quad (2)$$

where [E] is the molar concentration of the enzyme in the assay.

Results: AMP production monitoring assay. Determination of $K_m$ and $k_{cat}$ values for IMP dehydrogenase. IMP dehydrogenase catalyzes the first committed step in guanine biosynthesis, the oxidation of inosine monophosphate (IMP) by $NAD^+$, as shown in FIG. 1. This reaction can be monitored by the increase in absorbance at 340 nm resulting from the production of NADH. Since the oxidation of IMP will be coupled to the AMP deaminase catalyzed conversion of AMP to IMP, kinetic parameters for the reaction were determined at pH 7.2. As shown in FIGS. 3-6, IMP dehydrogenase from *Saccharomyces cerevisiae* follows classical Michaelis-Menten kinetics with respect to both the IMP and $NAD^+$ substrates. Although the steady state kinetic parameters for *S. cerevisiae* IMP dehydrogenase have not been published previously, comparison with the $k_{cat}$ and $K_m$ values for *Candida albicans* IMP dehydrogenase indicates that the $k_{cat}$ value is similar for the two IMP dehydrogenase homologs. In contrast, *S. cerevisiae* IMP dehydrogenase binds IMP with a 7-fold lower affinity and $NAD^+$ with a 4-fold higher affinity than the *C. albicans* homolog. See Table 1 below.

TABLE 1

| Enzyme | Substrate | $K_m$[1] | $k_{cat}$[1,2] |
|---|---|---|---|
| IMP dehydrogenase | IMP | 0.42 (±0.08) mM | 3.5 (±0.5) $s^{-1}$ |
| IMP dehydrogenase | $NAD^+$ | 0.8 (±0.1) mM | — |
| AMP deaminase | AMP | 0.4 (±0.1) mM | 21 (±4) $s^{-1}$ |

[1]Standard error values are shown in parenthesis
[2]The $k_{cat}$ value for IMP dehydrogenase is the average $k_{cat}$ value calculated from both the IMP- and $NAD^+$-dependent reaction rate plots.

Figure 7:
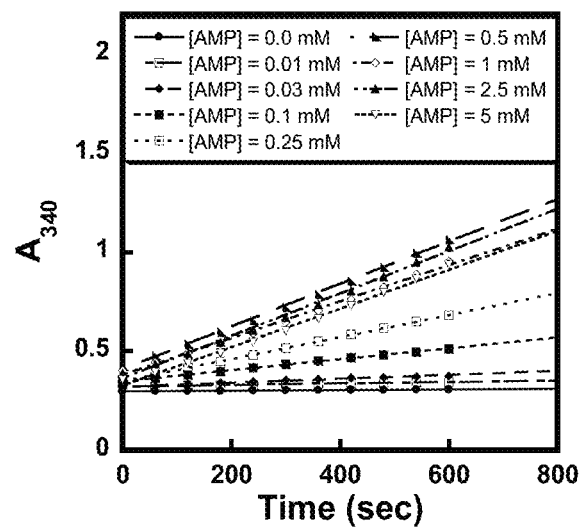
FIGS. 7 and 8 show Monitoring AMP deaminase activity by coupling it to the IMP dehydrogenase reaction. IMP dehydrogenase activity was monitored by following the increase in absorbance at 340 nm.
Figure 8:
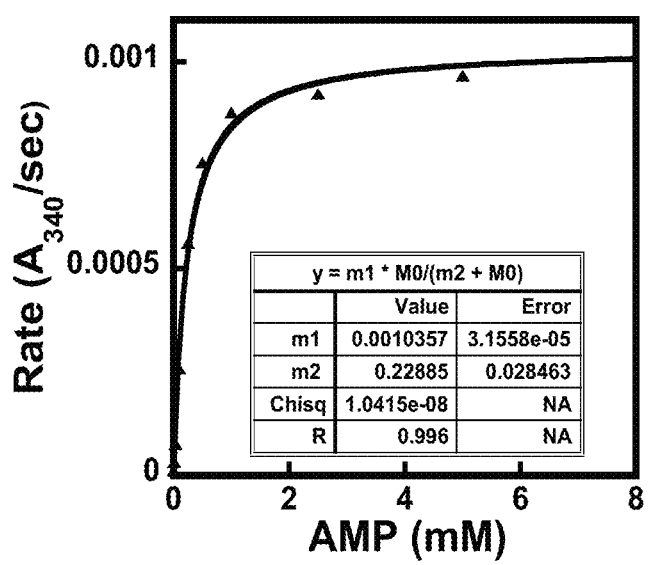

Determination of $K_m$ and $k_{cat}$ values for AMP deaminase. AMP deaminase catalyzes the deamination of AMP, forming IMP and $NH_4^+$, as shown in FIG. 1. This reaction is the first step in the purine nucleotide cycle, which ultimately results in the production of fumarate from aspartic acid. Both ATP and MgATP have been reported to allosterically activate *S. cerevisiae* AMP deaminase. To ensure that AMP deaminase is the limiting enzyme in the assay, varying ratios of AMP deaminase:IMP dehydrogenase were assayed. AMP deaminase:IMP dehydrogenase molar ratios of 1:15 or less were found to result in a linear dependence on AMP deaminase (data not shown). Subsequent kinetic measurements were performed using ratios of AMP deaminase:IMP dehydrogenase at or below this threshold. In agreement with previous investigators, the inventors found that in the presence of ATP, AMP deaminase from *S. cerevisiae* follows classical Michaelis-Menten kinetics, as shown in FIGS. 7 and 8. The $K_m^{AMP}$ value for *S. cerevisiae* AMP deaminase is within experimental error of previously reported values. See Table 1, above. In contrast, the $k_{cat}$ value for the recombinant *S. cerevisiae* AMP deaminase is 200-fold less than previously reported values for AMP deaminase purified from Baker's yeast. Table 1, above. The reason for the lower $k_{cat}$ value of the recombinant enzyme remains to be determined. It is possible that the amino-terminal S-tag/His-tag inhibits the activity of the recombinant AMP deaminase. The presence or absence of bovine serum albumin (0.5 mg/ml) had no significant effect on either $K_m^{AmP}$ or $k_{cat}$ of the *S. ceriviseae* AMP deaminase (data not shown).

Determination of the optimal pH for the coupled assay. To determine the optimal pH for the coupled assay, the pH profiles for IMP dehydrogenase and AMP deaminase were determined between pH 5.5 and 9.0 using 50 mM of either sodium phosphate (pH 5.5-7.5) or TRIS (pH 7.5-9.0) as buffers. The AMP deaminase activity was measured using the coupled assay under conditions where it is the rate-limiting enzyme for all pH values. As a result, the pH profile determined for AMP deaminase and pH profile for the overall coupled reaction are identical.

Figure 9:
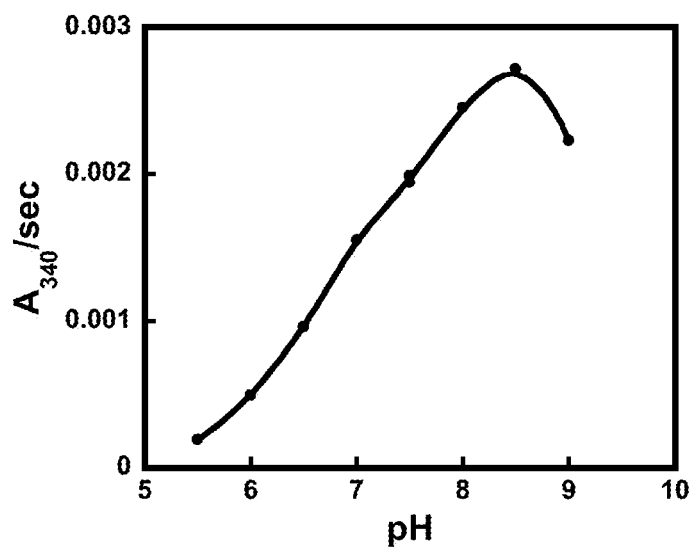
FIGS. 9 and 10 show pH profiles for IMP dehydrogenase and AMP deaminase. The pH profiles for IMP dehydrogenase activity, in FIG. 9, and AMP deaminase activity, in FIG. 10, are shown. The pH of the assay was varied by buffering with either 50 mM sodium phosphate (pH 5.5-7.5) or 50 mM TRIS (pH 7.5-9.0).
Figure 10:
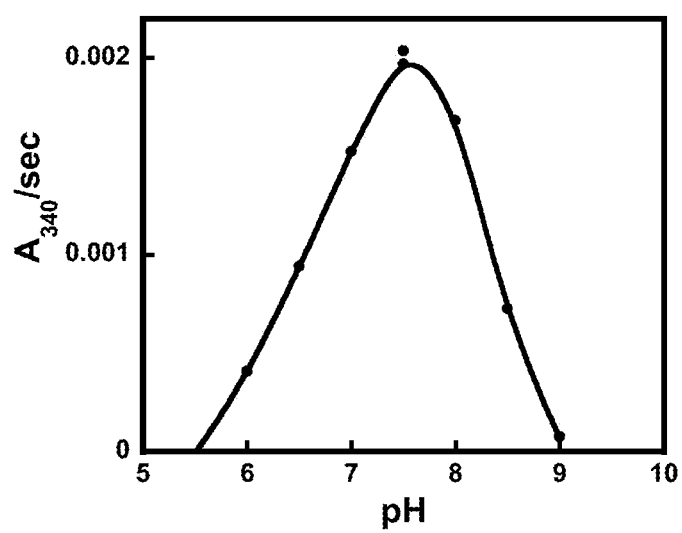
Figure 11:
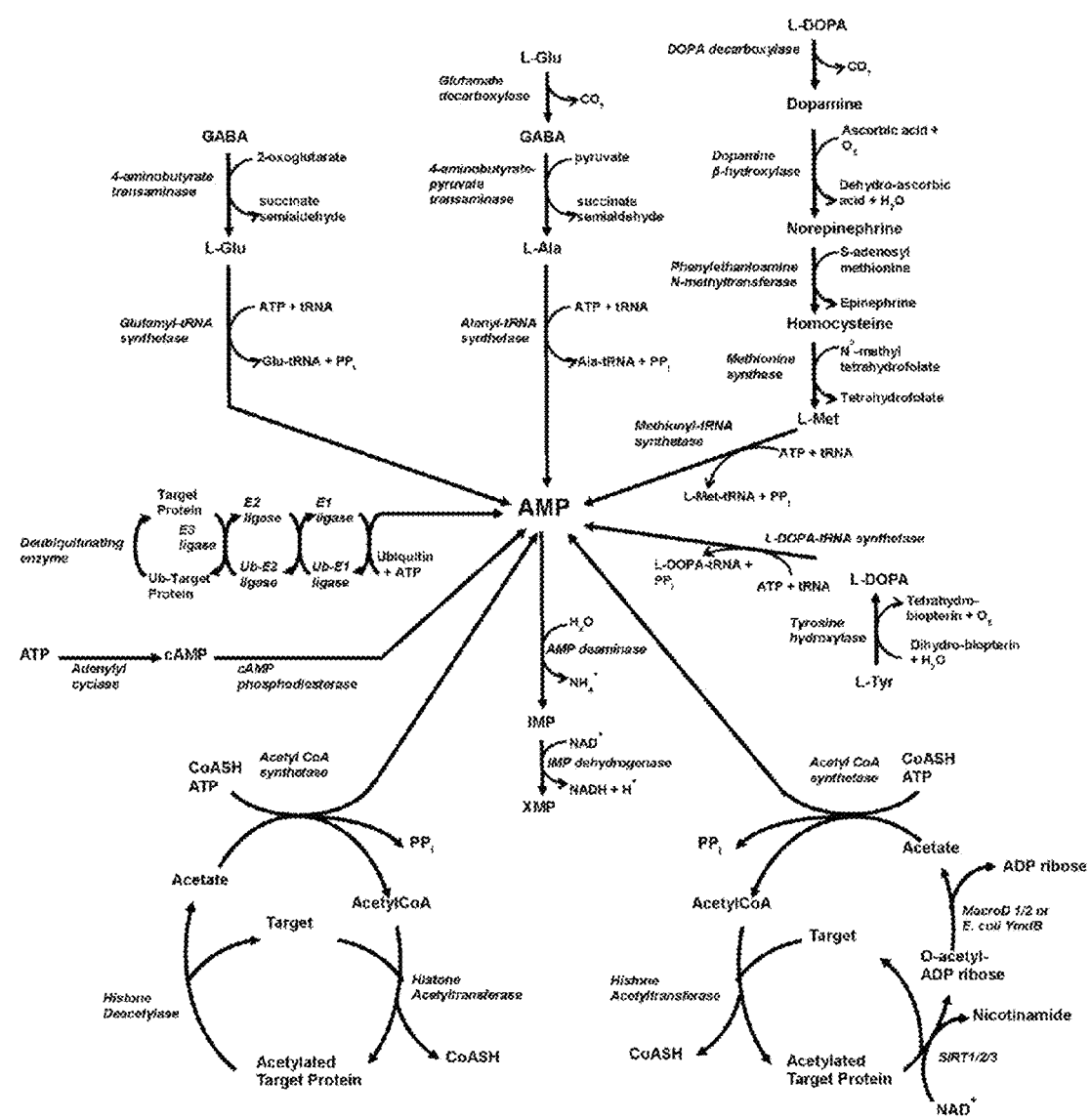
FIG. 11 is a flow diagram showing access points to the AMP assay for various biologically important and medically relevant enzymes. The AMP assay disclosed herein can be coupled to a variety of biologically important pathways through the actions of phosphodiesterases, E1 ubiquitin ligases, aminoacyl-tRNA synthetases, and acetyl CoA synthetase, for example.

Although inorganic phosphate has previously been reported to be inhibitory with respect to AMP deaminase, the inventors observed only minor differences between the sodium phosphate and TRIS buffers at pH 7.5. IMP dehydrogenase exhibits a peak of activity at pH=8.5, as shown in FIG. 9. AMP deaminase displays significant activity between pH 6.5 and 8.5, with maximum activity at pH 7.5, as shown in FIG. 10.

Conclusions: AMP production monitoring assay. The inventors have developed a simple, inexpensive assay to continuously monitor the production of AMP. This assay can be used to monitor the kinetics for enzymes that release AMP as a product, as well as any enzyme in a pathway that can be coupled to a reaction that releases AMP. Applications include the high-throughput screening and characterization of lead compounds for potential drugs, including those used to treat pulmonary arterial hypertension, coronary heart disease, diabetes, dementia, depression, schizophrenia, cancer, and multidrug-resistant bacteria.

Materials and Methods: aminoacyl-tRNA synthetase assay. Materials—Materials were obtained from the following sources: *Thermus thermophilus* DNA (American Tissue and Type Collection, Manassas, Va.), TOPO® TA Cloning® Kit (Life Technologies, Grand Island, N.Y.), pGEM®-T Easy cloning kit and Wizard® SV Gel and PCR Clean-Up System (Promega, Madison, Wis.), pET30a(+) expression vector, BL21 DE3 *Escherichia coli* and Rosetta™ 2 DE3 *Escherichia coli* cells (EMD Biosciences, Billerica, Miss.), XL2 Blue™ *Escherichia coli* cells (Agilent Technologies, Santa Clara, Calif.), E.Z.N.A.® Plasmid DNA Mini I Kit (Omega Bio-Tek, Norcross, Ga.), T4 DNA ligase, NcoI-HF®, NdeI-HF®, XhoI, EcoRI, and FokI (New England Biolabs, Ipswich, Mass.), Taq DNA polymerase (G-Biosciences, St. Louis, Mo.), BIOMOL® Green reagent (ENZO® Life Sciences, Farmingdale, N.Y.), [$^{14}C$]L-tyrosine (Moravek Biochemicals, Brea, Calif.), AMP (Research Products International Corporation, Mount Prospect, Ill.), ATP, IMP, $NAD^+$, L-tyrosine, D-tyrosine (VWR International, Radnor, Pa.), and oligonucleotides (Integrated DNA Technologies, Coralville, Iowa). All other reagents were obtained from ThermoFisher Scientific (Waltham, Mass.).

DNA sequencing was performed by the DNA Lab at Arizona State University (Tempe, Ariz.). Curve fitting and graphing was performed using Grafit™ (Erithacus Software Ltd., Horley, Surrey, UK) and Kaleidograph® (Synergy Software, Reading, Pa.). The *Mycobacterium tuberculosis* cyclodityrosine synthase expression clone and *S. cerevisiae* genomic DNA were the generous gifts of Professor John Blanchard (Albert Einstein College of Medicine) and Professor Kelly Tatchell (LSU Health Sciences Center in Shreveport), respectively.

Construction of expression vectors for *Geobacillus stearothermophilus* tyrosyl-tRNA synthetase, *Saccharomyces cerevisiae* inorganic pyrophosphatase, and *Thermus thermophilus* D-tyrosyl-tRNA deacylase—The polymerase chain reaction was used to amplify the open reading frame for *G. stearothermophilus* tyrosyl-tRNA synthetase from the pYTS5-WT3 plasmid. Primers were designed such that the amplified DNA contained unique NdeI and XhoI restriction sites at the 5' and 3' ends, respectively. The amplified open reading frames were initially ligated into the PCR2.1-TOPO TA vector and transformed into XL2 Blue *E. coli* cells. Individual colonies were selected and grown overnight in 2 ml of 2×YT media (16 g/L Tryptone, 10 g/L Yeast Extract, 5 g/L NaCl), followed by PCR screening to identify positive clones. Plasmids were isolated from the positive cultures using an E.Z.N.A. Plasmid DNA Mini I kit and the inserted DNA was sequenced by the Arizona State University DNA Sequencing Facility. The open reading frame was subsequently removed by digestion with NdeI-HF and XhoI, gel purified using the Wizard SV Gel and PCR Clean-Up System, and subcloned into the pET30a(+) vector such that protein expression will result in tyrosyl-tRNA synthetase fused to a carboxyl-terminal His-Tag. This clone was designated pYTS8-WT.

The polymerase chain reaction was used to amplify the open reading frame for inorganic pyrophosphatase from *S. cerevisiae* strain KT1112 genomic DNA. Primers were designed such that the amplified DNA contained unique NdeI and XhoI restriction sites at the 5' and 3' ends, respectively. Amplified open reading frames were initially ligated into the pGEM-T Easy vector and transformed into XL2 Blue *E. coli* cells. Positive clones were identified and sequenced as described above. The open reading frame was subsequently removed by digestion with NdeI-HF and XhoI, gel purified, and subcloned into the pET30a(+) vector such that protein expression will result in inorganic pyrophosphatase fused to a carboxyl-terminal His-Tag. This clone was designated pET30-PPI5.

The polymerase chain reaction was used to amplify the open reading frame for D-tyrosyl-tRNA deacylase directly from *T. thermophilus* genomic DNA. Primers were designed such that the amplified DNA contained a unique NcoI restriction site at the 5' end. The amplified open reading frame was initially ligated into the PCR2.1-TOPO TA vector (which contains EcoRI sites on both sides of the inserted sequence) and transformed into XL2 Blue *E. coli* cells. Positive clones were identified and sequenced as described above. The open reading frame was subsequently removed by digestion with NcoI-HF and EcoRI, gel purified, and subcloned into the pET30a(+) vector such that protein expression results in a protein containing an amino-terminal S-Tag/His-Tag followed by the D-tyrosyl-tRNA deacylase coding sequence. This clone was designated pDTD1-WT. All procedures involving recombinant DNA were performed using NIH biosafety level 1 containment procedures, and were approved by the LSU Health Sciences Center Biosafety Committee.

Protein expression and purification—*Saccharomyces cerevisiae* AMP deaminase and IMP dehydrogenase were expressed in *E. coli* Rosetta 2 DE3 cells and *S. cerevisiae* inorganic pyrophosphatase, *M. tuberculosis* cyclodityrosine synthase, *T. thermophilus* D-tyrosyl-tRNA deacylase, and *G. stearothermophilus* tyrosyl-tRNA synthetase were expressed in *E. coli* BL21 DE3 cells. Purification of the recombinant proteins was carried out by NiNTA affinity chromatography using procedures previously described, such as in T. A. Kleeman, D. Wei, K. L. Simpson, E. A. First, "Human tyrosyl-tRNA synthetase shares amino acid sequence homology with a putative cytokine," *The Journal of Biological Chemistry*, 272 (1997) 14420-14425 and J. Austin, E. A. First, "Catalysis of tyrosyl-adenylate formation by the human tyrosyl-tRNA synthetase," *The Journal of Biological Chemistry*, 277 (2002) 14812-14820, such procedures incorporated herein. Tyrosyl-tRNA synthetase was further purified using anion exchange HPLC as previously described, such as in Id, such procedures incorporated herein. Proteins were purified to >95% homogeneity, based on SDS-polyacrylamide gel electrophoresis. Protein concentrations were calculated based on $A_{280}$ measurements ($\epsilon_{280}$=43630, 470320, 99480, 34840, 11920, and 107720 $M^{-1}$ $cm^{-1}$ for inorganic pyrophosphatase, AMP deaminase, IMP dehydrogenase, cyclodityrosine synthase, D-tyrosyl-tRNA deacylase, and tyrosyl-tRNA synthetase, respectively). Extinction coefficients were calculated using the ExPASy ProtParam tool, assuming that AMP deaminase and IMP dehydrogenase are homotetramers and cyclodityrosine synthase, D-tyrosyl-tRNA deacylase, and tyrosyl-tRNA synthetase are all homodimers. Purified proteins were stored at −70° C. in the following buffers: tyrosyl-tRNA synthetase—20 mM TRIS, pH 7.8, 1 mM EDTA, 10 mM β-mercaptoethanol, 10% glycerol (v/v); cyclodityrosine synthase—50 mM TRIS, pH 7.8, 250 mM NaCl, 50% glycerol (v/v); D-tyrosyl-tRNA deacylase—50 mM TRIS, pH 7.5, 10 mM β-mercaptoethanol, 50% glycerol (v/v); inorganic pyrophosphatase—20 mM TRIS, pH 7.8, 100 mM KCl, 1 mM dithiothreitol, 50% glycerol (v/v); AMP deaminase—50 mM TRIS, pH 7.5, 20 mM β-mercaptoethanol, 10 mM $MgCl_2$, and 10% glycerol (v/v); IMP dehydrogenase—50 mM TRIS, pH 7.5, 20 mM β-mercaptoethanol, 10 mM $MgCl_2$, and 10% glycerol (v/v). The activities of IMP dehydrogenase and AMP deaminase were measured using the AMP production monitoring assay described above. The inorganic pyrophosphatase activity was determined using BIOMOL Green (a molybdate/malachite green-based reagent). In this assay, inorganic pyrophosphatase is incubated with 5 mM disodium pyrophosphate in the presence of 144 mM Tris, pH 7.78, and 10 mM $MgCl_2$, for 30 minutes at 25° C. The reaction is terminated by the addition of BIOMOL green reagent and, after 30 minutes, the absorbance at 620 nm is compared to that of a phosphate standard curve to determine the activity of the enzyme. One unit of activity is equivalent to one micromole of phosphate released per minute at saturating pyrophosphate concentrations. The activity of tyrosyl-tRNA synthetase was measured using an active site titration filter binding assay in which the incorporation of [$^{14}$C]L-tyrosine (485 Ci/mol) into the enzyme-bound tyrosyl-adenylate intermediate (TyrRS•Tyr-AMP) is monitored. Comparison of the concentration of tyrosyl-tRNA synthetase calculated based on the active site titration and $A_{280}$ measurements indicates that the enzyme is >95% active ($\epsilon$280=107,720 and Mr=96,461 for the His-tagged tyrosyl-tRNA synthetase homodimer). The activities of cyclodityrosine synthase and D-tyrosyl-tRNA deacylase were determined using the assays described below.

In vitro transcription and purification of tRNA$^{Tyr}$—G. stearotheromophilus tRNA$^{Tyr}$ was synthesized by runoff in vitro transcription of the pGFX-WT plasmid using T7 RNA polymerase as previously described, in, for example, T. A. Kleeman, D. Wei, K. L. Simpson, E. A. First, "Human tyrosyl-tRNA synthetase shares amino acid sequence homology with a putative cytokine," The Journal of Biological Chemistry, 272 (1997) 14420-14425, and Y. Xin, W. Li, E. A. First, "The 'KMSKS' motif in tyrosyl-tRNA synthetase participates in the initial binding of tRNA(Tyr)," Biochemistry, 39 (2000) 340-347, such processes incorporated herein. The pGFX-WT plasmid contains a FokI site nine nucleotides downstream of the tRNA$^{Tyr}$ gene. Digestion with FokI results in cleavage at the 3' terminus of the tRNA$^{Tyr}$ coding sequence. tRNA$^{Tyr}$ concentrations were calculated based on their absorbance at 260 nm using an extinction coefficient of 806,100 M$^{-1}$ cm$^{-1}$, as calculated by the nearest neighbor method, and by monitoring the incorporation of [$^{14}$C]L-tyrosine into the Tyr-tRNA product using a filter binding assay as described previously, in for example, J. M. Avis, A. G. Day, G. A. Garcia, A. R. Fersht, "Reaction of modified and unmodified tRNA(Tyr) substrates with tyrosyl-tRNA synthetase (Bacillus stearothermophilus)," Biochemistry, 32 (1993) 5312-5320; M. J. Cavaluzzi, P. N. Borer, "Revised UV extinction coefficients for nucleoside-5'-monophosphates and unpaired DNA and RNA," Nucleic Acids Research, 32 (2004) e13; and C. R. Cantor, M. M. Warshaw, H. Shapiro, "Oligonucleotide interactions. 3. Circular dichroism studies of the conformation of deoxyoligonucleotides," Biopolymers, 9 (1970) 1059-1077, such procedure incorporated herein. Comparing the tRNA$^{Tyr}$ concentration determined from A$_{260}$ measurements with the amount of tRNA$^{Tyr}$ that is aminoacylated in the filter binding assay indicated that >70% of the tRNA$^{Tyr}$ could be aminoacylated by tyrosine.

Kinetic analyses—Tyrosyl-tRNA synthetase was assayed in buffer containing 50 mM TRIS, pH 7.78, 100 mM KCl, 0.1 mM dithiothreitol, 10 mM MgCl$_2$, 10 mM MgATP, 5 mM NAD$^+$, 0.16 µM AMP deaminase, 0.64 µM IMP dehydrogenase, 8 µM cycloditypesine synthase, 0.005-1.0 µM tyrosyl-tRNA synthetase, 0.002 units inorganic pyrophosphatase, and either 5 µM tRNA$^{Tyr}$ or 500 µM L-tyrosine (for determination of K$_m^{L-Tyr}$ and K$_m^{tRNA}$, respectively). The pH of all stock solutions was adjusted to 7.0 prior to use. All kinetic assays were performed in 96 well microtiter plates at 25° C. using either 100 or 200 µl of assay mix per well. Under these conditions, the path lengths are 0.28 and 0.56 cm, respectively. The reaction rate for formation of the L-Tyr-tRNA$^{TYr}$ product was determined by monitoring the increase in absorbance at 340 nm associated with the conversion of NAD$^+$ to NADH using a BioTek Synergy 4 plate reader ($\epsilon_{340}$=6220 M$^{-1}$ cm$^{-1}$). The K$_m^{L-Tyr}$ value was determined by varying the concentration of tyrosine from 0-600 µM and plotting the change in rate vs. tyrosine concentration. The K$_m^{tRNA}$ value was determined by varying the concentration of tRNA$^{Tyr}$ from 0-10 µM and plotting the change in rate vs. tRNA concentration. The K$_m^{D-Tyr}$ value was determined using the protocol described above for determining K$_m^{L-Tyr}$, except that D-tyrosine and D-tyrosyl-tRNA deacylase (final concentration=50 µM) replaced L-tyrosine and cycloditypesine synthase in the assay.

Cycloditypesine synthase activity was assayed under the same conditions as the tyrosyl-tRNA synthetase assay described above, except that the concentrations of L-tyrosine, cycloditypesine synthase, and tyrosyl-tRNA synthetase were 0.3 mM, 0.05 µM, and 5 µM, respectively, and the concentration of tRNA$^{Tyr}$ was varied from 0-30 µM. The assay was initiated by the addition of cycloditypesine synthase. D-tyrosyl-tRNA deacylase activity was assayed under the same conditions as the cycloditypesine synthase assay, except that cycloditypesine synthase was replaced by 5 µM D-tyrosyl-tRNA deacylase and L-tyrosine was replaced by 0.3 mM D-tyrosine. The assay was initiated by the addition of D-tyrosyl-tRNA deacylase.

Initial rates for each substrate concentration were determined from a linear fit of the data (A$_{340}$ vs. time). K$_m$ and V$_{max}$ values were determined by fitting a plot of the initial rate vs. substrate concentration to the Michaelis-Menten equation, the same equations (1) and (2) above:

$$v_o = \frac{V_{max}[S]}{K_m + [S]} \quad (1)$$

where v$_o$ is the initial rate of the reaction and [S] is the substrate concentration. k$_{cat}$ values were calculated from the equation:

$$V_{max} = k_{cat}[E] \quad (2)$$

where [E] is the molar concentration of the enzyme in the assay.

Figure 12:
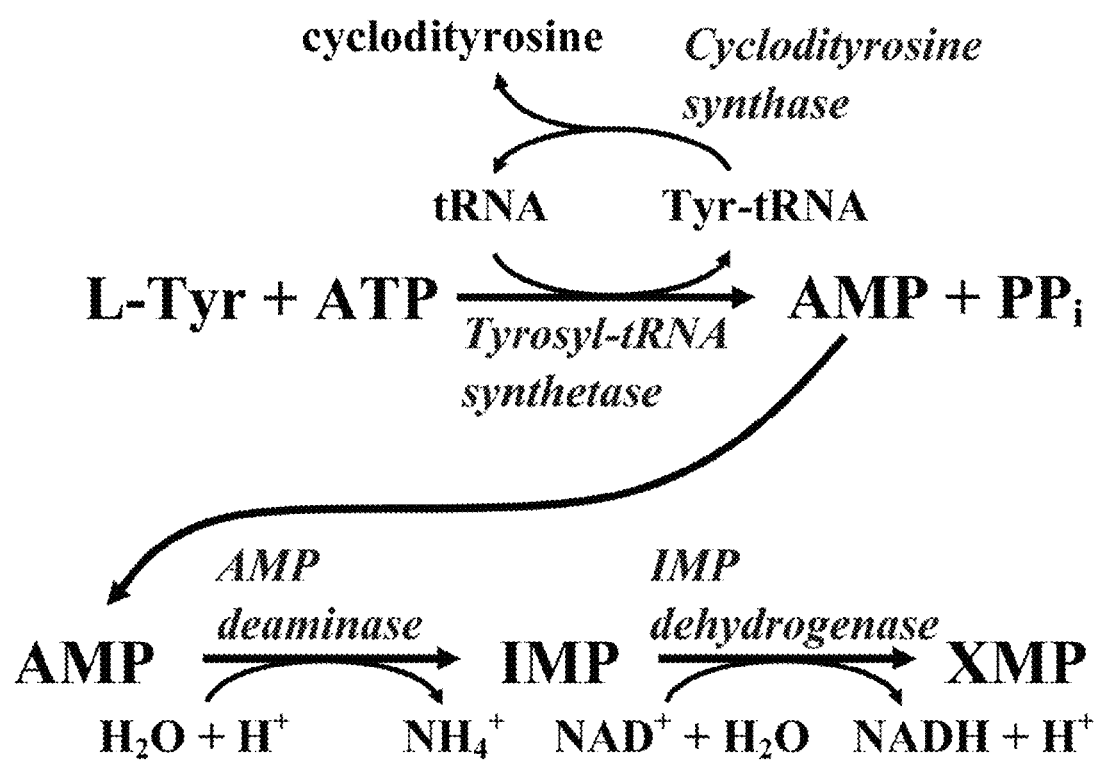
FIG. 12 is the reaction scheme for the tyrosyl-tRNA synthetase assay. The production of AMP by tyrosyl-tRNA synthetase is monitored by coupling it to AMP deaminase and IMP dehydrogenase and following the increase in absorbance at 340 nm resulting from the reduction of NAD⁺. The Tyr-tRNA$^{Tyr}$ product is cleaved by *M. tuberculosis* cyclodityrosine synthase, releasing cyclodityrosine and regenerating the tRNA$^{Tyr}$ substrate. Tyr, AMP, IMP, XMP, and PP$_i$ represent L-tyrosine, adenosine 5'-monophosphate, inosine 5'-monophosphate, xanthine 5'-monophosphate, and inorganic pyrophosphate, respectively.
Figure 13:
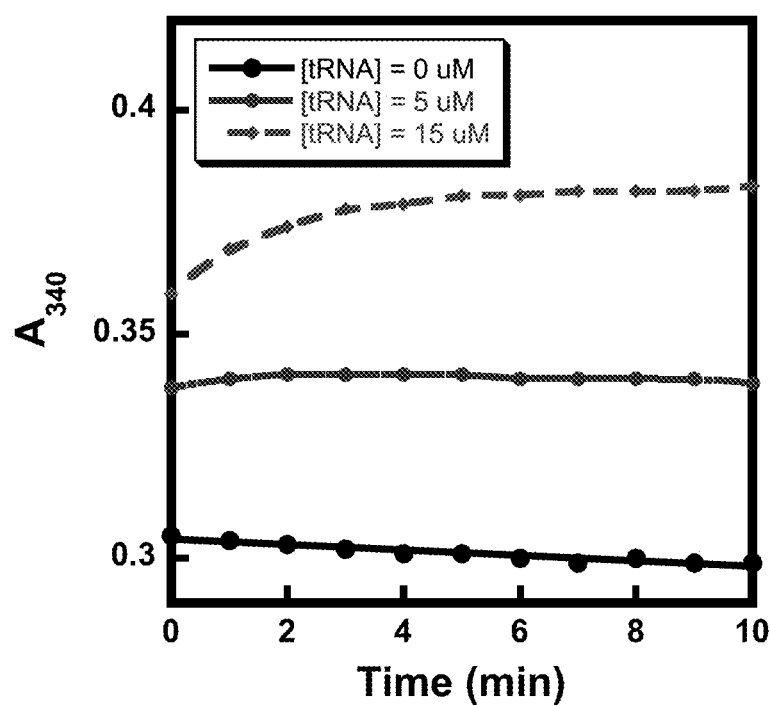
FIGS. 13-15 show Cyclodityrosine synthase regenerates the tRNA substrate in situ. The activity of tyrosyl-tRNA synthetase is monitored via the production of NADH and the corresponding increase in absorbance at 340 nm. Typical curves showing the activity of tyrosyl-tRNA synthetase at varying concentrations of tRNA in the absence, FIG. 13, and presence, FIG. 14, of *M. tuberculosis* cyclodityrosine synthase are shown.

Results: aminoacyl-tRNA synthetase assay. Monitoring tyrosyl-tRNA synthetase activity via the release of AMP—Tyrosyl-tRNA synthetase catalyzes the conversion of tyrosine, ATP and tRNA$^{Tyr}$ to tyrosyl-tRNA$^{Tyr}$, AMP, and inorganic pyrophosphate. This reaction can be monitored by coupling the production of AMP to the reduction of NAD$^+$ via AMP deaminase and IMP dehydrogenase, shown in FIG. 12, allowing the tRNA aminoacylation reaction to be continuously monitored by following the production of NADH and the corresponding increase in absorbance at 340 nm. If tRNA is not regenerated by cleavage of the Tyr-tRNA product, the sensitivity of the assay is limited by the initial concentration of the tRNA$^{Tyr}$, since the generation of NADH ceases once the tRNA$^{Tyr}$ substrate has been depleted, shown in FIG. 13.

Figure 14:
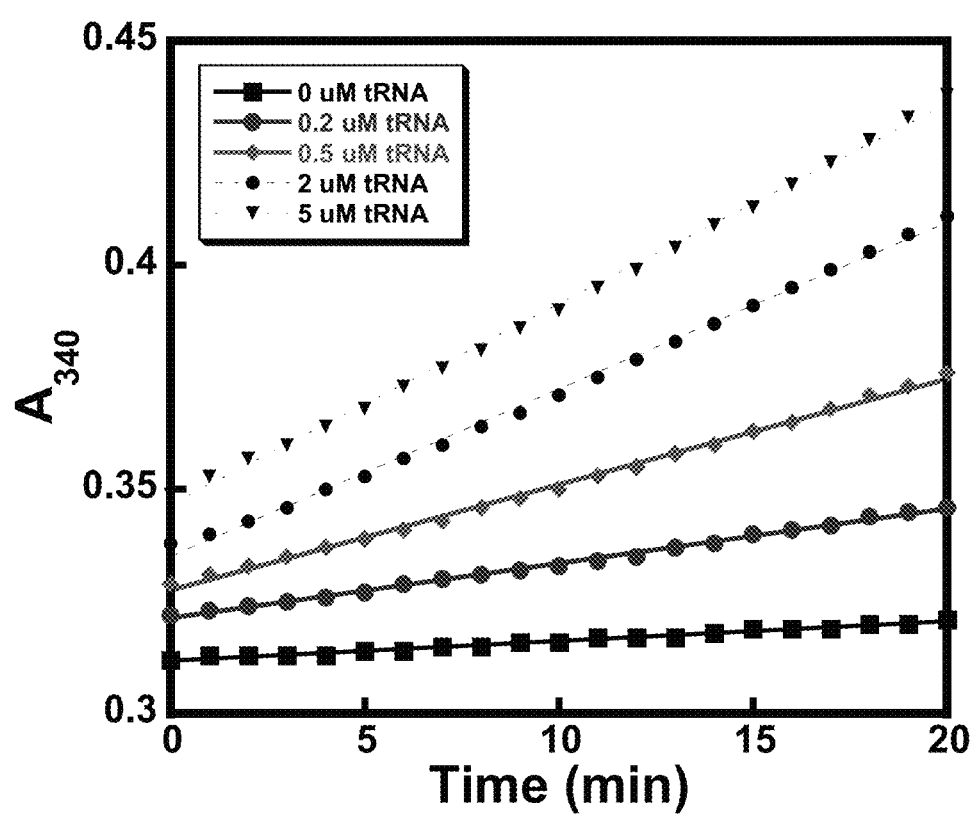

To overcome the above limitation, cycloditypesine synthase was added to the tyrosyl-tRNA synthetase assay. Cycloditypesine synthase catalyzes the formation of cycloditypesine from two molecules of L-tyrosyl-tRNA$^{Tyr}$, releasing two molecules of tRNA$^{Tyr}$ in the process. By including cycloditypesine synthase in the assay, the tRNA$^{Tyr}$ substrate is continuously regenerated from the Tyr-tRNA$^{Tyr}$ product. As a result, tRNA$^{Tyr}$ is no longer the limiting substrate in the reaction, substantially increasing both the amount of NADH that is generated during the assay and the length of time that tyrosyl-tRNA synthetase activity can be monitored, shown in FIG. 14. In addition to increasing the sensitivity of the assay, recycling the Tyr-tRNA$^{Tyr}$ product allows subsaturating concentrations of tRNA$^{Tyr}$ to be used, making it possible to determine the Michaelis constant for tRNA$^{Tyr}$ (K$_m^{tRNA}$).

Figure 15:
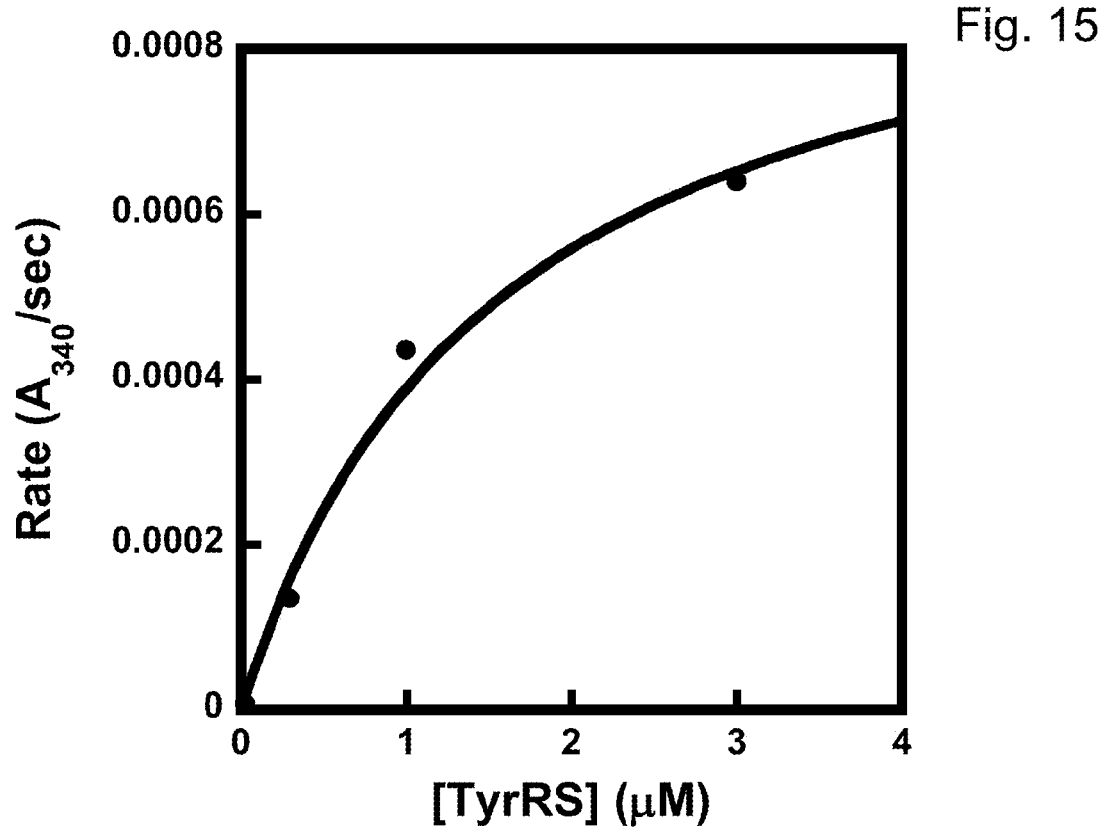
Figure 16:
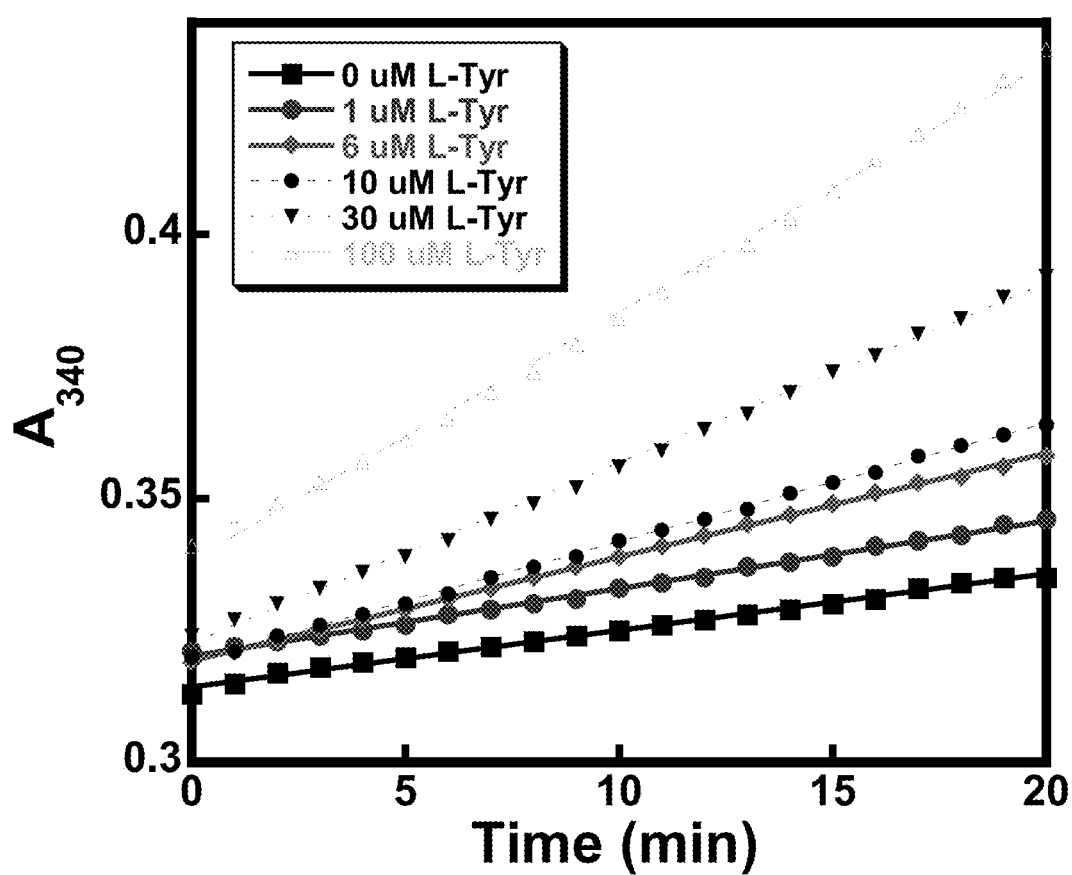
FIGS. 16-19 show determination of steady-state kinetic constants using the tyrosyl-tRNA synthetase assay. Typical initial rate and substrate-dependence curves for *G. stearothermophilus* tyrosyl-tRNA synthetase are shown. Tyrosyl-tRNA synthetase activity was monitored by following the increase in absorbance at 340 nm. The concentrations of cyclodityrosine synthase and tyrosyl-tRNA synthetase in the assays are 8 μM and 5 nM, respectively.
Figure 17:
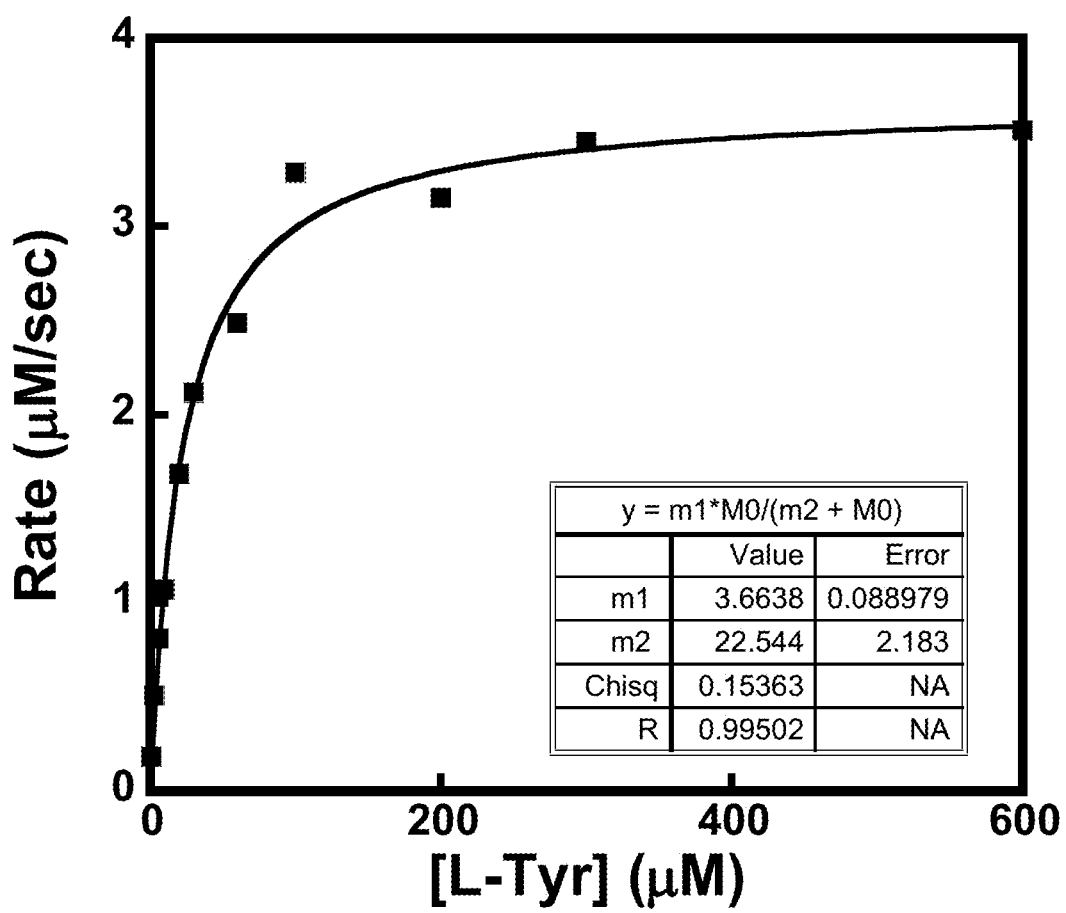
Figure 18:
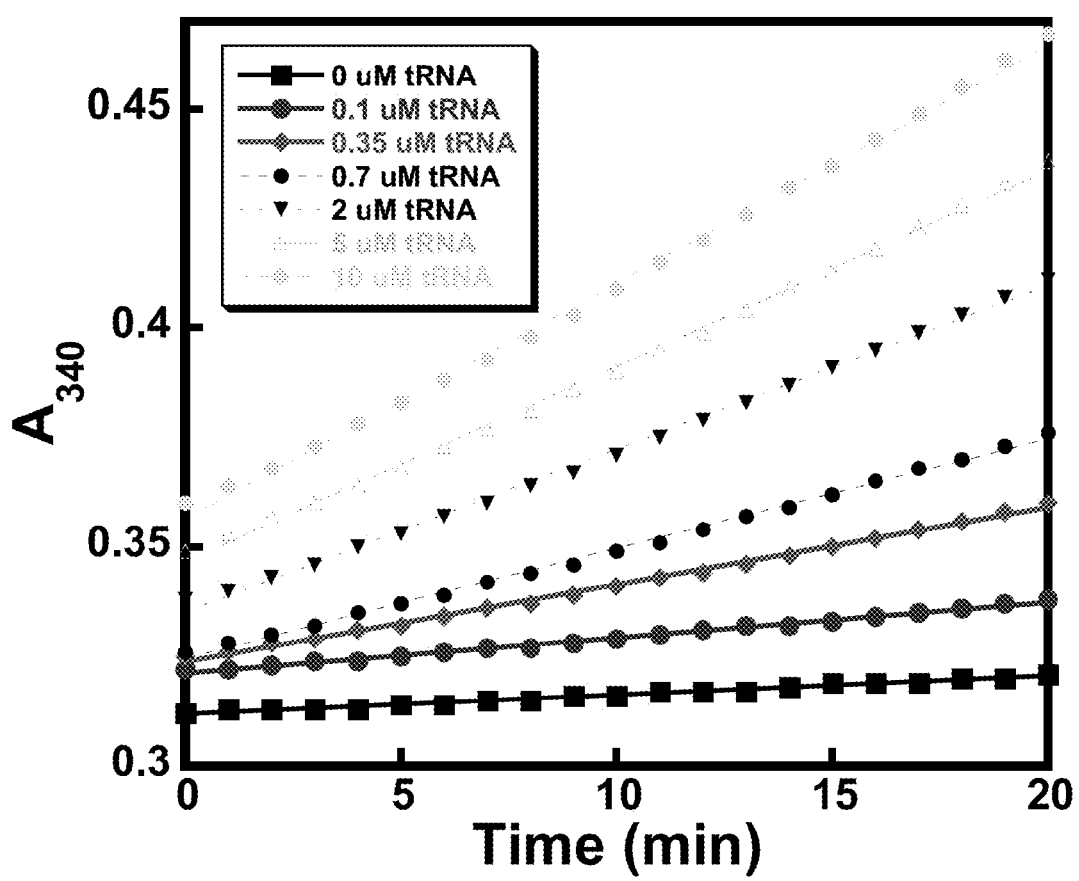
Figure 19:
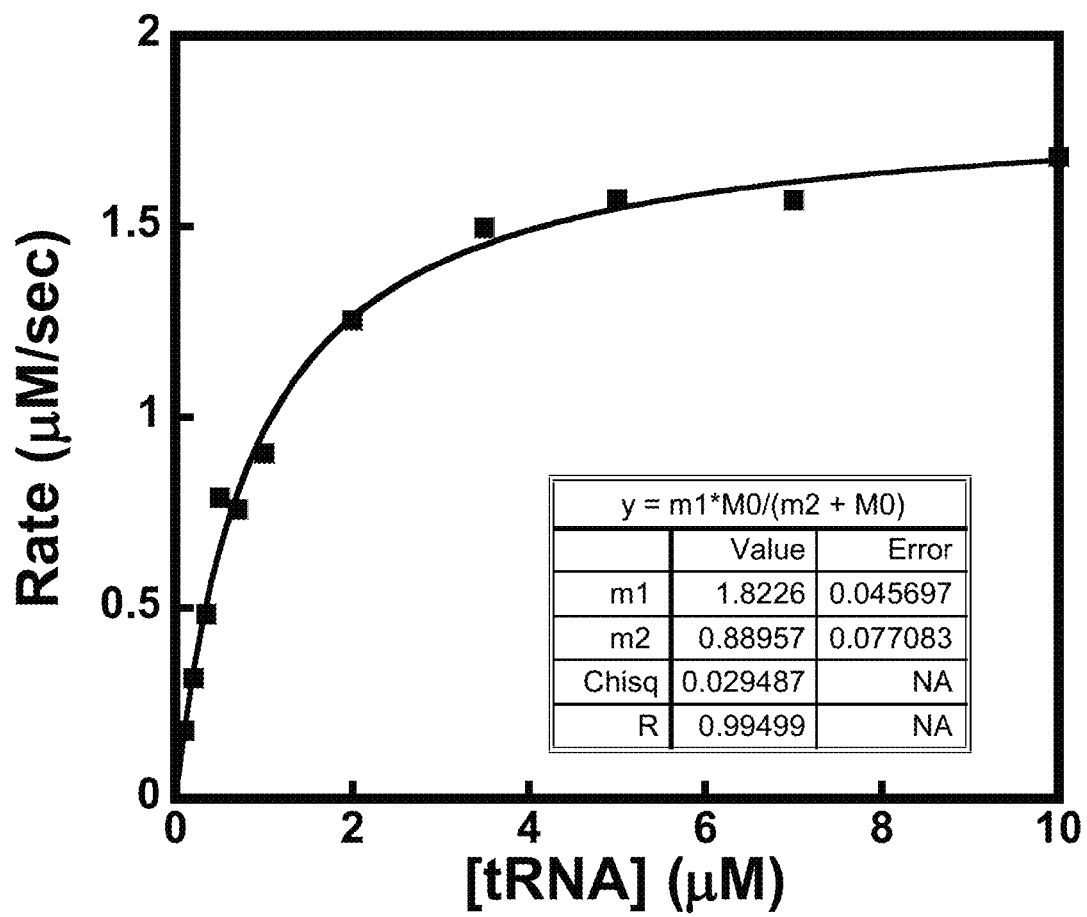

Determination of K$_m$ and k$_{cat}$ values for tyrosyl-tRNA synthetase—To ensure that tyrosyl-tRNA synthetase is the rate-limiting enzyme, the assay was performed using varying concentrations of G. stearothermophilus tyrosyl-tRNA synthetase. Using the reaction conditions described in the Experimental Methods section, the assay was found to be linear for concentrations up to 1 µM tyrosyl-tRNA synthetase when the concentration of cycloditypesine is 8 µM (FIG. 15). To determine the K$_m^{L-Tyr}$, K$_m^{tRNA}$, and k$_{cat}$ values for G. stearothermophilus tyrosyl-tRNA synthetase, the reaction rate was determined at varying concentrations of either L-tyrosine or tRNA$^{Tyr}$ using 10 mM MgATP (2.5×K$_d$)

and saturating concentrations of either tRNA$^{Tyr}$ or L-tyrosine, shown in FIGS. 16 and 18. Under these conditions, $K_m^{L-Tyr}$ and $K_m^{tRNA}$ measure the affinity of L-tyrosine and tRNA$^{Tyr}$ for the TyrRS.ATP.tRNA and TyrRS.Tyr-AMP complexes, respectively. The aminoacylation of tRNA$^{Tyr}$ by L-tyrosine follows classical Michaelis-Menten kinetics, shown in FIGS. 17 and 19. The values for $K_m^{L-Tyr}$, $K_m^{tRNA}$, and $k_{cat}$ for both the L-tyrosine and tRNA$^{Tyr}$ substrates (See Table 2, below) are similar to previously reported values for the binding of L-tyrosine and the aminoacylation of tRNA$^{Tyr}$ by *G. stearothermophilus* tyrosyl-tRNA synthetase.

TABLE 2

| | L-Tyrosine[1] | D-Tyrosine[1] |
|---|---|---|
| $K_m^{Tyr}$ | 24 (±3) µM | 23 (±6) µM |
| $K_m^{tRNA}$ | 0.9 (±0.2) µM | 0.5 (±0.1) µM |
| $k_{cat}$ | 2.8 (±0.6) s$^{-1}$ | 0.32 (±0.08) s$^{-1}$ |

[1]Standard error values are shown in parenthesis

Figure 20:
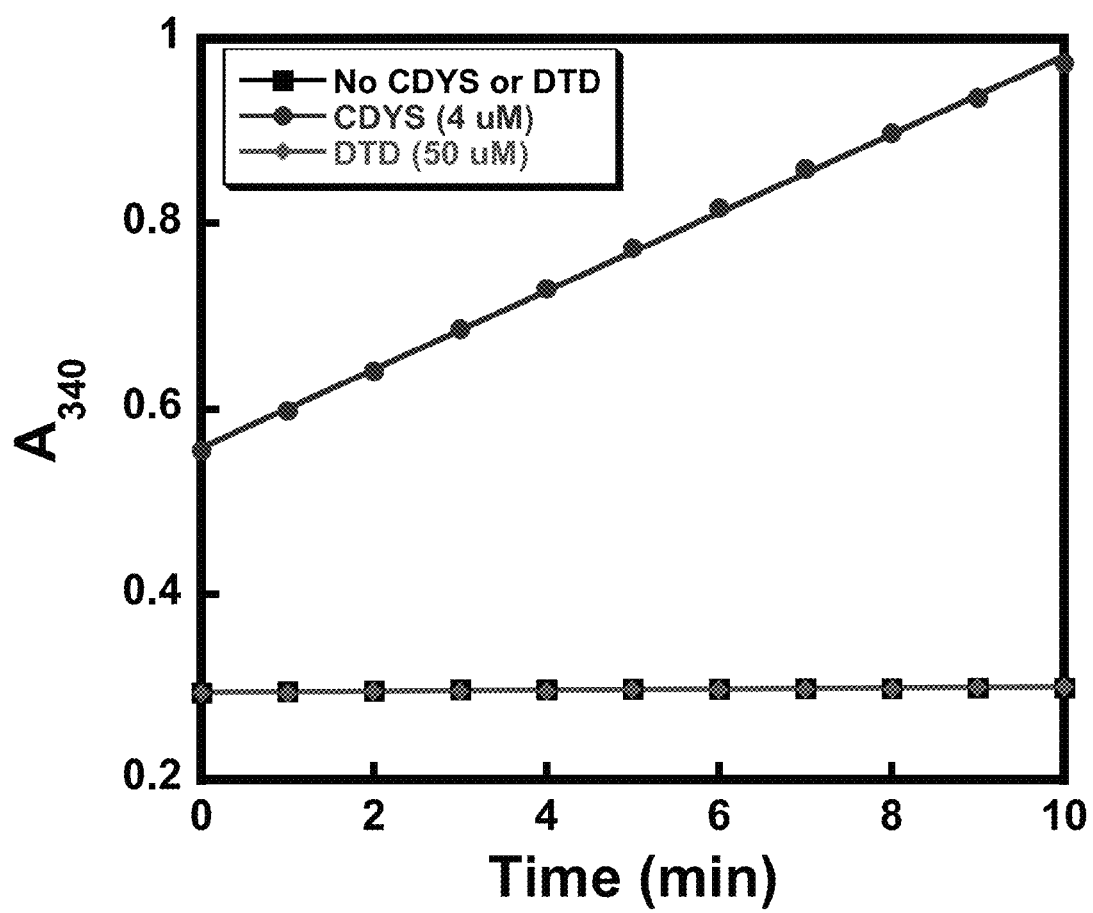
FIGS. 20 and 21 show the stereospecificity of *Mycobacterium tuberculosis* cyclodityrosine synthase and *Thermus thermophilus* D-tyrosyl-tRNA deacylase. The stereospecificities of cyclodityrosine synthase and D-tyrosyl-tRNA deacylase were determined by monitoring formation of NADH when L- and D-tyrosine are the substrates (FIGS. 20 and 21, respectively). Typical time courses for the reactions are shown. The concentrations of tyrosyl-tRNA synthetase, cyclodityrosine synthase, and D-tyrosyl-tRNA deacylase are 0.5 μM, 4 μM, and 50 μM, respectively.
Figure 21:
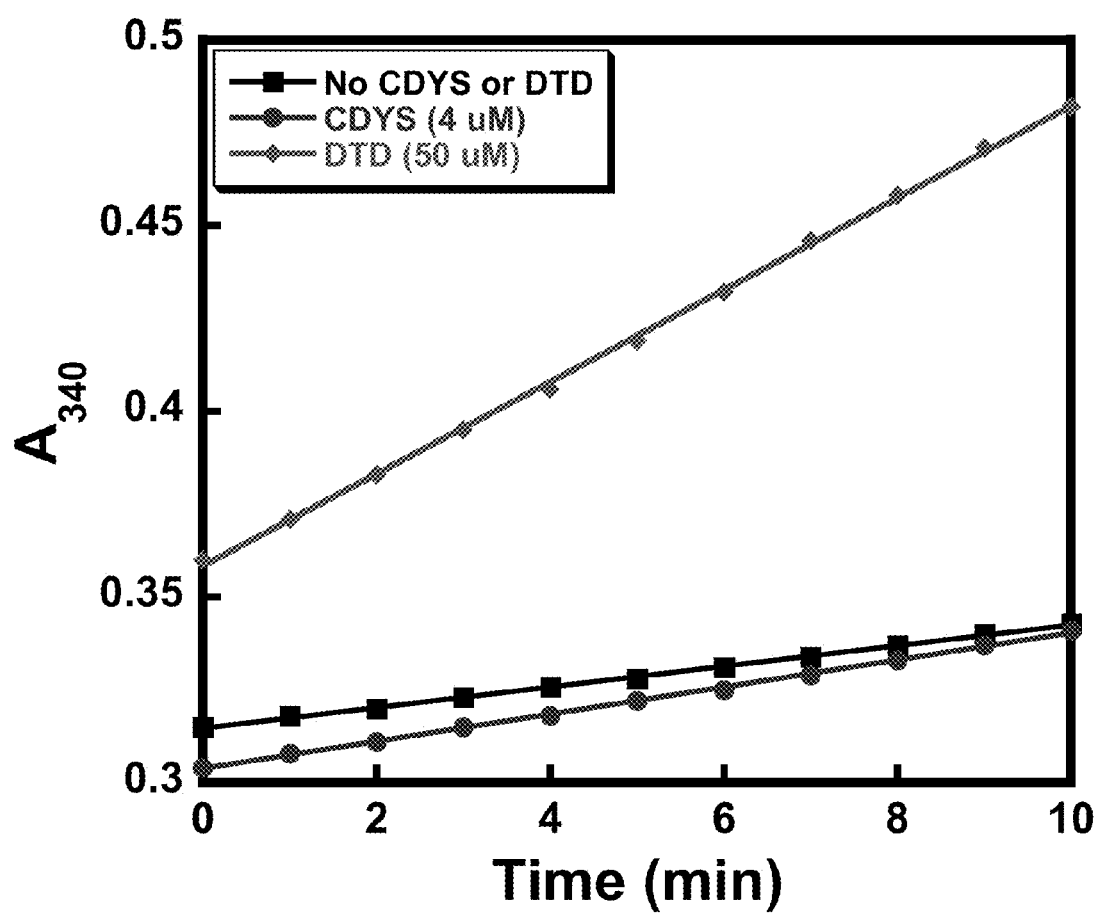

Monitoring the aminoacylation of tRNA$^{Tyr}$ by D-tyrosine—In contrast to most aminoacyl-tRNA synthetases, tyrosyl-tRNA synthetase can catalyze the aminoacylation of tRNA by the D-stereoisomer of its cognate amino acid. To determine whether cyclodityrosine synthase can use D-tyrosyl-tRNA$^{TYr}$ as a substrate, the inventors replaced L-tyrosine with D-tyrosine in the tyrosyl-tRNA synthetase assay. Cyclodityrosine synthase shows little or no activity towards D-Tyr-tRNA$^{Tyr}$, as shown in FIG. 20. This is a novel reporting regarding the stereospecificity of cyclodityrosine synthase. In contrast, replacing cyclodityrosine synthase with D-tyrosyl-tRNA deacylase, an enzyme that specifically hydrolyzes D-aminoacyl-tRNAs, results in the continuous production of NADH in the presence of D-tyrosine, but not L-tyrosine, shown in FIGS. 20 and 21. These results indicate that *T. thermophilus* D-tyrosyl-tRNA deacylase is specific for D-aminoacyl-tRNAs.

Figure 22:
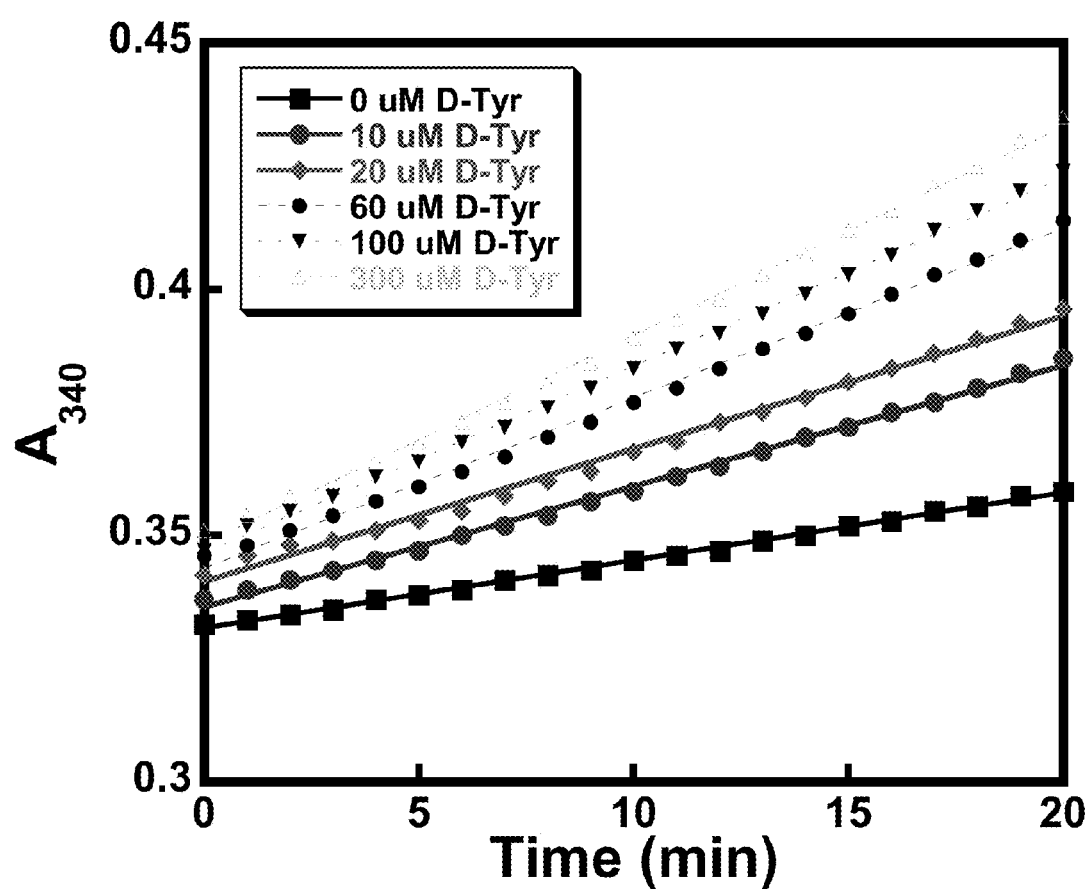
FIGS. 22-25 show monitoring the aminoacylation of tRNA by D-tyrosine. Typical initial rate and substrate-dependence curves for the *G. stearothermophilus* tyrosyl-tRNA synthetase catalyzed aminoacylation of tRNA by D-tyrosine are shown. *G. stearothermophilus* tyrosyl-tRNA synthetase activity was monitored by following the increase in absorbance at 340 nm. The concentrations of tyrosyl-tRNA synthetase and D-tyrosyl-tRNA deacylase used in the assays are 125 nM and 50 μM, respectively.
Figure 23:
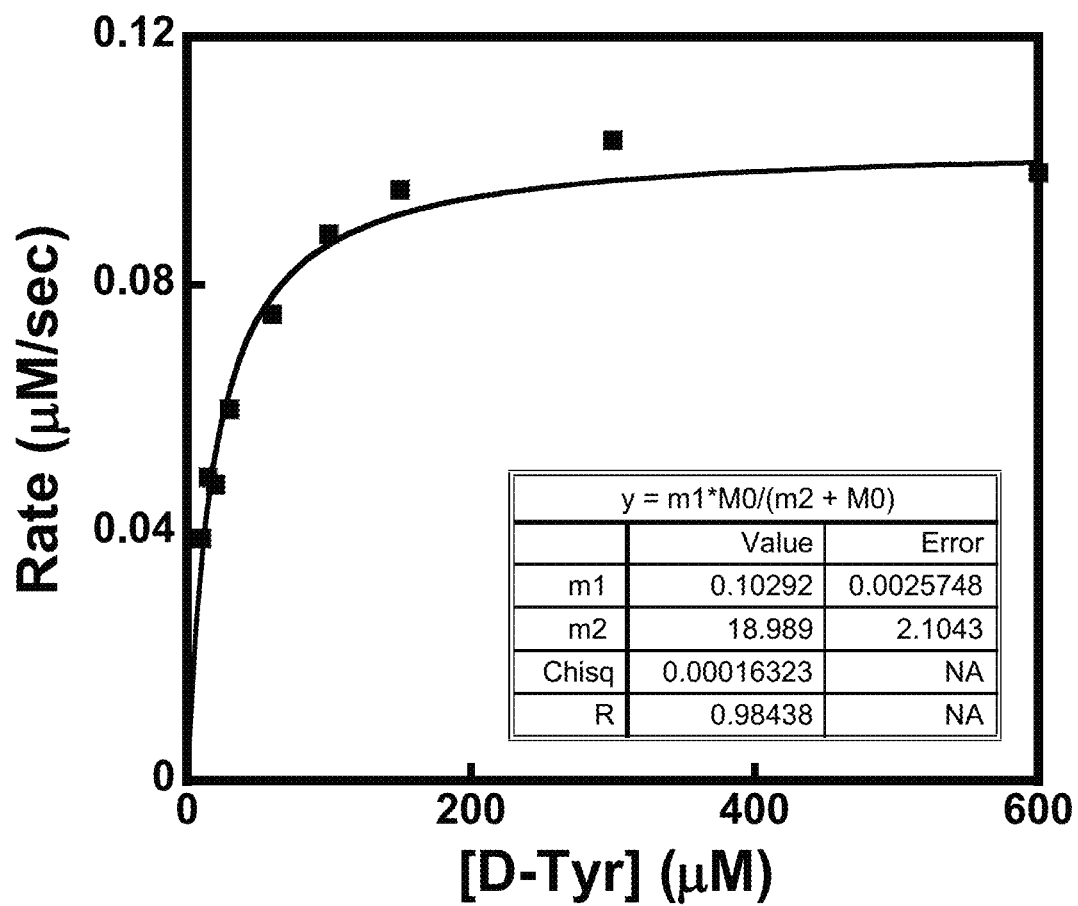
Figure 24:
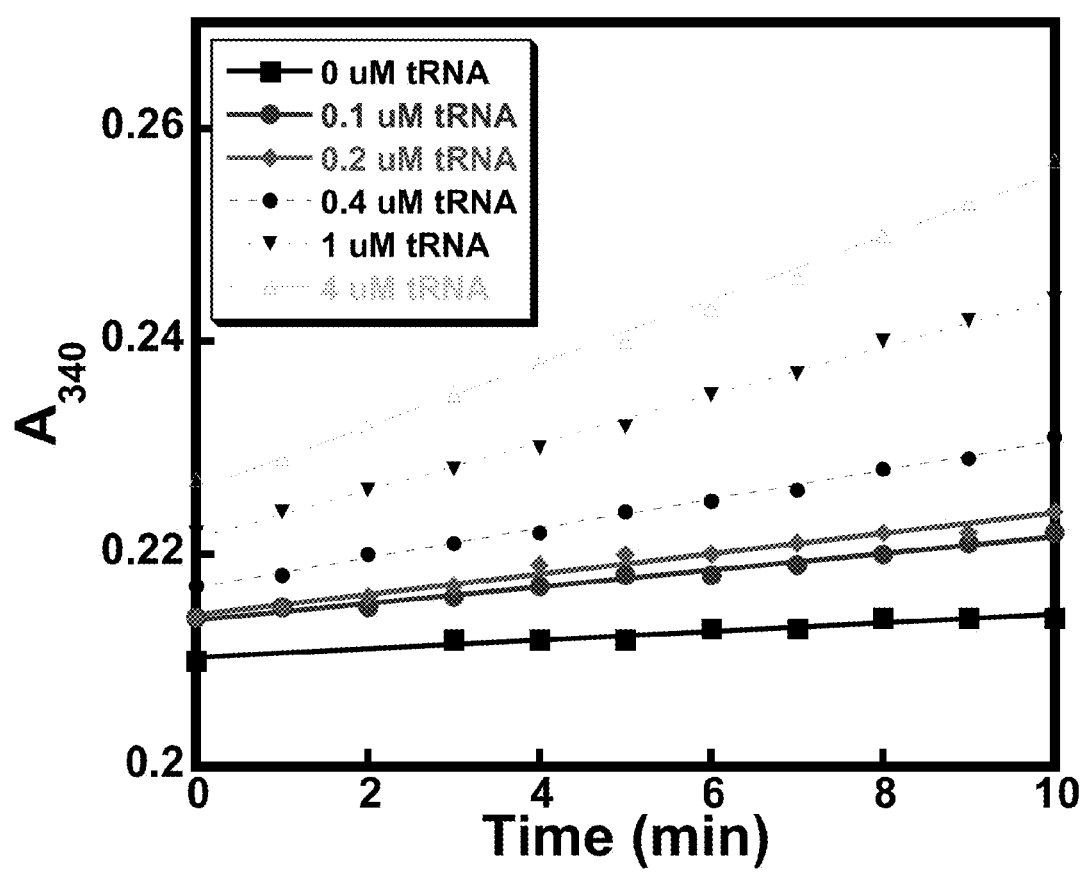
Figure 25:
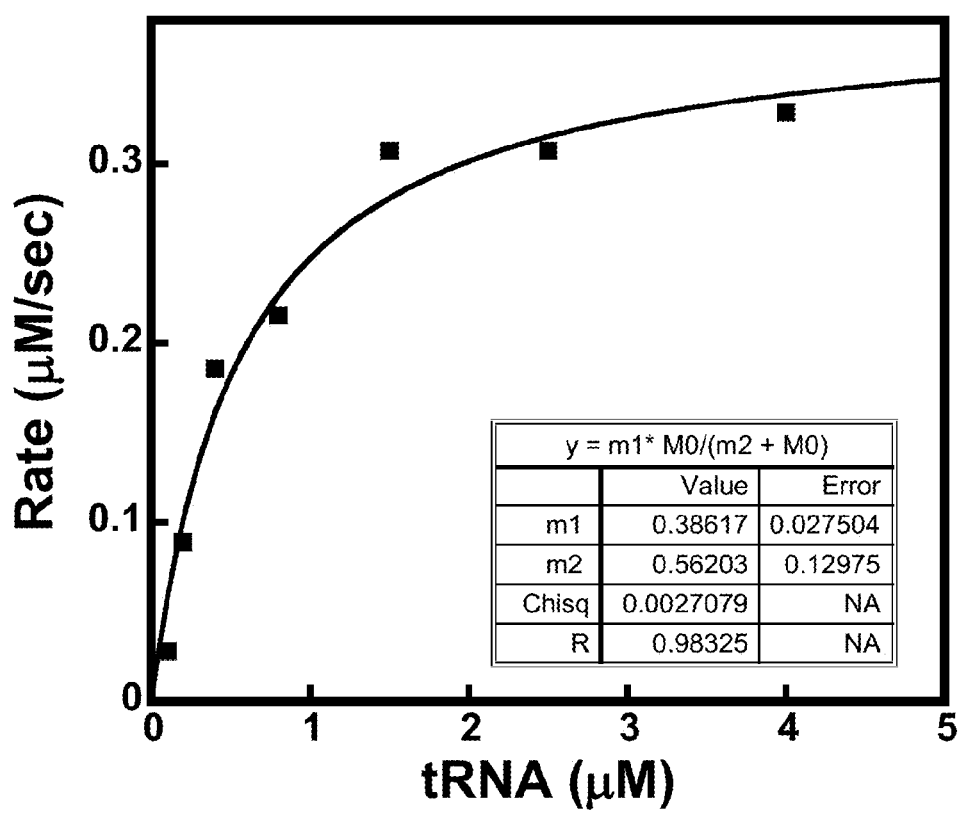

To determine the $K_m^{D-Tyr}$, $K_m^{tRNA}$, and $k_{cat}$ values for *G. stearothermophilus* tyrosyl-tRNA synthetase when D-tyrosine is the substrate, the reaction rate was determined at varying concentrations of either D-tyrosine or tRNA$^{Tyr}$ using 10 mM MgATP and saturating concentrations of either D-tyrosine or tRNA$^{Tyr}$, shown in FIGS. 22 and 24. Under these conditions, $K_m^{D-Tyr}$ and $K_m^{tRNA}$ measure the affinity of D-tyrosine and tRNA$^{Tyr}$ for the TyrRS.ATP.tRNA and TyrRS.Tyr-AMP complexes, respectively. As was the case for L-tyrosine, the aminoacylation of tRNA$^{Tyr}$ by D-tyrosine follows classical Michaelis-Menten kinetics with respect to both the D-tyrosine and tRNA$^{Tyr}$ substrates, shown in FIGS. 23 and 25. The values for $K_m^{D-TYr}$, $K_m^{tRNA}$, and $k_{cat}$ are summarized in Table 2, above. Surprisingly, $K_m^{D-TYr}$ is 8-fold lower than the value of $K_d^{D-TYr}$ determined by single turnover kinetics. One difference between the two assays is that the single turnover assay monitored formation of the enzyme-bound tyrosyl-adenylate intermediate in the absence of tRNA$^{Tyr}$. It is possible that the binding of tRNA$^{Tyr}$ stabilizes an enzyme conformation that binds D-tyrosine with a higher affinity.

Figure 26:
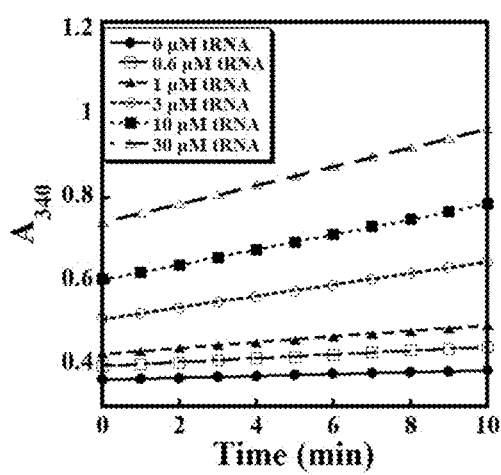
FIGS. 26-29 show monitoring the activities of cyclodityrosine synthase and D-tyrosyl-tRNA deacylase. Typical initial rate and substrate-dependence curves for *M. tuberculosis* cyclodityrosine synthase and *T. thermophilus* D-tyrosyl-tRNA deacylase are shown. Cyclodityrosine synthase and D-tyrosyl-tRNA deacylase activities were monitored by following the increase in absorbance at 340 nm.
Figure 27:
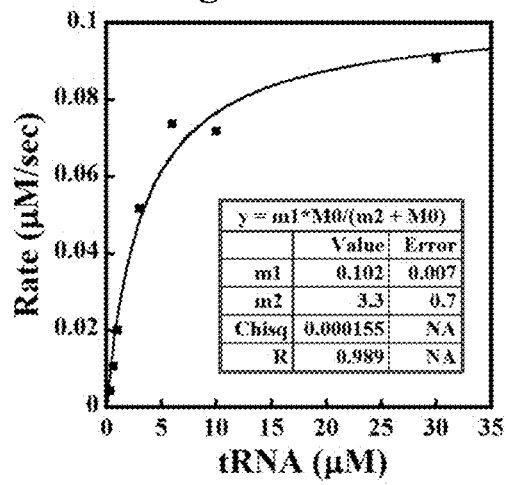

Monitoring cyclodityrosine synthase activity via the release of AMP—The tyrosyl-tRNA synthetase assay can be adapted to monitor the activity of cyclodityrosine synthase by increasing the concentration of tyrosyl-tRNA synthetase and/or decreasing the cyclodityrosine synthase concentration such that formation of cyclodityrosine becomes the rate-limiting step. To ensure that cyclodityrosine synthase is the rate-limiting enzyme, the assay was performed in the presence of 5 µM tyrosyl-tRNA synthetase and 0.05 µM cyclodityrosine synthase. To determine the $K_m^{L-Tyr-RNA}$ and $k_{cat}$ values for cyclodityrosine synthase, the initial rate of the reaction was determined in the presence of 10 mM MgATP, 0.3 mM L-tyrosine, and varying concentrations of tRNA$^{Tyr}$ and the initial rates were plotted as a function of tRNA concentration (FIG. 26). Under these conditions, L-Tyr-tRNA is formed in situ, making the reaction rate dependent on the binding of L-Tyr-tRNA and cleavage of the aminoacyl-tRNA bond. As a result, the $K_m$ determined by varying the tRNA$^{Tyr}$ concentration is a measure of the affinity of L-Tyr-tRNA$^{Tyr}$ for cyclodityrosine synthase (i.e., $K_m^{L-Tyr-tRNA}$.) Plotting the initial rate against the tRNA concentration indicates that cyclodityrosine synthase follows classical Michaelis-Menten kinetics with respect to the Tyr-tRNA substrate (FIG. 27). The values for $K_m^{L-Tyr-tRNA}$ and $k_{cat}$ are 3 (±1) µM and 2.2 (±0.1) 5$^{-1}$ respectively, and are similar to previously reported values for cyclodityrosine synthase (3.6 µM and 2.5 s$^{-1}$, respectively).

Figure 28:
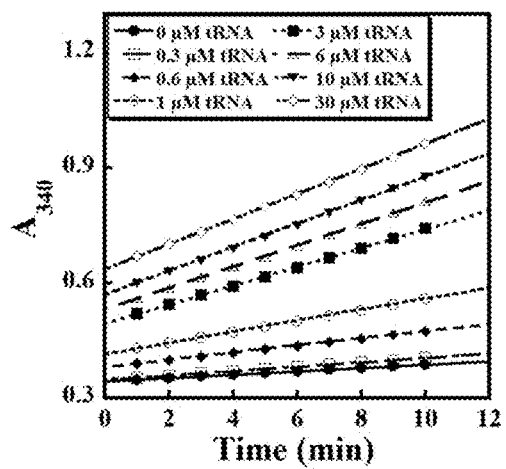
Figure 29:
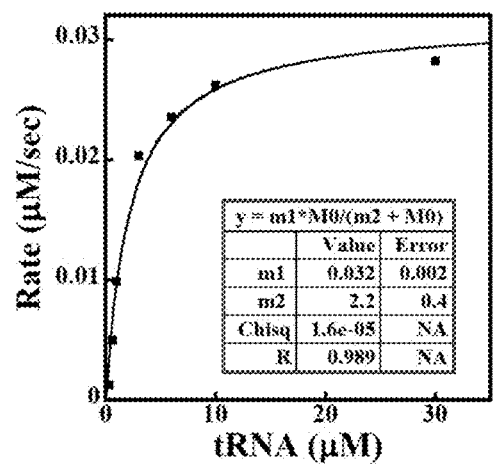

Monitoring D-tyrosyl-tRNA deacylase activity via the release of AMP—The tyrosyl-tRNA synthetase assay can be adapted to monitor the activity of D-tyrosyl-tRNA deacylase by increasing the concentration of tyrosyl-tRNA synthetase and/or decreasing the D-tyrosyl-tRNA deacylase concentration such that hydrolysis of D-tyrosyl-tRNA is the rate-limiting step. To ensure that D-tyrosyl-tRNA deacylase is the rate-limiting enzyme, the assay was performed in the presence of 1 µM tyrosyl-tRNA synthetase and 5 µM D-tyrosyl-tRNA deacylase. To determine the $K_m^{D-Tyr-RNA}$ and $k_{cat}$ values for *T. thermophilus* D-tyrosyl-tRNA deacylase, the reaction rate was determined in the presence of 10 mM MgATP, 0.3 mM D-tyrosine, and varying concentrations of tRNA$^{Tyr}$ (FIG. 28). Under these conditions, D-Tyr-tRNA is formed in situ, and the $K_m$ determined by varying the tRNA$^{Tyr}$ concentration is equivalent to $K_m^{D-Tyr-tRNA}$. Hydrolysis of D-Tyr-tRNA$^{Tyr}$ by D-tyrosyl-tRNA deacylase follows classical Michaelis-Menten kinetics (FIG. 29). The $K_m^{D-TYr-tRNA}$ value is 2.2 (±0.2)µM, which is similar to the previously reported value of 1 µM for the $K_m^{D-Tyr-tRNA}$ of *Escherichia coli* D-tyrosyl-tRNA deacylase. In contrast, the $k_{cat}$ value for *T. thermophilus* D-tyrosyl-tRNA deacylase is 0.026 (±0.002) s$^{-1}$, which is over 200-fold less than the $k_{cat}$ for *E. coli* D-tyrosyl-tRNA synthetase. *T. thermophilus* is a Gram negative bacterium whose optimal growth temperature is approximately 65° C. It is likely that the low activity of *T. thermophilus* D-tyrosyl-tRNA deacylase at 25° C. either reflects its adaptation to higher temperatures, or is due to the amino-terminal S-tag/His-tag interfering with its catalytic activity Discussion: aminoacyl-tRNA synthetase assay. Advantages of recycling the tRNA substrate—The inventors disclose herein a homogenous, continuous, spectrophotometric assay for monitoring tyrosyl-tRNA synthetase activity that can be used for both steady state kinetic analyses and high-throughput screening of chemical libraries. This aminoacyl-tRNA synthetase assay takes advantage of a method that couples the production of AMP to the reduction of NAD$^+$, resulting in a concomitant increase in absorbance at 340, described above. In addition, the tyrosyl-tRNA synthetase assay described here is unique in the art in that the tRNA$^{Tyr}$ substrate is regenerated with each turnover of the enzyme. As tRNA$^{Tyr}$ is the limiting substrate in the assay, regenerating it in situ has a number of benefits. First, it requires significantly less tRNA, substantially reducing the cost of the assay. Second, since tRNA is no longer the limiting substrate, the aminoacylation reaction will proceed for a longer time, generating more NADH and increasing the signal:noise ratio. Third, it allows subsaturating concentrations of tRNA to be used, making it possible to determine the $K_m$ value for tRNA and making it feasible to screen for competitive inhibitors of tRNA. Lastly, the approach to regenerating the tRNA substrate described here can be applied to other aminoacyl-tRNA synthetase assays. For example, several aminoacyl-tRNA synthetase assays use the release of pyrophosphate and its subsequent cleavage by inorganic pyrophosphatase to monitor activity, such as those described in A. J. Lloyd, H. U. Thomann, M. Ibba, D. Soll, "A broadly applicable continuous spectrophotometric assay for measuring aminoacyl-tRNA synthetase activity," Nucleic Acids Research, 23 (1995) 2886-2892, and I. Cestari, K. Stuart, "A spectrophotometric assay for quantitative measurement of aminoacyl-tRNA synthetase activity," *Journal of Biomolecular Screening*, 18 (2013) 490-497. Adding an enzyme that cleaves the aminoacyl-tRNA product would prevent tRNA from being the limiting substrate in these assays.

Expanding the tyrosyl-tRNA synthetase assay to other aminoacyl-tRNA synthetases—In contrast to D-tyrosyl-tRNA deacylase, which exhibits broad substrate specificity with respect to D-aminoacyl-tRNAs, cyclodityrosine synthase is highly specific, recognizing only L-tyrosyl-tRNA as a substrate. To expand the tyrosyl-tRNA synthetase assay to other aminoacyl-tRNA synthetases, cyclodityrosine synthase must be replaced by an enzyme that cleaves the appropriate aminoacyl-tRNA product. One way to do this is to replace cyclodityrosine synthase with enzymes that cleave specific aminoacyl-tRNAs. In other words, each aminoacyl-tRNA synthetase assay would have and potentially require a unique enzyme to regenerate the tRNA substrate. Enzymes that cleave specific aminoacyl-tRNAs include cyclodipeptide synthases, trans-editing proteins, and aminoacyl-tRNA synthetase editing domains (or catalytically inactive aminoacyl-tRNA synthetases that contain active editing domains). Examples of these three classes are described below. While all three classes of enzymes will cleave the aminoacyl-tRNA bond, regenerating the tRNA substrate, they differ in that cyclodipeptide synthases release a cyclic dipeptide, whereas aminoacyl-tRNA synthetase editing domains release the free amino acid. The latter may be advantageous if low amino acid concentrations are to be used in the assay. In contrast, cyclodipeptide synthases would be beneficial when it is disadvantageous to regenerate the free amino acid. For example, the activity of methionine synthase, which catalyzes the conversion of L-homocysteine to L-methionine, could be monitored by coupling it to the aminoacylation of $tRNA^{Met}$ by methionyl-tRNA synthetase. In this case, one would not want to use an enzyme that regenerates both $tRNA^{Met}$ and L-methionine since it would uncouple the methionine synthase catalyzed reaction from the aminoacylation of $tRNA^{Met}$.

An alternative approach to expanding the tyrosyl-tRNA synthetase assay is to use an enzyme that non-specifically hydrolyzes aminoacyl-tRNAs. This is the approach that was taken to monitor the aminoacylation of $tRNA^{Tyr}$ by D-tyrosine, as D-tyrosyl-tRNA deacylase is relatively nonspecific with respect to the aminoacyl moiety in the D-aminoacyl-tRNA substrate. Based on the structural comparison of *E. coli* D-tyrosyl-tRNA deacylase and the homologous editing domain of *Pyrococcus abyssi* threonyl-tRNA synthetase, Hussain et al. postulated that replacing methionine 129 with lysine in D-tyrosyl-tRNA deacylase would result in recognition of both D-and L-aminoacyl-tRNAs. T. Hussain, V. Kamarthapu, S. P. Kruparani, M. V. Deshmukh, R. Sankaranarayanan, "Mechanistic insights into cognate substrate discrimination during proofreading in translation," *Proceedings of the National Academy of Sciences of the United States of America*, 107 (2010) 22117-22121. These authors tested this hypothesis and found that the M129K variant of D-tyrosyl-tRNA deacylase hydrolyzes both L- and D-seryl-tRNA and recognizes 11 additional L- and D-amino acids, as well as glycine. This evidences that replacing cyclodityrosine synthase with the D-tyrosyl-tRNA deacylase M129K variant would allow the novel tyrosyl-tRNA synthetase assay disclosed herein to be used to monitor the activity of at least 12 different aminoacyl-tRNA synthetases. See Table 3 below.

Monitoring cyclodityrosine synthase and D-tyrosyl-tRNA deacylase activity—In addition to monitoring tyrosyl-tRNA synthetase activity, the inventors disclosed that the assay described here can be used to monitor the activities of cyclodityrosine synthase and D-tyrosyl-tRNA deacylase by adjusting the reaction conditions such that cleavage of Tyr-tRNA is the rate-limiting step in the assay. A related, but deficient approach has previously been used to generate aminoacyl-tRNA substrates for cyclodityrosine synthase and AlbC in situ prior to end point analysis of the AlbC reaction products by HPLC and mass spectrometry, respectively (AlbC catalyzes the formation of cyclo[L-Leu-L-Phe]). D-tyrosyl-tRNA deacylase activity has previously been analyzed by monitoring the release of [$^3$H]-labeled amino acids from D-aminoacyl-tRNAs. The cyclodityrosine synthase and D-tyrosyl-tRNA deacylase assays disclosed herein, by comparison, are less expensive and (in the case of the D-tyrosyl-tRNA deacylase assay) safer than those currently known. The cyclodityrosine synthase and D-tyrosyl-tRNA deacylase assays disclosed herein are suitable for both high-throughput screening of inhibitors and their subsequent kinetic analyses.

Cyclodityrosine synthase is found in *Mycobacterium tuberculosis* and closely related species. One third of the world's population is infected with *Mycobacterium tuberculosis*, the causative agent of tuberculosis, with new infections occurring in ~1% of the population per year. In *M. tuberculosis*, cyclodityrosine is converted to mycocyclosin—a putative siderophore—by the actions of the cytochrome P450 CYP121. Deletion of Rv2276—the gene encoding CYP121—is lethal, suggesting that CYP121 may represent a novel antibiotic target in *M. tuberculosis*. While the lethality of the Rv2276 deletion may be due to either the essential nature of mycocyclosin or the accumulation of cyclodityrosine, the observation that cyclodityrosine synthase can be expressed in *E. coli* suggests that the accumulation of cyclodityrosine is not toxic to bacterial cells. This implies that, like CYP121, cyclodityrosine synthase represents a potential antibiotic target in *M. tuberculosis*.

Unlike cyclodityrosine synthase, D-tyrosyl-tRNA deacylase is a nearly ubiquitous enzyme in bacteria, archaea, and eukaryotes. Deletion of D-tyrosyl-tRNA deacylase from *E. coli* and *S. cerevisiae* results in the accumulation of D-aminoacyl-tRNAs, depleting the available pool of free tRNA and impairing cell growth. This suggests that bacterial, fungal, and protozoan D-tyrosyl-tRNA deacylases represent novel antimicrobial and antiparasitic targets, while human D-tyrosyl-tRNA deacylase is a potential target for chemotherapy agents.

Monitoring post-translational editing by aminoacyl-tRNA synthetases—A number of aminoacyl-tRNA synthetases use editing mechanisms to increase the fidelity of the tRNA aminoacylation reaction. Removal of the noncognate aminoacyl moiety involves hydrolysis of either the aminoacyl-adenylate intermediate (pre-transfer editing) or the aminoacyl-tRNA product (post-transfer editing). The proposal to use editing domains to regenerate the tRNA substrate implies that the aminoacyl-tRNA synthetase assay can be used to monitor post-transfer editing activity by making cleavage of the aminoacyl-tRNA by the editing domain the rate-limiting step in the reaction. This can be done by combining an editing defective aminoacyl-tRNA synthetase—which generates aminoacyl-tRNA but does not cleave it—with either the wild type aminoacyl-tRNA synthetase or a catalytically inactive aminoacyl-tRNA synthetase that has a functional editing site. By adjusting the ratio of the editing to non-editing aminoacyl-tRNA synthetases, the editing of the aminoacyl-tRNA product can be made the rate-limiting step. This is analogous to the approach disclosed herein to monitor cyclodityrosine synthase and D-tyrosyl-tRNA deacylase activity. Based on the novel methods disclosed herein, similar assays can be designed to monitor the activities of trans-editing proteins (e.g. Ybak, AlaX) and other enzymes that use aminoacyl-tRNA as substrates (e.g. Fem ligases, MprF).

Concluding Remarks: aminoacyl-tRNA synthetase assay. A homogenous, continuous, spectrophotometric assay has been developed to monitor tyrosyl-tRNA synthetase activity. This assay can be used with either L- or D-tyrosine and is suitable for both kinetic analyses and high-throughput drug screening. By making Tyr-tRNA cleavage the rate-limiting step, this assay can also be used to monitor cyclodityrosine synthase and D-tyrosyl-tRNA deacylase activity. This assay may be extended to monitor the catalytic and editing activities of other aminoacyl-tRNA synthetases.

Cleaving Enzymes: Aminoacyl-tRNA synthetases catalyze the attachment of amino acids to their cognate tRNAs. In general, aminoacyl-tRNA synthetase assays require stoichiometric amounts of tRNA, which limits their sensitivity while increasing their cost. This requirement for stoichiometric amounts of tRNA can be alleviated if the aminoacyl-tRNA product is cleaved following the tRNA aminoacylation reaction, regenerating the free tRNA substrate, as described above. The inventors now disclose enzymes that cleave the aminoacyl-tRNA product for at least 15 of the 20 naturally occurring amino acids. These enzymes extend the tyrosyl-tRNA synthetase assay to other aminoacyl-tRNA synthetases.

Cleaving Enzymes: Data, Experimental Design, Materials and Methods. Aminoacyl-tRNA synthetases (aaRSes) are essential enzymes that catalyze the attachment of amino acids to their cognate tRNAs using a two-step mechanism. The two step reaction mechanism for the aminoacylation of tRNA is shown below:

Activation of the Amino Acid

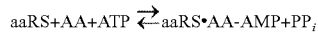

Transfer of the Aminoacyl Moiety to tRNA

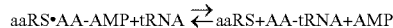

In the first step, the amino acid is activated by ATP, forming an enzyme-bound aminoacyl-adenylate intermediate (aaRS•AA-AMP). In the second step of the reaction, the activated aminoacyl-moiety is transferred to the 3' end of the cognate tRNA, resulting in the release of the aminoacyl-tRNA and AMP products. 'aaRS', AA, and $PP_i$ represent aminoacyl-tRNA synthetase, amino acid, and inorganic pyrophosphate, respectively. Noncovalent interactions are indicated by '•' and covalent bonds are indicated by '-'.

The inventors disclosed a continuous spectrophotometric assay for one of the aminoacyl-tRNA synthetases, tyrosyl-tRNA synthetase, in which the release of AMP is coupled to the production of NADH via AMP deaminase (which converts AMP to IMP) and IMP dehydrogenase (which couples the oxidation of $NAD^+$ to the reduction of IMP). As the production of NADH is associated with an increase in absorbance at 340 nm, the aminoacylation of $tRNA^{Tyr}$ by tyrosine can be monitored spectrophotometrically. In contrast to other aminoacyl-tRNA synthetase assays, where tRNA is the limiting substrate, in the tyrosyl-tRNA synthetase assay, the Tyr-$tRNA^{Tyr}$ product is cleaved, regenerating the $tRNA^{Tyr}$ substrate. This results in a substantial increase in the sensitivity of the assay, while significantly decreasing its cost. The inventors have demonstrated that the tyrosyl-tRNA synthetase assay can be used to monitor the aminoacylation of tRNA by either L- or D-tyrosine, with cyclodityrosine synthase and D-tyrosyl-tRNA deacylase being used to cleave the L-Tyr-tRNA and D-Tyr-tRNA products, respectively.

In order to extend the tyrosyl-tRNA synthetase assay to other aminoacyl-tRNA synthetases, the inventors have identified aminoacyl-tRNA synthetase editing domains, trans-editing proteins, and cyclodipeptide synthases that can be used to cleave specific aminoacyl-tRNA products. In addition, based on published literature, the inventors have identified variants of editing domains and proteins that increase the number of different aminoacyl-tRNAs that the editing domains and proteins can cleave. This allows them to regenerate the tRNA substrate for several different aminoacyl-tRNA synthetases.

Figure 30:
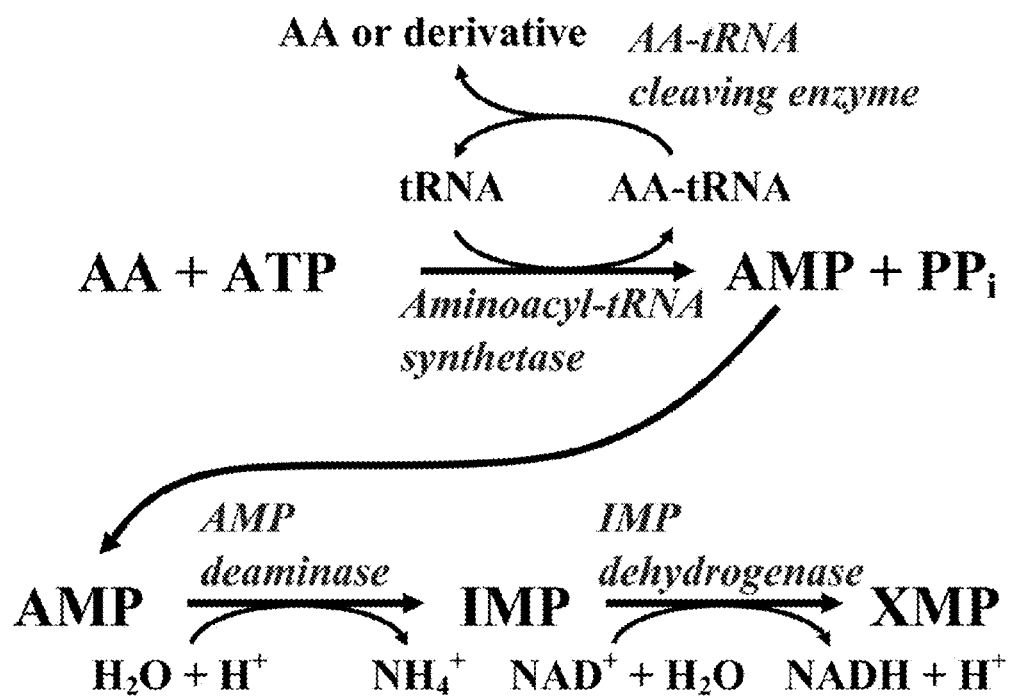
FIG. 30 is the reaction scheme for the aminoacyl-tRNA synthetase assay. The aminoacylation of tRNA is monitored by coupling the release of AMP to the production of NADH via the actions of AMP deaminase and IMP dehydrogenase. Under conditions where tRNA aminoacylation is the rate-limiting step (i.e., at sufficiently low concentrations of the aminoacyl-tRNA synthetase), the rate of the reaction will correspond to the increase in absorbance at 340 nm with respect to time. Cleavage of the aminoacyl-tRNA (AA-tRNA) product by an aminoacyl-tRNA editing protein or cyclodipeptide synthase, regenerates the unliganded tRNA, preventing it from being the limiting substrate in the reaction. AMP, IMP, XMP, PP$_i$, and AA represent adenosine 5'-monophosphate, inosine 5'-monophosphate, xanthine 5'-monophosphate, inorganic pyrophosphate, and amino acid, respectively.

The basic aminoacyl-tRNA synthetase assay is shown in FIG. 30. Aminoacylation of tRNA results in the release of the aminoacyl-tRNA product, AMP, and inorganic pyrophosphate ($PP_i$). The inventors have coupled the production of AMP to the oxidation of $NAD^+$, allowing the assay to be followed by monitoring changes in absorbance at 340 nm ($\epsilon_{340}^{NADH}$=6220 $M^{-1}$ $cm^{-1}$). Alternatively, the reaction can be followed by using inorganic pyrophosphatase to cleave the inorganic pyrophosphate product and monitoring the resulting production of phosphate (e.g. via reaction with malachite green and ammonium molybdate). Cleavage of the aminoacyl-tRNA product is achieved by using an editing domain, trans-editing protein, or cyclodipeptide synthase that is specific for each particular aminoacyl-tRNA, or by using the M129K variant of D-tyrosyl-tRNA deacylase, which catalyzes the hydrolysis of both L- and D-aminoacyl-tRNAs and has a broad specificity with respect to the aminoacyl moiety. See Table 3 below. In the event that a particular editing domain cannot be isolated in its active form, a variant of the full length aminoacyl-tRNA synthetase in which the synthetic site has been inactivated can be used to hydrolyze the aminoacyl-tRNA product.

TABLE 3

Proteins that regenerate free tRNA

| Protein[1] | Substrate specificity[2] | Literature Reference |
|---|---|---|
| AlaRS editing domain[3] | L-Ser-tRNA, Gly-tRNA | [1, 2] |
| IleRS editing domain[3] | L-Val-tRNA | [3, 4] |
| ValRS editing domain[3] | L-Thr-tRNA | [3] |
| LeuRS editing domain[3] | L-Ile-tRNA, L-Met-tRNA, L-Nva-tRNA | [6, 7] |
| LeuRS-T252A editing domain[3] | L-Ile-tRNA, L-Met-tRNA, L-Nva-tRNA, L-Leu-tRNA | [8, 9] |
| ThrRS editing domain[3] | L-Ser-tRNA | [10] |
| ProRS editing domain[3] | L-Ala-tRNA | [11] |
| PheRS editing domain[3] | L-Tyr-tRNA | [14] |
| Ybak protein[4] | L-Cys-tRNA | [15] |

TABLE 3-continued

Proteins that regenerate free tRNA

| Protein[1] | Substrate specificity[2] | Literature Reference |
|---|---|---|
| ProXP-Ala protein[4] | L-Ala-tRNA | [16] |
| AlaX protein[4] | L-Ser-tRNA, Gly-tRNA | [1] |
| PrdX protein[4] | L-Ala-tRNA | [1] |
| ThrRS-ed protein[4] | L-Ser-tRNA | [17] |
| D-tyrosyl-tRNA deacylase (DTD)[4] | D-aminoacyl-tRNA | [18, 19] |
| D-tyrosyl-tRNA deacylase M129K variant (DTD-M129K)[5] | L-Ala-tRNA, L-Asp-tRNA, L-Arg-tRNA, L-Cys-tRNA, Gly-tRNA, L-Glu-tRNA, L-Phe-tRNA, L-Pro-tRNA, L-Ser-tRNA, L-Thr-tRNA, L-Tyr-tRNA, L-Leu-tRNA, L-Val-tRNA | [20] |
| AlbC[6] | L-Phe-tRNA | [21] |
| Cyclodityrosine synthase[6] | L-Tyr-tRNA | [22] |
| YvmC[6] | L-Leu-tRNA | [23] |

[1]aminoacyl-tRNA synthetases are abbreviated using the 3-letter code for the amino acid, followed by 'RS'
[2]standard 3-letter codes are used for each aminoacyl-tRNA, Nva is the 3-letter code for norvaline
[3]indicates the activity of the editing domain in the protein
[4]indicates a naturally occurring trans-editing protein
[5]only hydrolysis of L-Ser-tRNA has been demonstrated for the M129K variant of DTD, hydrolysis of other L-aminoacyl-tRNAs is assumed based on the ability of the DTD-M129K variant to bind the free L-amino acids
[6]indicates a cyclodipeptide synthase, which releases the free tRNA along with a cyclic dipeptide References to Table 3:
[1] I. Ahel, D. Korencic, M. Ibba, D. Soll, Trans-editing of mischarged tRNAs, Proceedings of the National Academy of Sciences of the United States of America, 100 (2003) 15422-15427
[2] W. C. Tsui, A. R. Fersht, Probing the principles of amino acid selection using the alanyl-tRNA synthetase from *Escherichia coli*, Nucleic acids research, 9 (1981) 4627-4637.
[3] A. R. Fersht, Editing mechanisms in protein synthesis. Rejection of valine by the isoleucyl-tRNA synthetase, Biochemistry, 16 (1977) 1025-1030.
[4] H. Jakubowski, A. R. Fersht, Alternative pathways for editing non-cognate amino acids by aminoacyl-tRNA synthetases, Nucleic acids research, 9 (1981) 3105-3117.
[6] J. F. Chen, N. N. Guo, T. Li, E. D. Wang, Y. L. Wang, CP1 domain in *Escherichia coli* leucyl-tRNA synthetase is crucial for its editing function, Biochemistry, 39 (2000) 6726-6731.
[7] S. Englisch, U. Englisch, F. von der Haar, F. Cramer, The proofreading of hydroxy analogues of leucine and isoleucine by leucyl-tRNA synthetases from *E. coli* and yeast, Nucleic acids research, 14 (1986) 7529-7539.
[8] R. S. Mursinna, K. W. Lee, J. M. Briggs, S. A. Martinis, Molecular dissection of a critical specificity determinant within the amino acid editing domain of leucyl-tRNA synthetase, Biochemistry, 43 (2004) 155-165.
[9] R. S. Mursinna, T. L. Lincecum, Jr., S. A. Martinis, A conserved threonine within *Escherichia coli* leucyl-tRNA synthetase prevents hydrolytic editing of leucyl-tRNALeu, Biochemistry, 40 (2001) 5376-5381.
[10] A. Dock-Bregeon, R. Sankaranarayanan, P. Romby, J. Caillet, M. Springer, B. Rees, C. S. Francklyn, C. Ehresmann, D. Moras, Transfer RNA-mediated editing in threonyl-tRNA synthetase. The class II solution to the double discrimination problem, Cell, 103 (2000) 877-884.
[11] P. J. Beuning, K. Musier-Forsyth, Species-specific differences in amino acid editing by class II prolyl-tRNA synthetase, The Journal of biological chemistry, 276 (2001) 30779-30785.
[14] H. Roy, J. Ling, M. Irnov, M. Ibba, Post-transfer editing in vitro and in vivo by the beta subunit of phenylalanyl-tRNA synthetase, The EMBO journal, 23 (2004) 4639-4648.
[15] H. Zhang, K. Huang, Z. Li, L. Banerjei, K. E. Fisher, N. V. Grishin, E. Eisenstein, O. Herzberg, Crystal structure of YbaK protein from *Haemophilus influenzae* (HI1434) at 1.8 A resolution: functional implications, Proteins, 40 (2000) 86-97.
[16] O. Vargas-Rodriguez, K. Musier-Forsyth, Exclusive use of trans-editing domains prevents proline mistranslation, The Journal of biological chemistry, 288 14391-14399.
[17] D. Korencic, I. Ahel, J. Schelert, M. Sacher, B. Ruan, C. Stathopoulos, P. Blum, M. Ibba, D. Soll, A freestanding proofreading domain is required for protein synthesis quality control in Archaea, Proceedings of the National Academy of Sciences of the United States of America, 101 (2004) 10260-10265.
[18] R. Calendar, P. Berg, D-Tyrosyl RNA: formation, hydrolysis and utilization for protein synthesis, Journal of molecular biology, 26 (1967) 39-54.
[19] J. Soutourina, P. Plateau, F. Delort, A. Peirotes, S. Blanquet, Functional characterization of the D-Tyr-tRNATyr deacylase from *Escherichia coli*, The Journal of biological chemistry, 274 (1999) 19109-19114.
[20] T. Hussain, V. Kamarthapu, S. P. Kruparani, M. V. Deshmukh, R. Sankaranarayanan, Mechanistic insights into cognate substrate discrimination during proofreading in translation, Proceedings of the National Academy of Sciences of the United States of America, 107 (2010) 22117-22121.
[21] M. Gondry, L. Sauguet, P. Belin, R. Thai, R. Amouroux, C. Tellier, K. Tuphile, M. Jacquet, S. Braud, M. Courcon, C. Masson, S. Dubois, S. Lautru, A. Lecoq, S. Hashimoto, R. Genet, J. L. Pernodet, Cyclodipeptide synthases are a family of tRNA-dependent peptide bond-forming enzymes, Nature chemical biology, 5 (2009) 414-420.
[22] M. W. Vetting, S. S. Hegde, J. S. Blanchard, The structure and mechanism of the *Mycobacterium tuberculosis* cyclodityrosine synthetase, Nature chemical biology, 6 (2010) 797-799.
[23] L. Bonnefond, T. Arai, Y. Sakaguchi, T. Suzuki, R. Ishitani, 0. Nureki, Structural basis for nonribosomal peptide synthesis by an aminoacyl-tRNA synthetase paralog, Proceedings of the National Academy of Sciences of the United States of America, 108 (2011) 3912-3917.

Further Applications: Based on the novel methods and assays disclosed, the inventors have developed even further applications as follow.

As shown in FIG. 1, and described above, the inventors disclose a method to monitor the production of AMP by coupling it to the conversion of $NAD^+$ to NADH.

Figure 2:
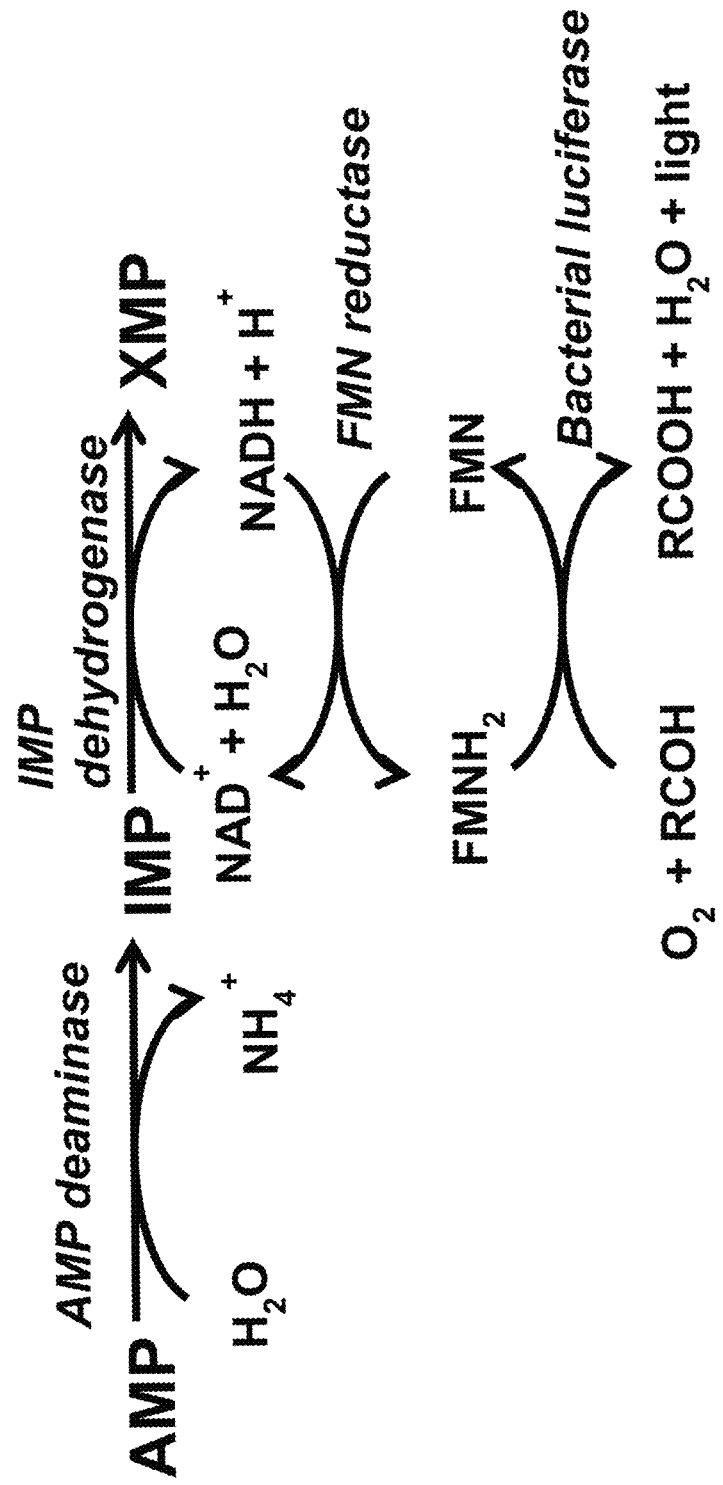
FIG. 2 is a reaction scheme for assay to monitor the production of AMP by coupling it to the oxidation of a low molecular weight aldehyde by bacterial luciferase. Oxidation of the low molecular weight aldehyde (e.g. decanal) is monitored by measuring the production of light released by the bacterial luciferase.
Figure 3:
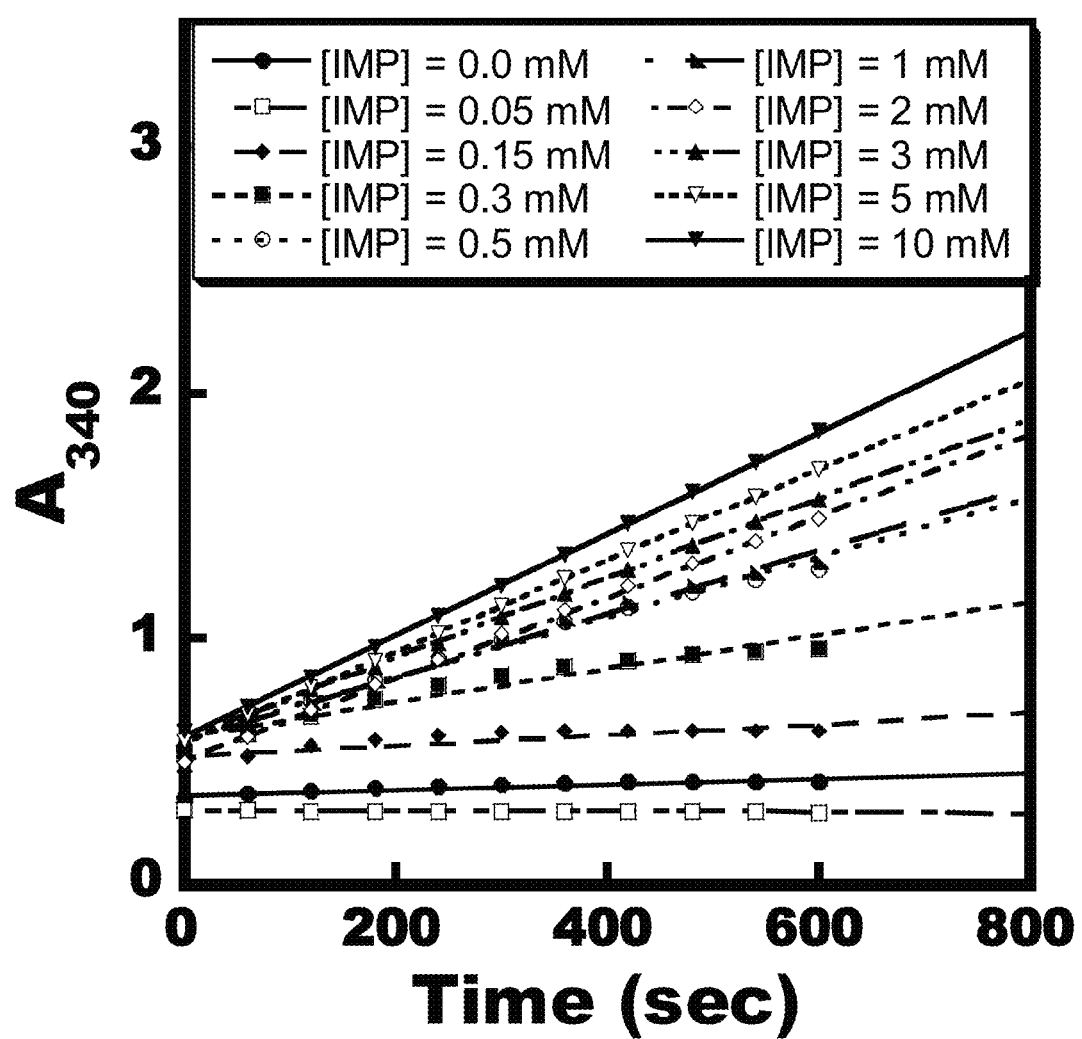
FIGS. 3-6 show monitoring IMP dehydrogenase activity by the production of NADH. IMP dehydrogenase activity was monitored by following the increase in absorbance at 340 nm.
Figure 4:
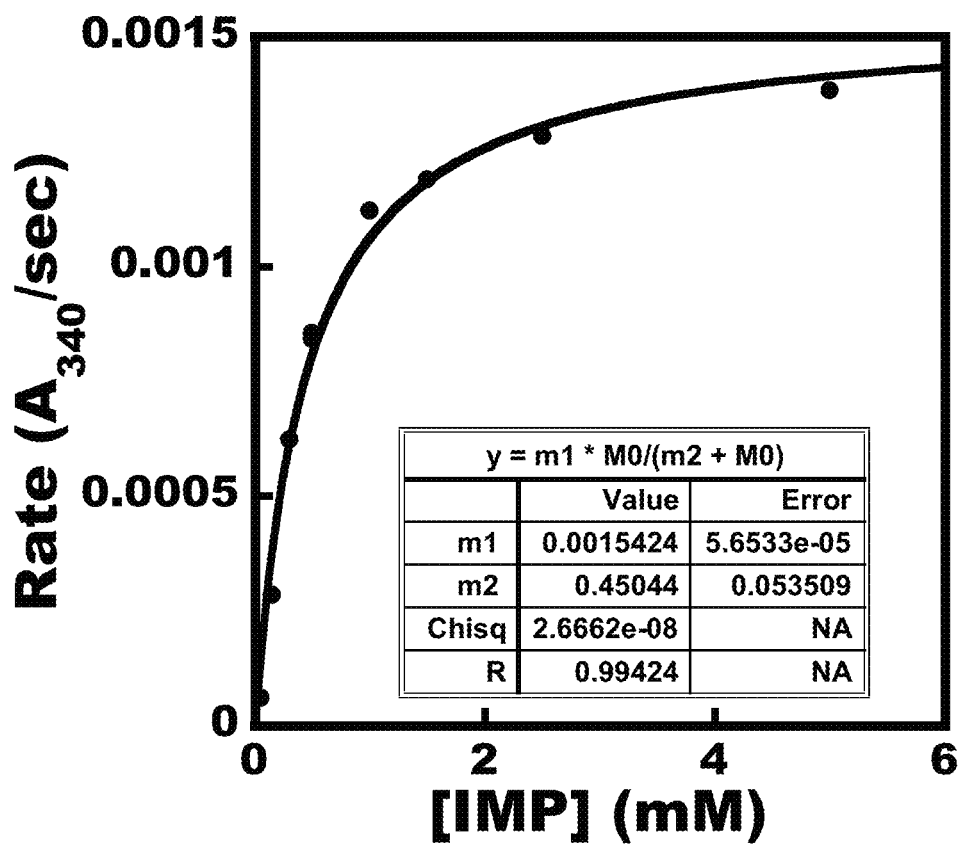
Figure 5:
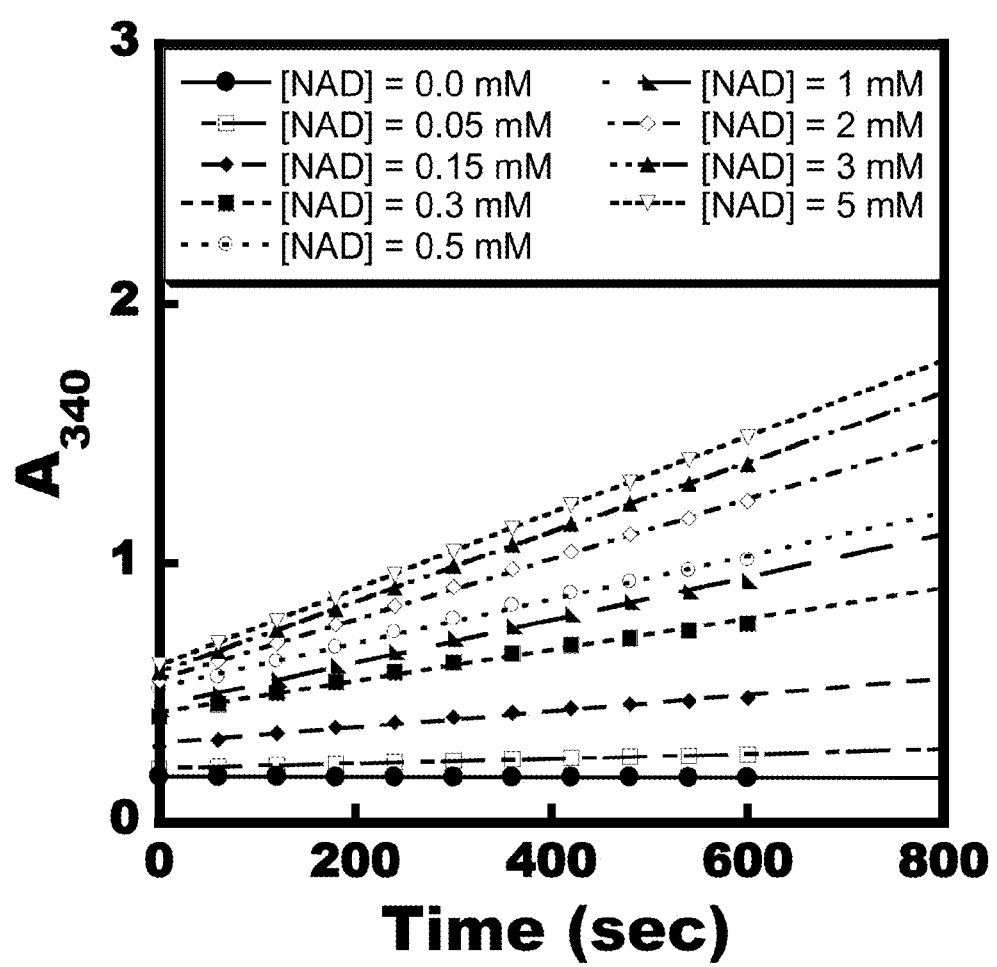
Figure 6:
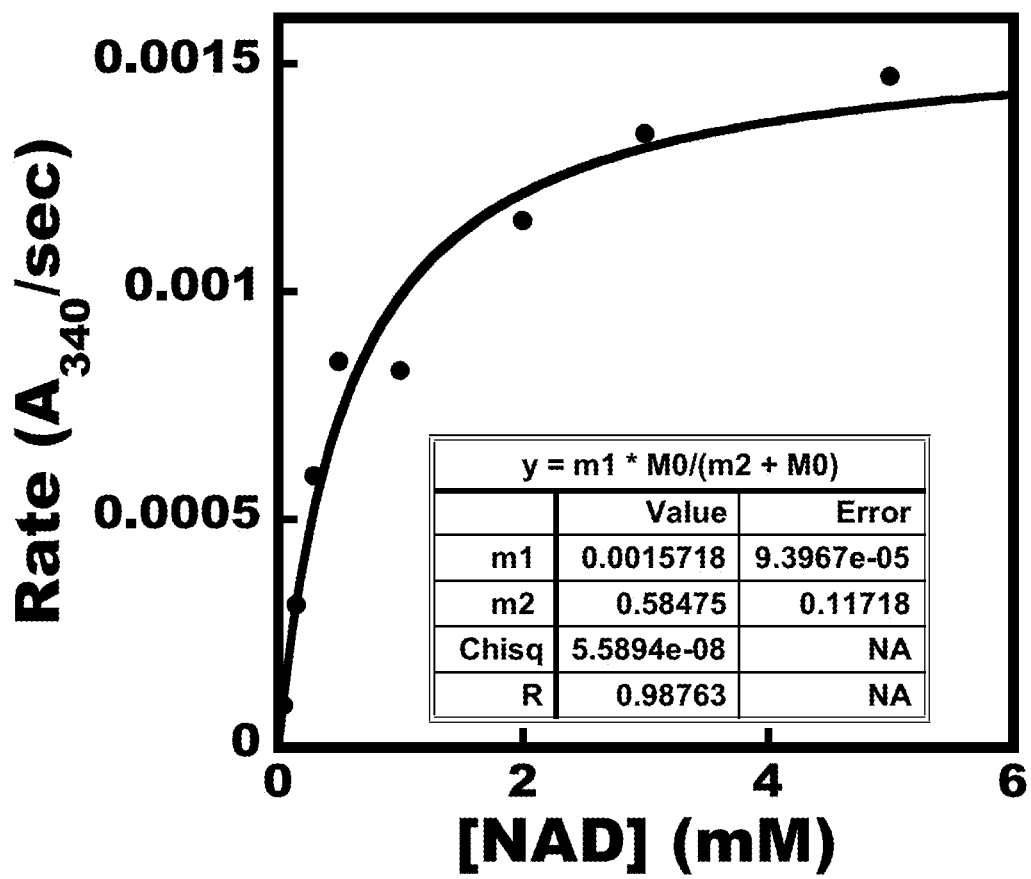

As shown in FIG. 2, and described above, the inventors disclose a method to monitor the production of AMP by coupling it to the oxidation of a low molecular weight aldehyde by bacterial luciferase.

Figure 31:
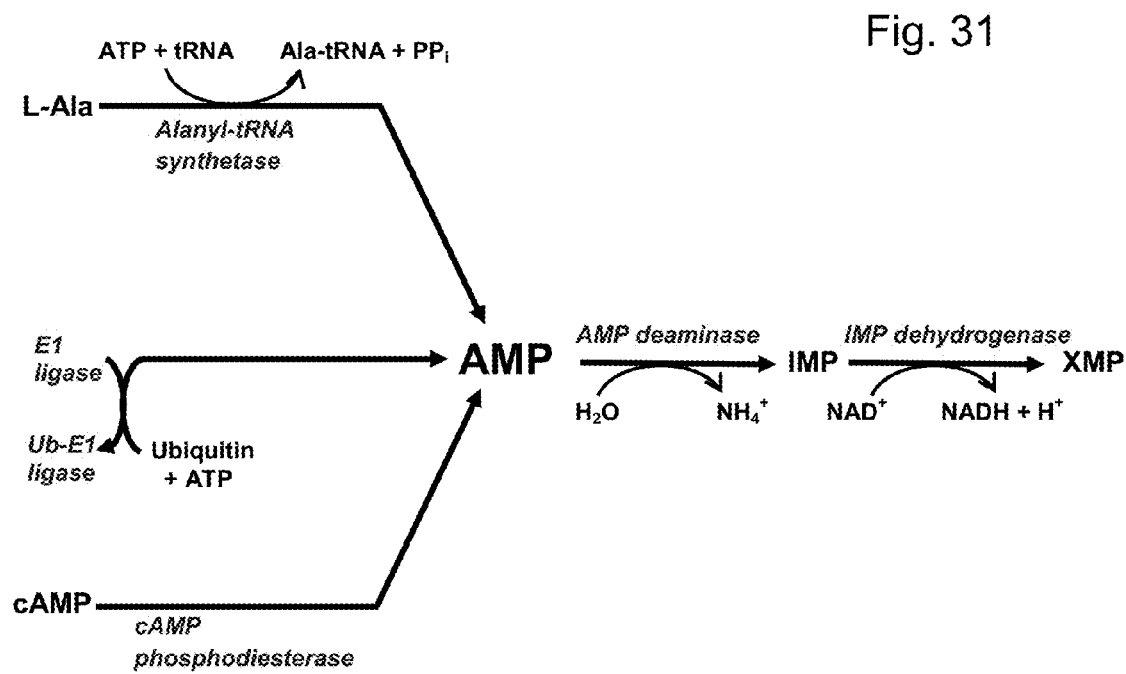
FIG. 31 is a reaction scheme coupling aminoacyl-tRNA synthetases, cAMP phosphodiesterases, ubiquitin ligases, and other enzymes to the AMP assay of FIG. 1.

As shown in FIG. 31, and described above, the inventors disclose a general method to monitor the activity of an enzyme that can be coupled to the production of AMP, including aminoacyl-tRNA synthetases, DNA ligases, ubiqutin and ubiquitin-like ligases, cAMP phosphodiesterases, polyA deadenylases, and ribonucleases.

Figure 32:
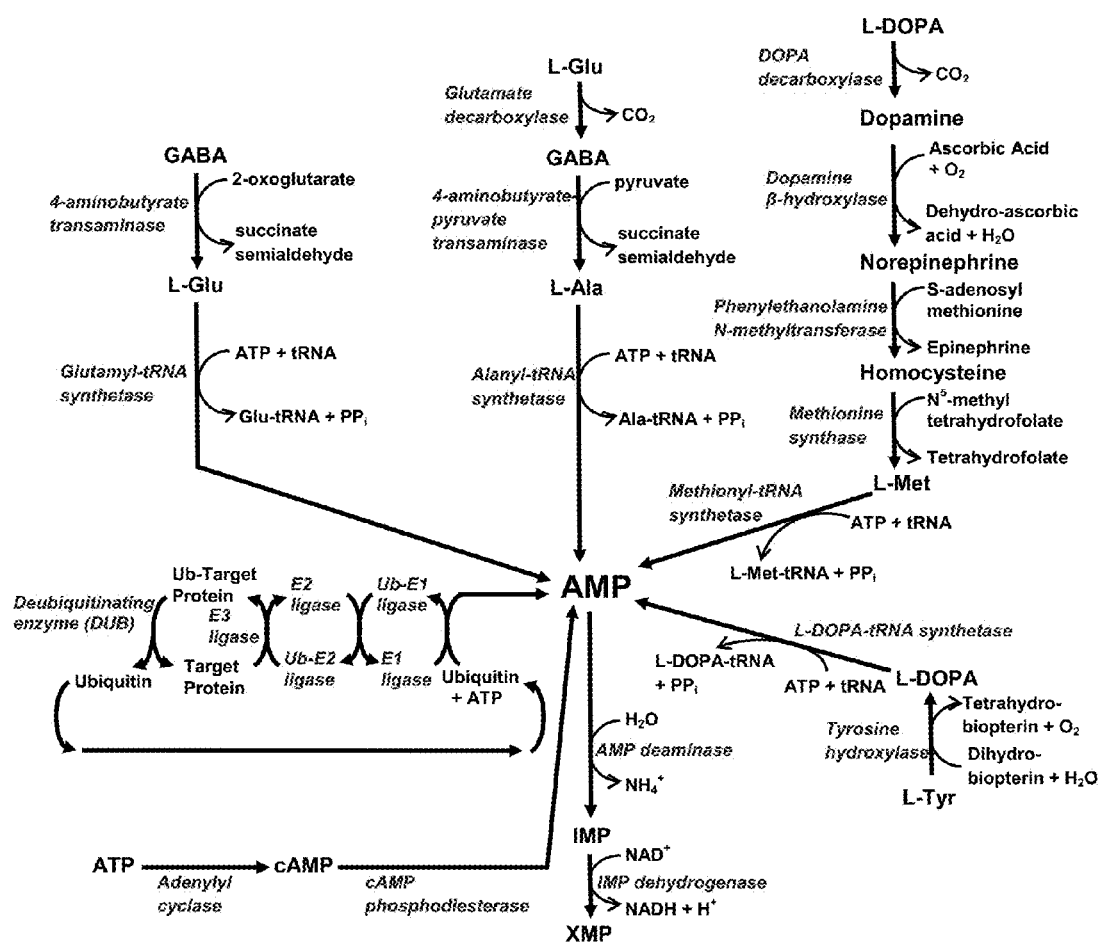
FIG. 32 shows exemplary reaction schemes for monitoring the activity of any enzyme in a pathway that can be coupled to the AMP assay of FIG. 1.

Turning to FIG. 32, and described above, the inventors disclose a general method to monitor the activity of an enzyme in a pathway that can be coupled to the production of AMP. The activity of a particular enzyme in the pathway (i.e., DOPA decarboxylase, dopamine β-hydroxylase, or phenylethanolamine N-methyltransferase) can be monitored by decreasing the concentration of the enzyme such that the step that it catalyzes is rate-limiting in the assay. This will result in the rate of the reaction being entirely dependent on the activity of that (rate-limiting) enzyme.

Figure 33:
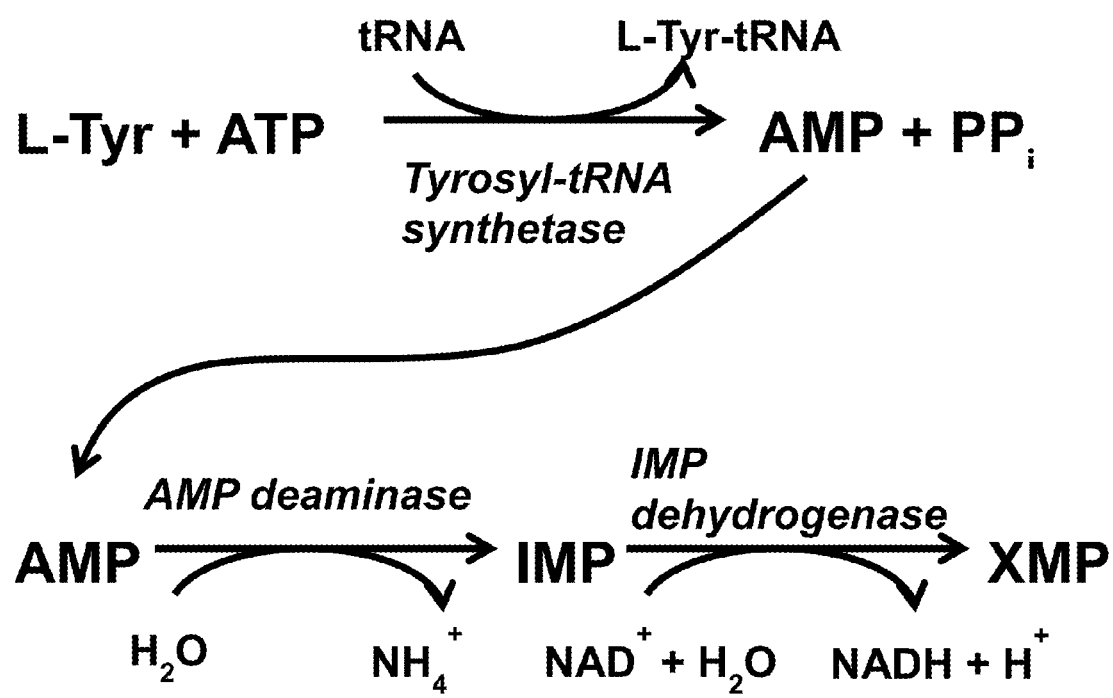
FIG. 33 shows the reaction scheme for monitoring the activity of tyrosyl-tRNA synthetase by coupling it to the production of NADH via the AMP assay.
Figure 34:
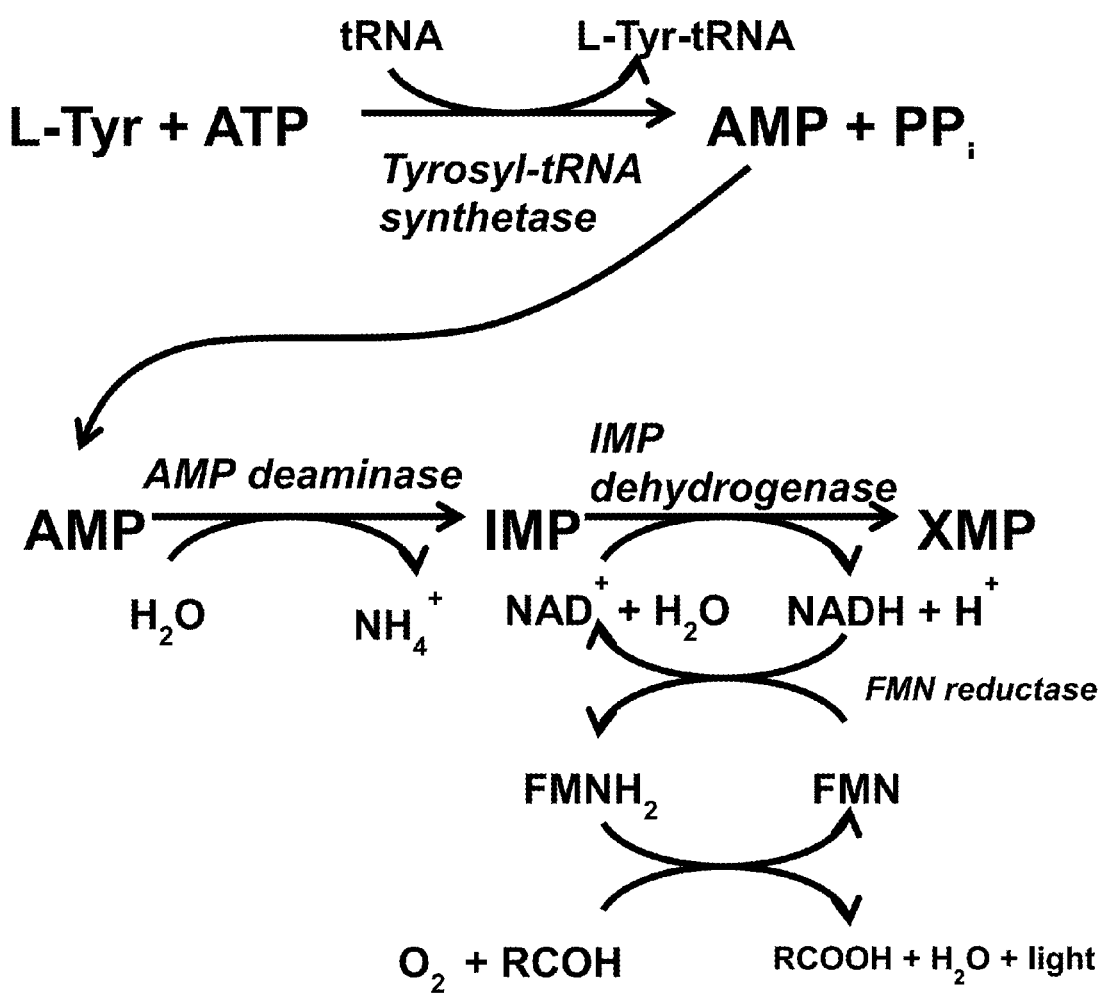
FIG. 34 shows the reaction scheme for monitoring the activity of tyrosyl-tRNA synthetase by coupling it to the production of light by bacterial luciferase via the AMP assay.

Turning to FIGS. 33 and 34, and described above, the inventors disclose a method to monitor the aminoacylation of tRNA by L-tyrosine. Additionally, the inventors disclose a method to monitor the aminoacylation of tRNA by other L-amino acids.

Figure 35:
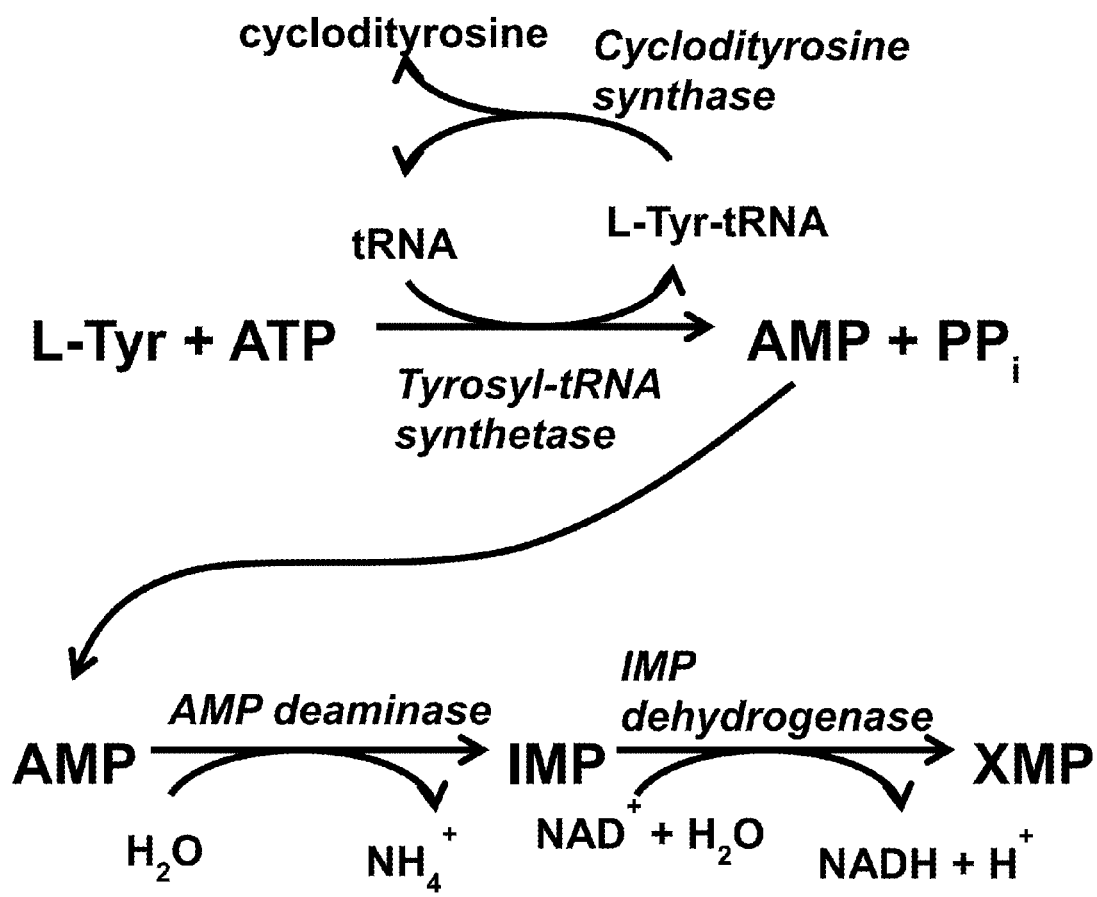
FIG. 35 shows the reaction scheme for a tyrosyl-tRNA synthetase assay in which the tRNA substrate is recycled using cyclodityrosine synthase. An analogous reaction scheme can be drawn in which the activity tyrosyl-tRNA synthetase is coupled to the production of light by bacterial luciferase (i.e. by coupling the production of NADH to the bacterial luciferase catalyzed oxidation of a low molecular weight aldehyde, as shown in FIG. 34 for tyrosyl-tRNA synthetase).
Figure 36:
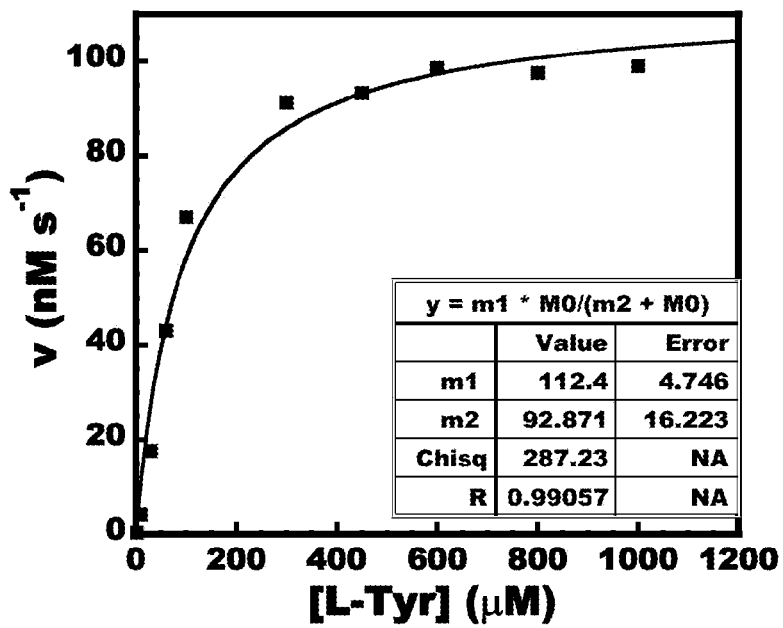
FIGS. 36 and 37 show monitoring the aminoacylation of tRNA by L-tyrosine using a tyrosyl-tRNA synthetase assay in which cyclodityrosine synthase is used to recycle the tRNA substrate.
Figure 37:
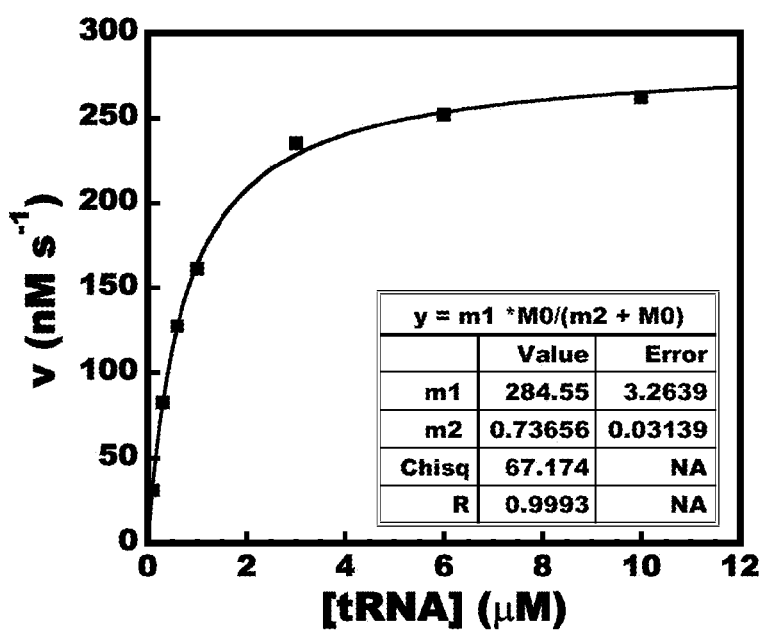

Turning to FIGS. 35-37, and described above, the inventors disclose a method to continuously recycle the tRNA substrate during the aminoacylation of tRNA by L-tyrosine. The enzyme cyclodityrosine synthetase, which converts two molecules of L-Tyr-tRNA to cyclodityrosine+2 tRNA is used to recycle the tRNA substrate.

Further shown in FIGS. 35-37, and described above, the inventors disclose a general method for continuously recycling the tRNA substrate during the aminoacylation of tRNA using cyclodipeptide synthases. The cyclodipeptide synthase (CDPS) family is a recently discovered protein family that is structurally related to the class I aminoacyl-tRNA synthetase family. Members of the cyclic dipeptide synthase family convert two molecules of aminoacyl-tRNAs to a cyclic dipeptide+2 tRNAs. Members of this family include: (1) cyclodityrosine synthetase (also known as RV2275), which produces cyclodityrosine (cYY) from two L-Tyr-tRNAs, (2) AlbC, which produces cyclo(L-Phe-L-Leu) (cFL) from one L-Phe-tRNA and one L-Leu-tRNA, (3) several CDPSs that produce cyclo(L-Leu-L-Leu), (4) a CDPS from Nematostella vectensis that produces cyclodipeptides containing L-Trp, with cyclo(L-Trp-L-Phe), cyclo (L-Trp-L-Leu), and cyclo(L-Trp-L-Met) being the major products (minor products include cWA, cWG, cFF, cFL, cFM, cFA, cYL, cYM, and cLA), and a (5) CDPS from Nocardiopsis dassonvillei that produces cyclo(L-Trp-L-Trp). It is likely that more CDPSs with additional specificities will be identified in the near future, as a BLAST search reveals a number of gene products related to cyclodityrosine synthetase. In addition, CDPS family members tend to be a bit promiscuous, being able to use several different aminoacyl-tRNAs as substrates. Members of the CDPS family that produce a homozygous cyclodipeptide (e.g. cYY, cLL, cWW, cFF) can be used to recycle the tRNA substrate during the tRNA aminoacylation reaction. This is illustrated for cyclodityrosine synthetase in FIGS. 35-37.

Figure 38:
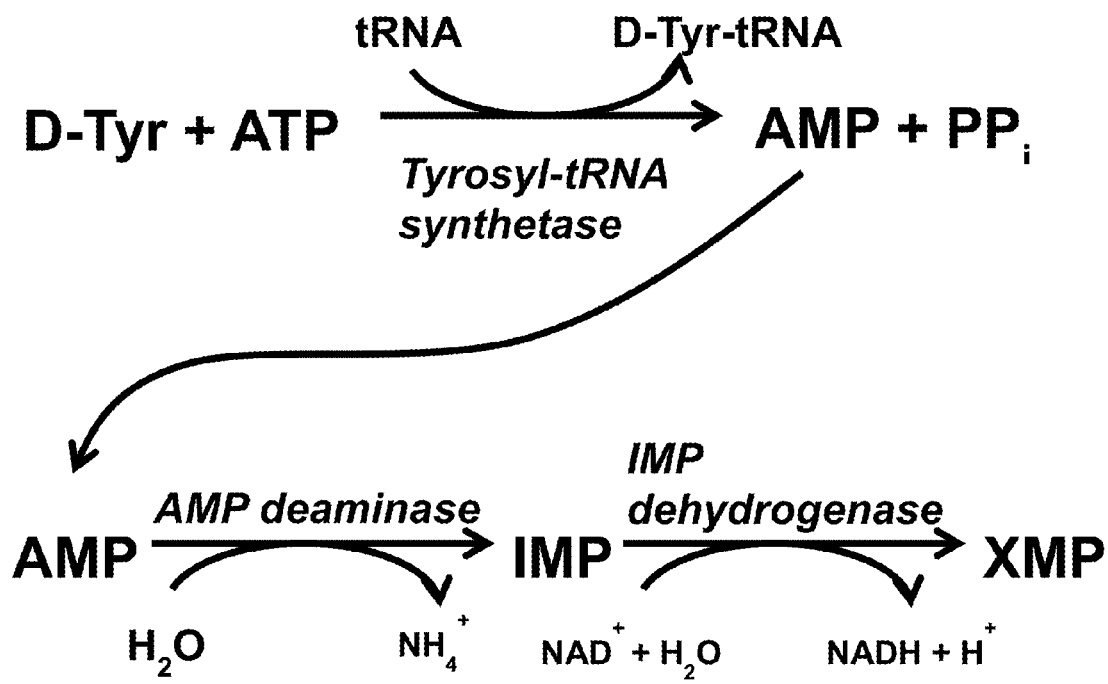
FIG. 38 shows the reaction scheme for monitoring the aminoacylation of tRNA by D-tyrosine by coupling it to the production of NADH via the AMP assay.
Figure 39:
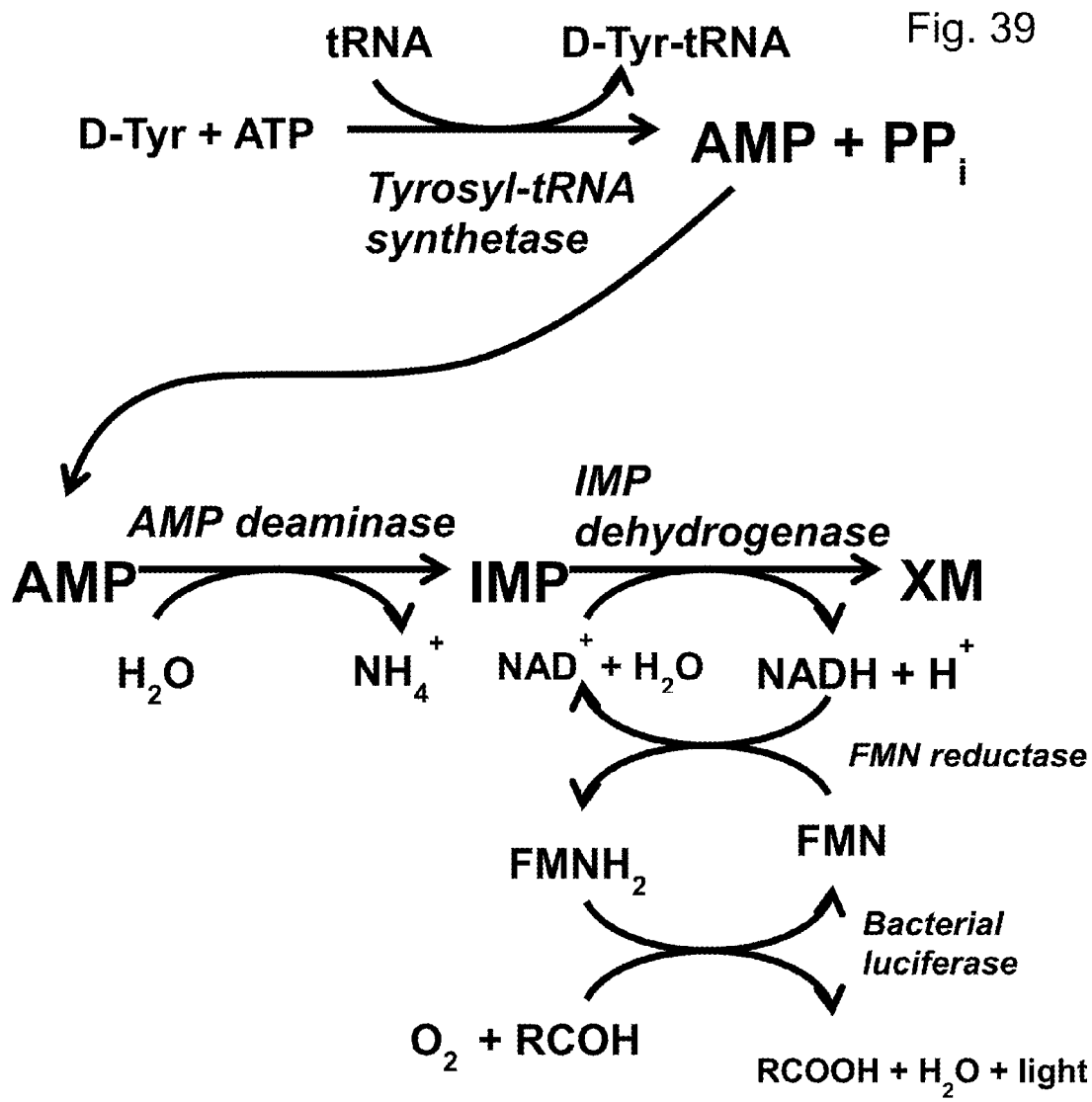
FIG. 39 shows the reaction scheme for monitoring the aminoacylation of tRNA by D-tyrosine by coupling it to production of light by bacterial luciferase via the AMP assay.

Turning to FIGS. 38 and 39, and described above, the inventors disclose a method to monitor the aminoacylation of tRNA by D-tyrosine.

Figure 40:
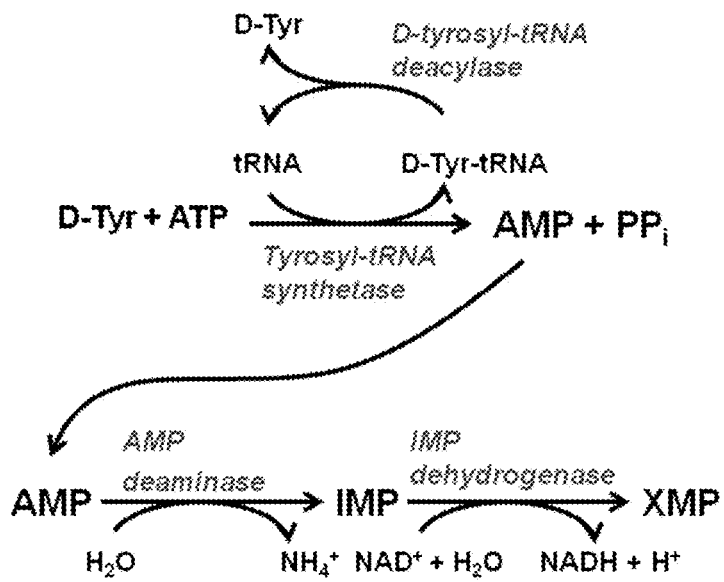
FIGS. 40-42 show the aminoacylation of tRNA$^{Tyr}$ by D-tyrosine.
Figure 41:
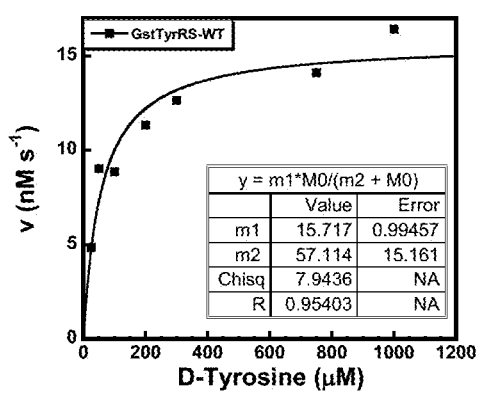
Figure 42:
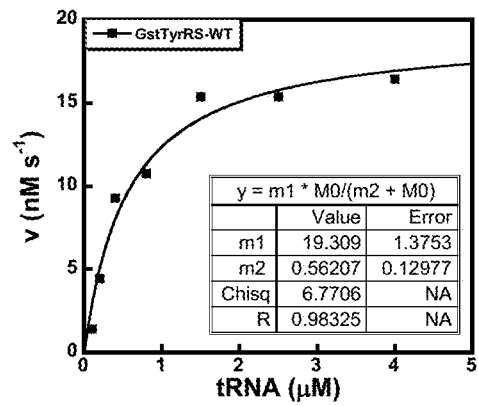

Turning to FIGS. 40-42, and described above, the inventors disclose a method to continuously recycle the tRNA substrate during the aminoacylation of tRNA by D-amino acids. This is analogous to the mechanism shown in FIGS. 35-37, except that L-tyrosine is replaced by D-tyrosine and cyclodityrosine synthetase is replaced by D-tyrosyl-tRNA deacylase. D-tyrosyl-tRNA synthetase hydrolyzes D-aminoacyl-tRNAs, releasing the D-amino acid+tRNA.

Figure 43:
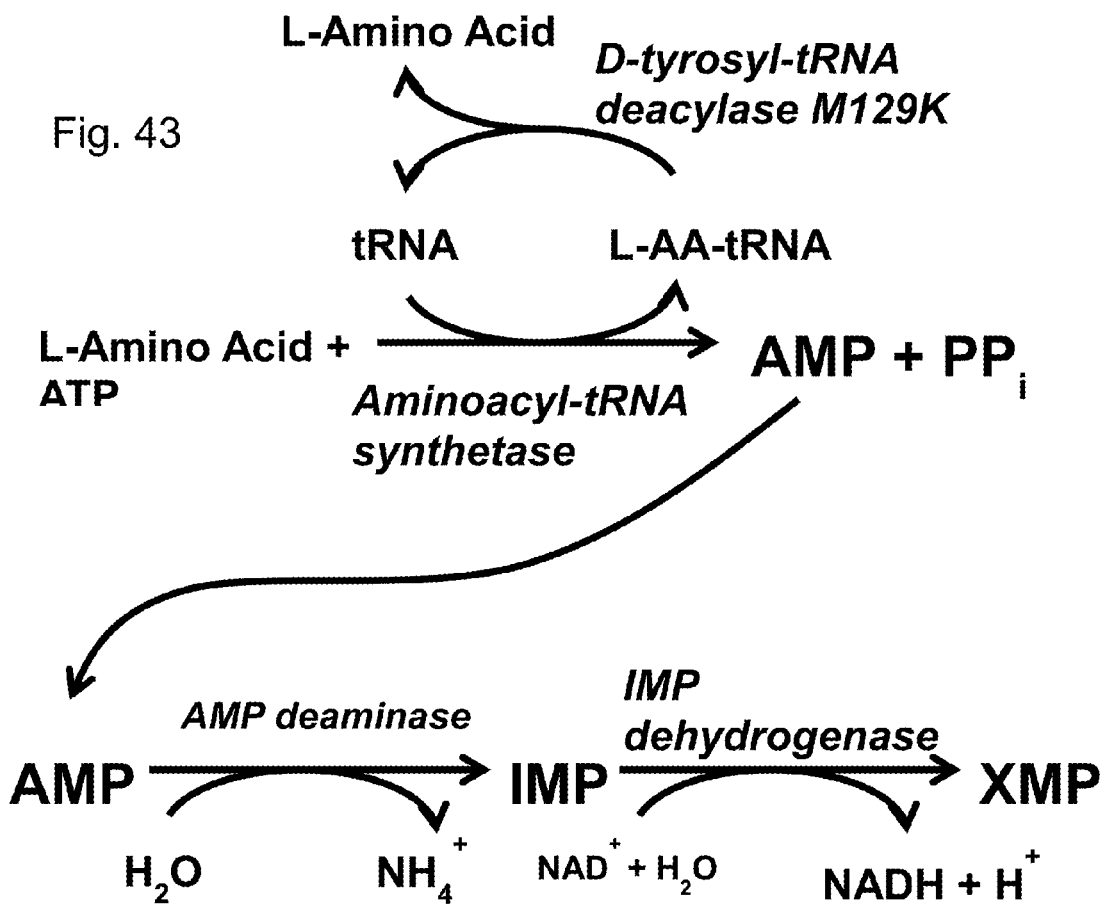
FIG. 43 is the reaction scheme for a general aminoacyl-tRNA synthetase assay in which the tRNA substrate is recycled using a variant of D-tyrosyl-tRNA deacylase M129K variant. In the D-tyrosyl-tRNA deacylase M129K variant, the methionine at position 129 is replaced by a lysine residue (amino acid numbering is based on *Thermus thermophilus* D-tyrosyl-tRNA deacylase sequence).
Figure 44:
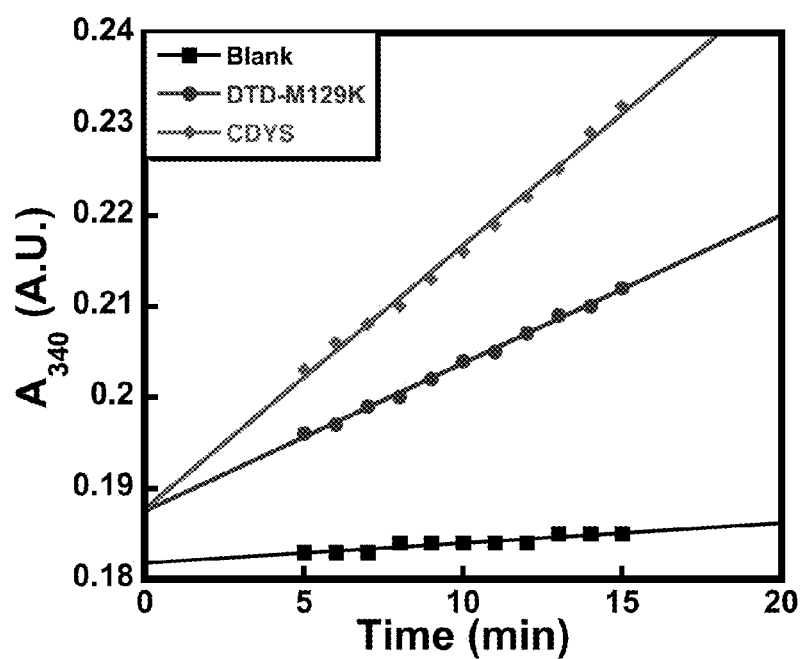
FIG. 44 is the aminoacylation of tRNA by L-tyrosine using the M129K variant of D-tyrosyl-tRNA deacylase to recycle the tRNA substrate. Time courses are shown for the aminoacylation of tRNA$^{Tyr}$ by L-tyrosine in which the Tyr-tRNA product is not hydrolyzed (square), the Tyr-tRNA product is hydrolyzed by the M129K variant of D-tyrosyl-tRNA deacylase (DTD-M129K, circle), and the Tyr-tRNA product is converted to cycloditytrosine and tRNA by cycloditytrosine synthetase (CDYS, diamond). The assays contained 1 mM L-tyrosine, 10 mM MgATP, 2 µM tRNA$^{Tyr}$, and 0.25 µM *G. stearothermophilus* tyrosyl-tRNA synthetase. The concentrations of DTD-M129K and CDYS were 2 µM and 8.6 µM, respectively.

Turning to FIGS. 43 and 44, and described above, the inventors disclose a method to continuously recycle the tRNA substrate during the aminoacylation of tRNA by any L-amino acid using the M129K variant of D-tyrosyl-tRNA deacylase (i.e., a variant of D-tyrosyl-tRNA deacylase in which the methionine at position 129 has been replaced by a lysine residue). This process is similar to that shown in FIGS. 35-37, except that cyclodityrosine synthetase is replaced by the M129K variant of D-tyrosyl-tRNA deacylase. The M129K variant of D-tyrosyl-tRNA synthetase hydrolyzes both L- and D-aminoacyl-tRNAs, releasing the amino acid+tRNA. L-amino acids that have been shown to bind to the M129K variant of D-tyrosyl-tRNA deacylase are shown in Table 3.

Figure 45:
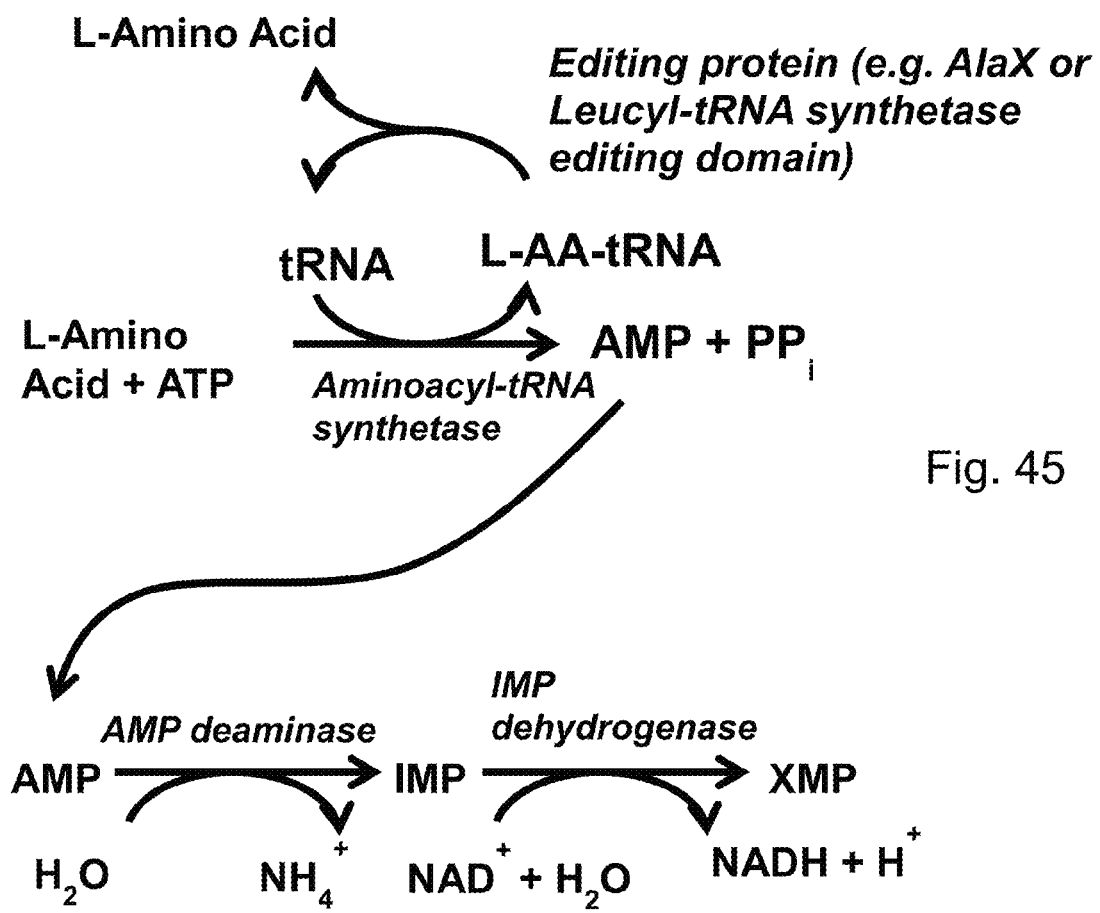
FIG. 45 is the reaction scheme for a general aminoacyl-tRNA synthetase assay in which the tRNA substrate is recycled using an editing domain or protein, or an aminoacyl-tRNA synthetase containing an editing domain in which the catalytic site has been inactivated.

Turning to FIG. 45, and described above, the inventors disclose a method to continuously recycle the tRNA substrate during the aminoacylation of tRNA by an L-amino acid using an editing domain, editing protein, or protein containing an editing domain. This process is similar to that shown in FIGS. 35-37, except that cyclodityrosine synthetase by an aminoacyl-tRNA synthetase editing domain, an aminoacyl-tRNA synthetase containing an editing domain in which the catalytic site has been inactivated (e.g. by mutagenesis), or an aminoacyl-tRNA editing protein. These aminoacyl-tRNA editing proteins specifically hydrolyze a single aminoacyl-tRNA or subset of aminoacyl-tRNAs.

Figure 46:
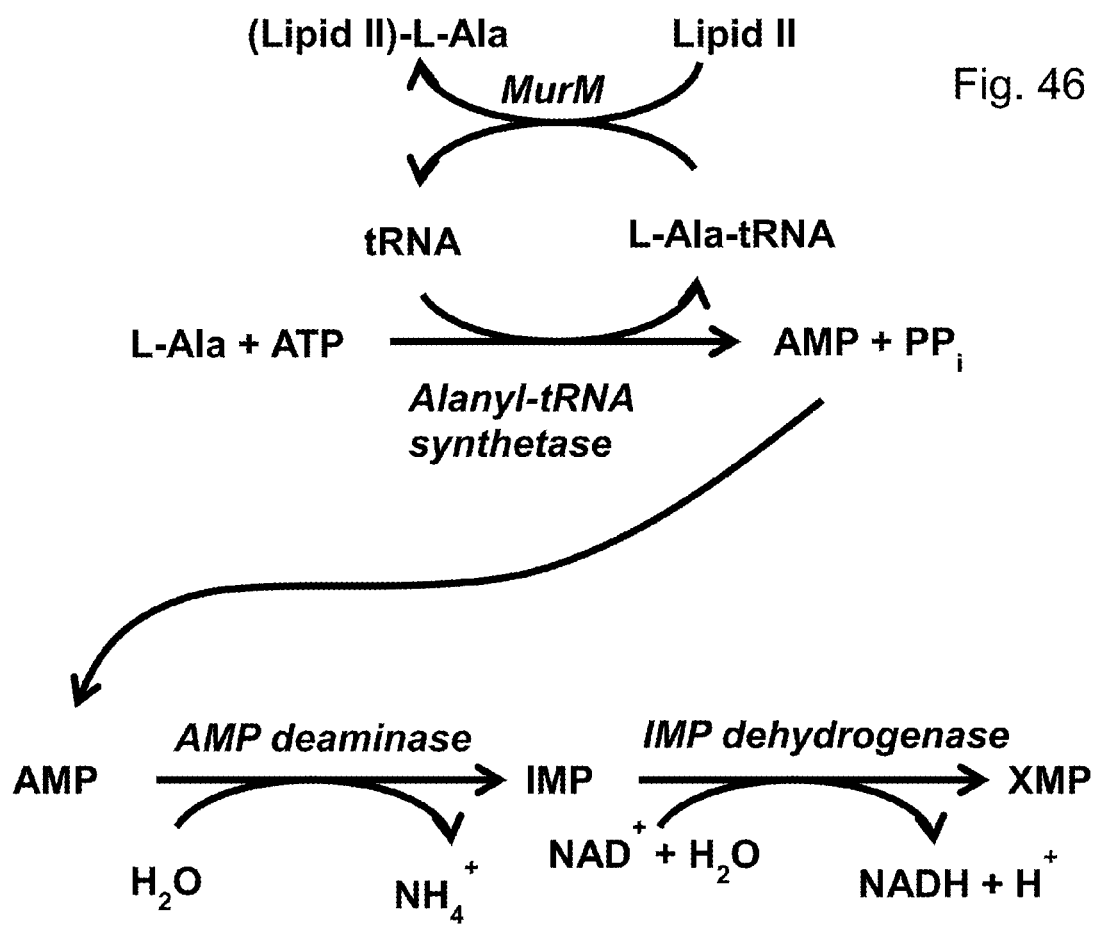
FIG. 46 is the reaction scheme for an alanyl-tRNA synthetase assay in which the tRNA substrate is recycled using MurM. An analogous reaction scheme can be drawn in which the activity alanyl-tRNA synthetase is coupled to the production of light by bacterial luciferase (i.e. by coupling the production of NADH to the bacterial luciferase catalyzed oxidation of a low molecular weight aldehyde, as shown in FIG. 34 for tyrosyl-tRNA synthetase).

Turning to FIG. 46, and described above, the inventors disclose a method to continuously recycle the tRNA substrate during the aminoacylation of tRNA using the Penicillin Resistance Factor MurM. MurM is an aminoacyl-tRNA ligase that transfers the aminoacyl moieties from L-Ser-tRNA and L-Ala-tRNA to the stem peptide lysine in Lipid II in the cell wall proteoglycan of Streptococcus pneumoniae. MurM is essential for clinically observed penicillin resistance in Streptococcus pneumoniae. MurM can be used to recycle the seryl-tRNA and alanyl-tRNA products in seryl- and alanyl-tRNA synthetase assays using a method that is analogous to the use of cyclodityrosine synthetase to recycle the Tyr-tRNA product in the tyrosyl-tRNA synthetase assay (FIGS. 35-37). This approach is illustrated in FIG. 46 for alanyl-tRNA synthetase.

Figure 47:
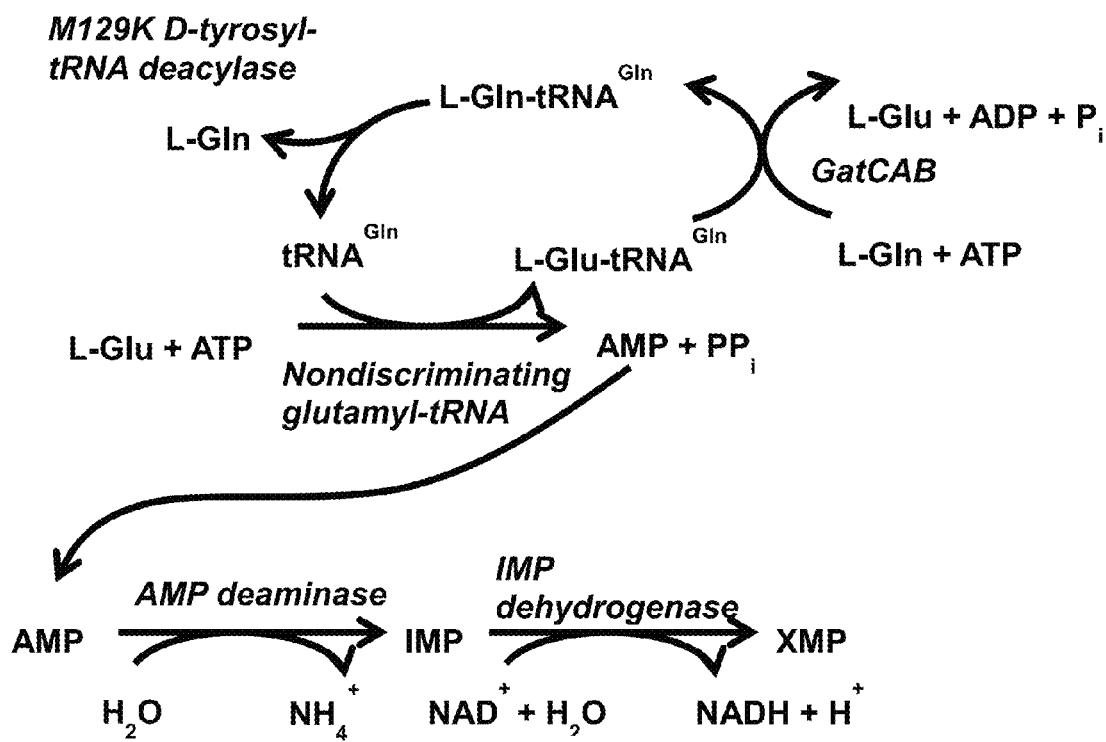
FIG. 47 is a reaction scheme for an glutamyl-tRNA synthetase assay in which Glu-tRNA$^{Gln}$ is converted to Gln-tRNA$^{Gln}$ prior to hydrolysis. An analogous reaction scheme can be drawn in which the activity of the nondiscriminating glutamyl-tRNA synthetase is coupled to the production of light by bacterial luciferase (i.e. by coupling the production of NADH to the bacterial luciferase catalyzed oxidation of a low molecular weight aldehyde, as shown in FIG. 34 for tyrosyl-tRNA synthetase).

Turning to FIG. 47, and described above, the inventors disclose a method to continuously recycle the tRNA substrate during the aminoacylation of tRNA that removes the amino acid after hydrolysis of the aminoacyl-tRNA product. In some instances it may be desirable to remove (or convert) the amino acid from the aminoacyl-tRNA synthetase assay after hydrolysis of the aminoacyl-tRNA product has occurred (i.e. after the tRNA substrate has been recycled). For example, if a metabolic pathway is coupled to the aminoacyl-tRNA synthetase assay through the production of an amino acid, recycling of the aminoacyl-tRNA product must be done in a way that regenerates the tRNA substrate but not the amino acid substrate. The use of cyclodipeptide synthases to regenerate the tRNA substrate is one approach that does not regenerate the amino acid substrate. An alternate approach is to transform the aminoacyl moiety prior to hydrolysis of the aminoacyl-tRNA product. This can be done for Glu-tRNA and Asp-tRNA by using an asparagine or glutamine-dependent amidotransferase such as the GatCAB or GatDE. In this approach the tRNA aminoacylation reaction is catalyzed by a non-discriminating glutamyl- or aspartyl-tRNA synthetase, which misacylates tRNA$^{Gln}$ or tRNA$^{Asn}$ with L-Glu or L-Asp. The misacylated L-Glu-tRNA$^{Gln}$ and L-Asp-tRNA$^{Asn}$ products are then converted to L-Gln-tRNA$^{Gln}$ or L-Asn-tRNA$^{Asn}$ by the amidotransferase. Subsequent hydrolysis of the aminoacyl-tRNA product releases L-Gln+tRNA or L-Asn+tRNA, rather than the L-Glu or L-Asp substrates. In this assay, the concentration of the transamidase (e.g. GatCAB) must be high enough to ensure that the conversion of L-Glu-tRNA$^{Gln}$ to L-Gln-tRNA$^{Gln}$ precedes the hydrolysis reaction (i.e. high enough to prevent Glu-tRNA$^{Gln}$ from being hydrolyzed before transamidation occurs). This approach is illustrated in FIG. 47.

Figure 48:
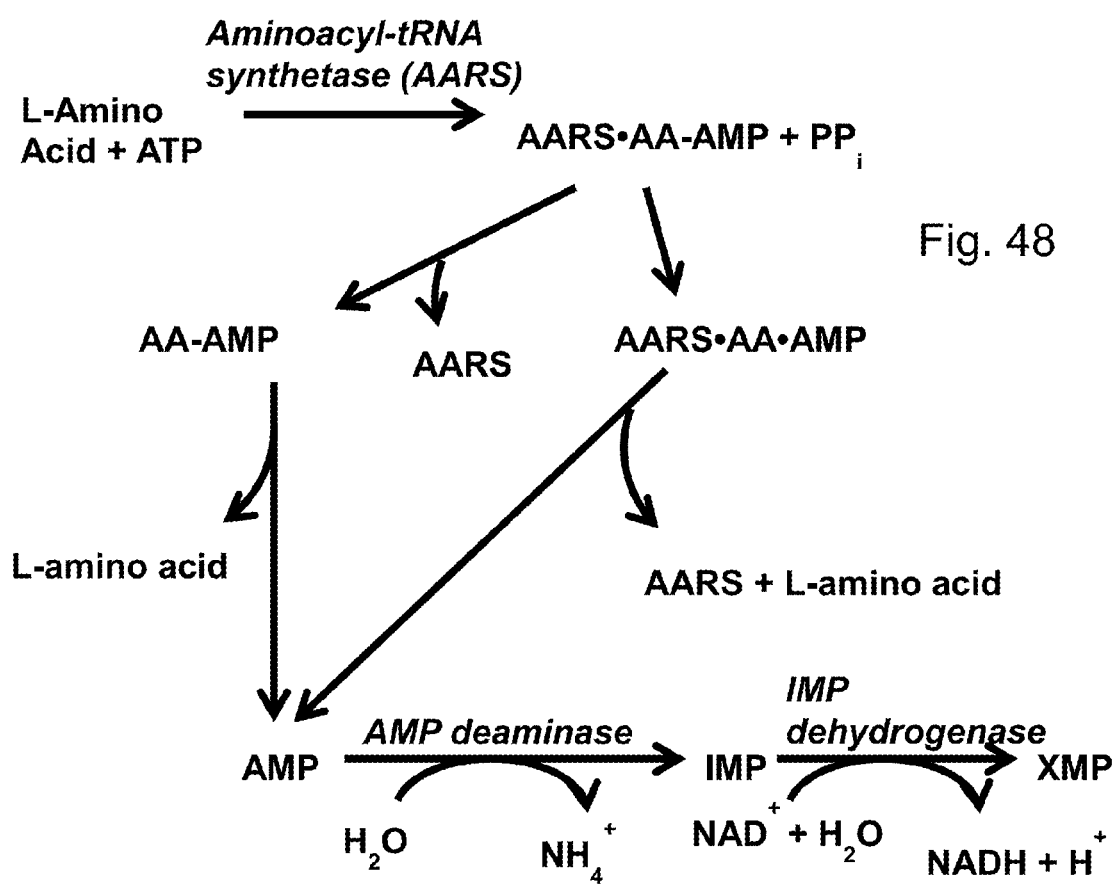
FIG. 48 is a reaction scheme for monitoring pre-transfer editing by any aminoacyl-tRNA synthetase by coupling the release of AMP to the production of NADH. Covalent bonds are indicated by "-" and non-covalent interactions are indicated by "•".
Figure 49:
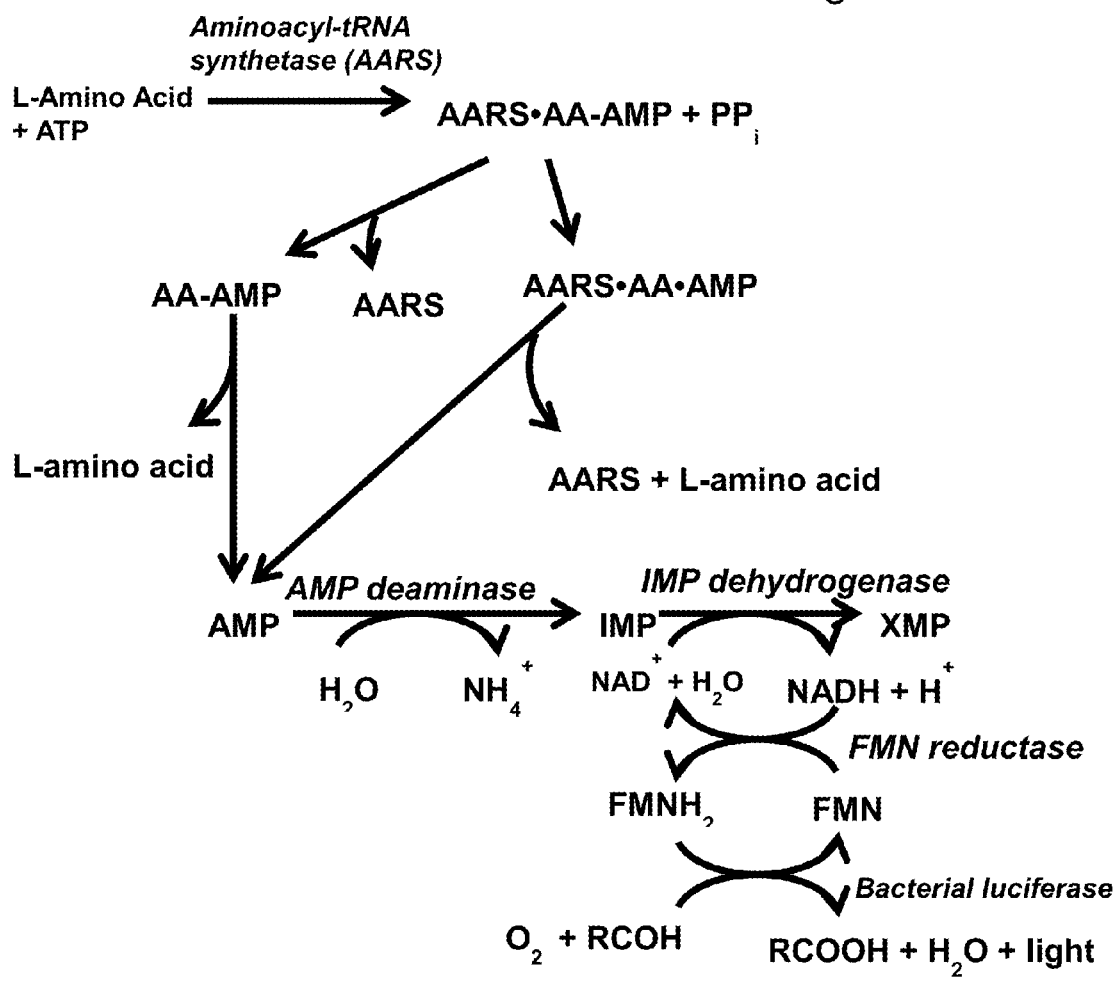
FIG. 49 is a reaction scheme for monitoring pre-transfer editing by any aminoacyl-tRNA synthetase by coupling the release of AMP to the production of light by bacterial luciferase. Covalent bonds are indicated by "-" and noncovalent interactions are indicated by "•".

Turning to FIGS. 48 and 49, and described above, the inventors disclose a method to monitor the pre-transfer editing activity of an aminoacyl-tRNA synthetase. Aminoacyl-tRNA synthetases catalyze the aminoacylation of tRNA using a two-step mechanism discussed above. In the first step, the amino acid is activated by ATP, forming an enzyme-bound aminoacyl-adenylate intermediate:

$$E+AA+ATP \rightarrow E \cdot AA\text{-}AMP+PP_i$$

where '•' indicates a non-covalent interaction, '-' indicates a covalent interaction, E represents the aminoacyl-tRNA synthetase, AA represents the amino acid, and $PP_i$ represents inorganic pyrophosphate). In the second step, the aminoacyl moiety is transferred to the 3' end of tRNA and the aminoacyl-tRNA and AMP products are released from the enzyme:

$$E \cdot AA\text{-}AMP+tRNA \rightarrow E+AA\text{-}tRNA+AMP$$

Pre-transfer editing occurs when the aminoacyl-AMP intermediate (AA-AMP) is hydrolyzed prior to being transferred to the tRNA. This can occur either while it is still bound to the enzyme (i.e., $E \cdot AA\text{-}AMP \rightarrow E \cdot AA \cdot AMP \rightarrow E+AA+AMP$), or after it has been released from the enzyme (i.e., $E \cdot AA\text{-}AMP \rightarrow E+AA\text{-}AMP \rightarrow E+AA+AMP$). In either case, AMP is released as a product of the AA-AMP hydrolysis. Since AMP is released as a product of pre-transfer editing, the assays shown in FIGS. 1 and 2, for example, can be used to monitor pre-transfer editing activity.

Figure 50:
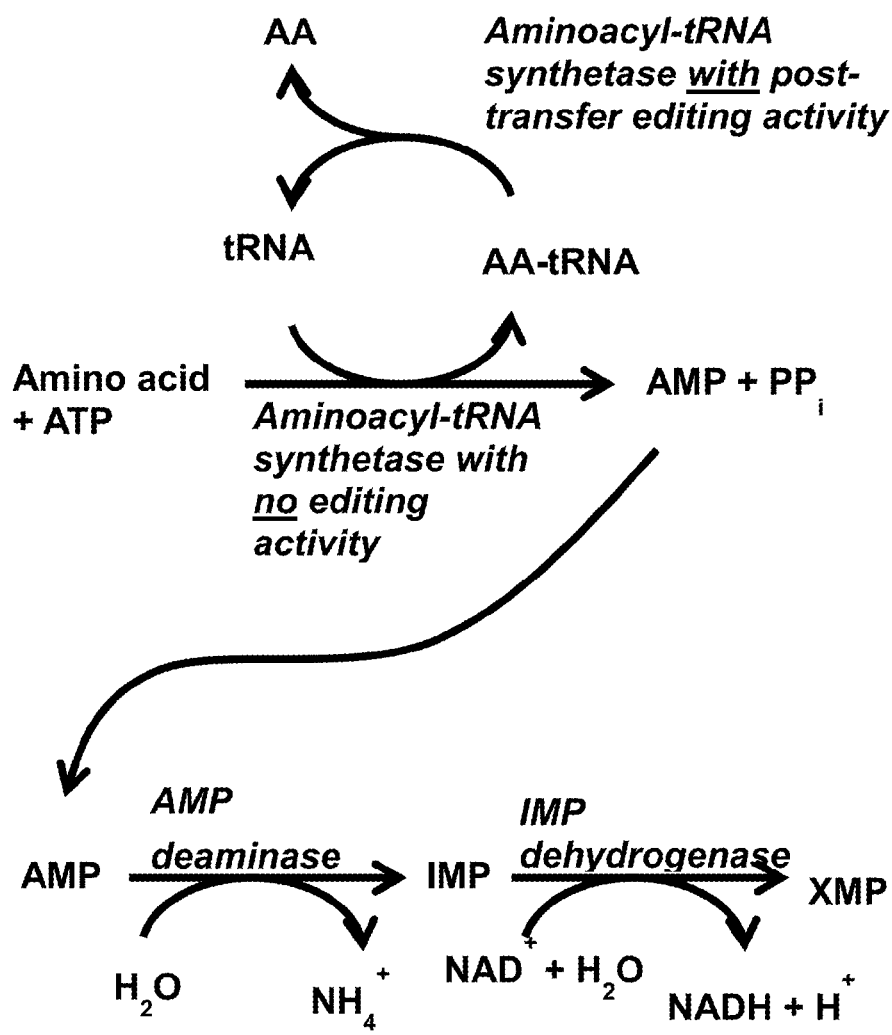
FIG. 50 is a reaction scheme for monitoring post-transfer editing by any aminoacyl-tRNA synthetase by coupling the release of AMP to the production of NADH. A reaction scheme that is analogous to FIG. 45 can be drawn in which post-transfer editing by an aminoacyl-tRNA synthetase is coupled the production of light by bacterial luciferase.

Turning to FIG. 50, and described above, the inventors disclose a method to monitor the post-transfer editing activity of any aminoacyl-tRNA synthetase or aminoacyl-tRNA editing protein. Aminoacyl-tRNA synthetases catalyze the aminoacylation of tRNA using a two-step mechanism as described above. In the first step, the amino acid is activated by ATP, forming an enzyme-bound aminoacyl-adenylate intermediate:

$$E+AA+ATP \rightarrow E \cdot AA\text{-}AMP+PP_i$$

where '•' indicates a noncovalent interaction, '-' indicates a covalent interaction, E represents the aminoacyl-tRNA synthetase, AA represents the amino acid, and $PP_i$ represents inorganic pyrophosphate). In the second step, the aminoacyl moiety is transferred to the 3' end of tRNA and the aminoacyl-tRNA and AMP products are released from the enzyme:

$$E \cdot AA\text{-}AMP+tRNA \rightarrow E+AA\text{-}tRNA+AMP$$

Post-transfer editing occurs when the aminoacyl-AMP intermediate (AA-AMP) is hydrolyzed after to being transferred to the tRNA (i.e., $E \cdot AA\text{-}tRNA \rightarrow E+AA+tRNA$). Since tRNA is released as a product, the rate of post-transfer editing by an aminoacyl-tRNA synthetase can be monitored using the assays described in FIGS. 12-20. To monitor the post-transfer editing activity, rather than the tRNA aminoacylation reaction, two different aminoacyl-tRNA synthetases are used. The first aminoacyl-tRNA synthetase is the wild-type enzyme, while the second aminoacyl-tRNA synthetase is identical to the wild-type enzyme except the editing domain has been inactivated by either deletion or mutagenesis. This second aminoacyl-tRNA synthetase is used to generate the aminoacyl-tRNA product that will be hydrolyzed by the post-transfer editing site in the wild type enzyme. By adjusting conditions such that the amino acid and ATP substrates are at saturating concentrations (e.g., 10-fold above their $K_m$ values or higher) to ensure that the tRNA is always aminoacylated, and making the concentration of the wild type aminoacyl-tRNA synthetase sufficiently low such that post-translation editing is the rate-limiting step, one can measure the post-transfer editing activity of wild type aminoacyl-tRNA synthetase. This is illustrated in FIG. 50 in which an editing defective variant of phenylalanyl-tRNA synthetase (D243A) is combined with wild-type phenylalanyl-tRNA synthetase to monitor the post-transfer editing of Tyr-tRNA$^{Phe}$ by phenylalanyl-tRNA synthetase.

Turning again to FIG. 32, and described above, the inventors disclose a general method to monitor the activity of an enzyme in a pathway that can be coupled to the aminoacylation of tRNA. The GABA, L-Glu, L-DOPA, and L-Tyr reaction schemes in FIG. 32 are examples of reaction schemes for monitoring the activity of any enzyme in a pathway that can be coupled to the aminoacylation of tRNA. To determine the activity of a particular enzyme in a pathway, the concentration of the enzyme is decreased until the step that it catalyzes becomes rate-limiting. Since the enzyme is rate-limiting for the assay, the rate at which NADH is produced will correspond to the rate at which the enzyme catalyzes its reaction. For example, if the concentration of dopamine β-hydroxylase in the above figure is decreased to the point where the conversion of dopamine to norepinephrine becomes the rate-limiting step in the assay, then the rate at which NADH is formed will be determined by the activity of dopamine β-hydroxylase. An analogous reaction scheme can be drawn in which the activity of the enzyme is coupled the production of light by bacterial luciferase (e.g., by coupling the production of NADH to the bacterial luciferase catalyzed oxidation of a low molecular weight aldehyde, as described above).

Turning next to FIG. 52, and described above, the inventors disclose a method to continuously recycle the ubiquitin substrate using deubiquitinating enzymes.

Turning next to FIG. 53, and described above, the inventors disclose a method to monitor the activity of tyrosine hydroxylase by coupling it to the aminoacylation of tRNA by L-DOPA. The production of L-DOPA by tyrosine hydroxylase is monitored using a variant of tyrosyl-tRNA synthetase that has been engineered to use L-DOPA as a substrate (i.e., L-DOPA-tRNA synthetase). L-DOPA-tRNA synthetase catalyzes the aminoacylation of tRNA$^{Tyr}$ by L-DOPA, releasing AMP as a product (L-DOPA+ATP+tRNA$^{Tyr} \rightarrow$ L-DOPA-tRNA$^{Tyr}$+AMP+PP$_i$).

Figure 54:
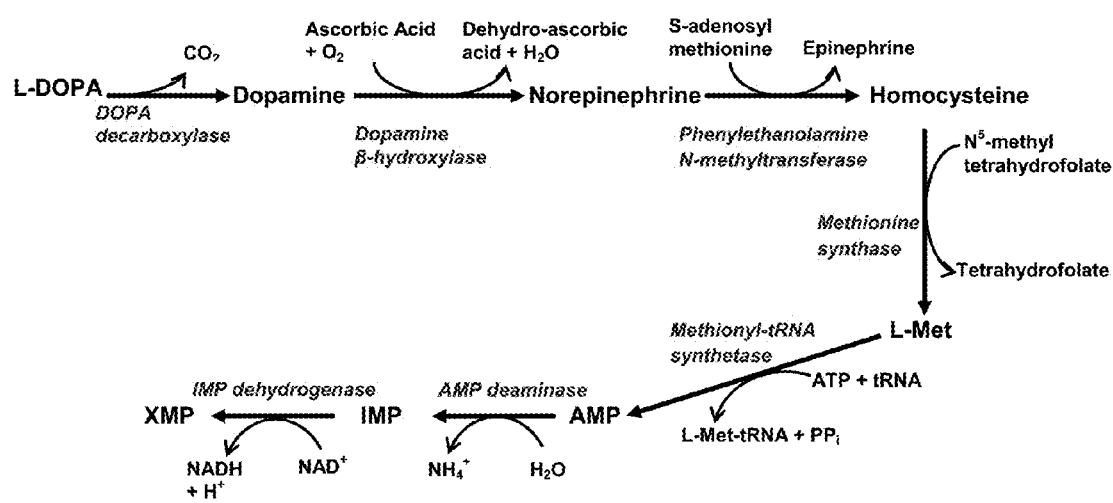
FIG. 54 is a reaction scheme for monitoring the activity of the dopamine/norepinephrine/epinephrine pathway by coupling it to the production of NADH via the AMP assay. L-DOPA-tRNA synthetase is an engineered version of tyrosyl-tRNA synthetse that aminoacylates tRNA$^{Tyr}$ with L-DOPA. An analogous reaction scheme can be drawn in which the activity of tyrosine hydroxylase is coupled the production of light by bacterial luciferase (e.g., by coupling the production of NADH to the bacterial luciferase catalyzed oxidation of a low molecular weight aldehyde, as described above)

Turning next to FIG. 54, and described above, the inventors disclose a method to monitor the activity of every enzyme in the dopamine-norepinephrine-epinephrine biosynthetic pathway by coupling the production of epinephrine to the aminoacylation of tRNA by methionine. The conversion of norepinephrine to epinephrine (the final step in the dopamine-norepinephrine-epinephrine biosynthetic pathway) releases homocysteine as a product. This allows the activity of the dopamine-norepinephrine-epinephrine pathway to be monitored by using methionine synthase to catalyze the conversion of homocysteine to L-methionine. Methionyl-tRNA synthetase is then used to catalyze the aminoacylation of tRNA by L-methionine, resulting in the release of AMP (L-Met+ATP+tRNA$\rightarrow$L-Met-tRNA+AMP+PP$_i$). The activity of a particular enzyme in the pathway (i.e., DOPA decarboxylase, dopamine β-hydroxylase, or phenylethanolamine N-methyltransferase) can be monitored by decreasing the concentration of the enzyme such that the step that it catalyzes is rate-limiting in the assay. This will result in the rate of the reaction being entirely dependent on the activity of that (rate-limiting) enzyme.

Figure 55:
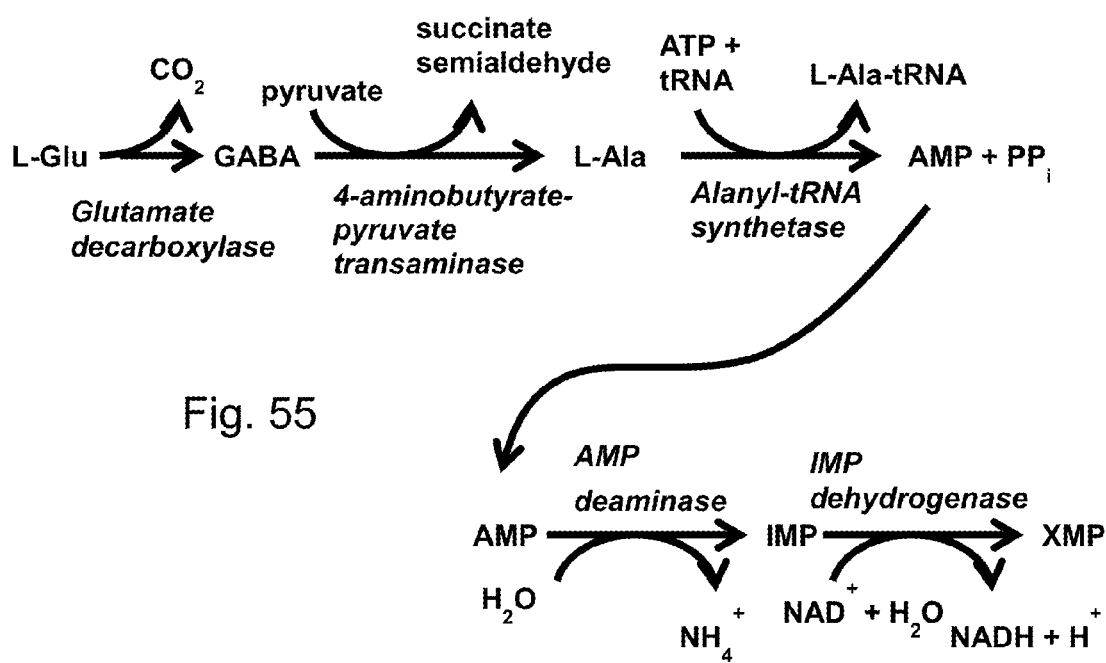
FIG. 55 is a reaction scheme for monitoring the activity of the enzymes in the GABA metabolic pathway by coupling it to the production of NADH via alanyl-tRNA synthetase and the AMP assay. An analogous reaction scheme can be drawn in which the activity of the enzymes in the GABA metabolic pathway are coupled the production of light by bacterial luciferase (i.e. by coupling the production of NADH to the bacterial luciferase catalyzed oxidation of a low molecular weight aldehyde, as described above).
Figure 56:
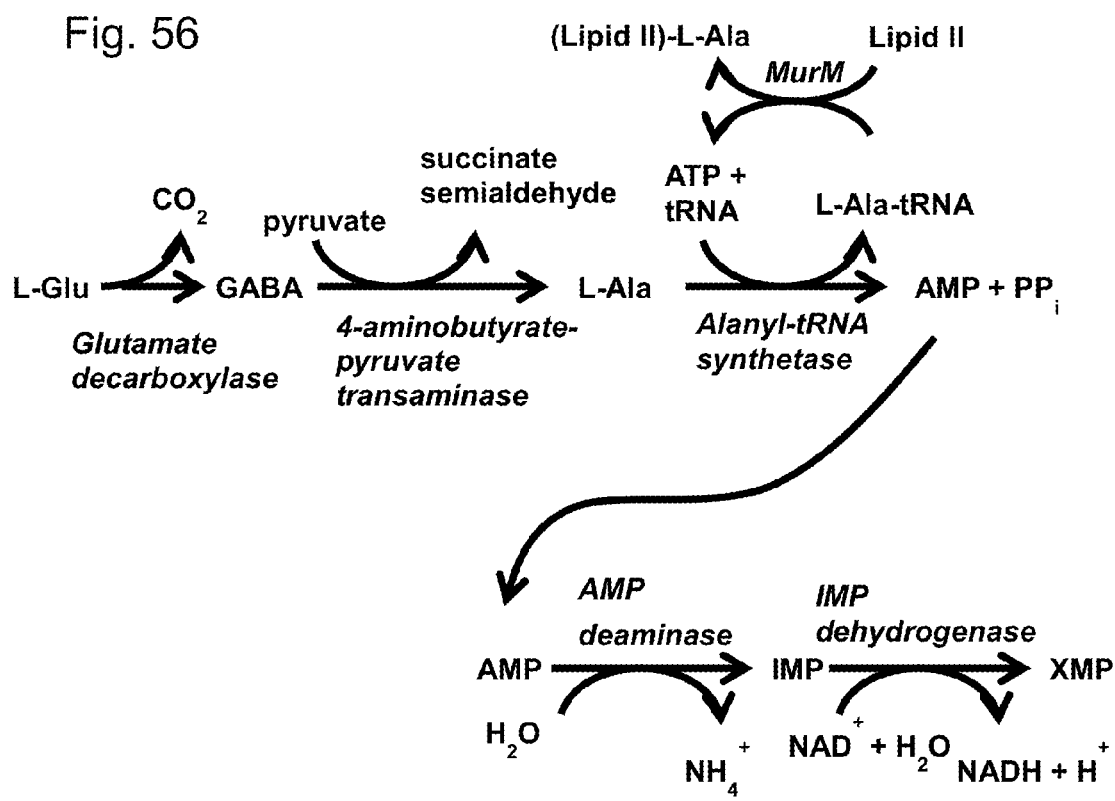
FIG. 56 is a reaction scheme for monitoring the activity of the enzymes in the GABA metabolic pathway in which MurM is used to recycle the L-Ala-tRNA product. An analogous reaction scheme can be drawn in which the activity of the enzymes in the GABA metabolic pathway are coupled the production of light by bacterial luciferase (i.e. by coupling the production of NADH to the bacterial luciferase catalyzed oxidation of a low molecular weight aldehyde, as described above).

Turning next to FIGS. 55 and 56, and described above, the inventors disclose a method to monitor the activity of the enzymes involved in the synthesis and breakdown of 4-aminobutyrate (GABA) by coupling the GABA metabolic pathway to the aminoacylation of tRNA by alanine. 4-aminobutyrate pyruvate transaminase catalyzes the following reaction: GABA+pyruvate→L-alanine+succinate semialdehyde. Alanyl-tRNA synthetase is then used to catalyze the aminoacylation of tRNA by L-alanine, resulting in the release of AMP (Ala+ATP+tRNA→Ala-tRNA+AMP+PPi). To monitor glutamate decarboxylase activity, the glutamate decarboxylase reaction (L-Glu→GABA+$CO_2$) is coupled to the subsequent conversion of GABA to L-Ala, which is then used to aminoacylate tRNA as described above. The activity of a particular enzyme in the pathway (e.g., glutamate decarboxylase, 4-aminobutyrate pyruvate deaminase) can be monitored by decreasing the concentration of the enzyme such that the step that it catalyzes is rate-limiting in the assay. This will result in the rate of the reaction being entirely dependent on the activity of that (rate-limiting) enzyme. The assay sensitivity can be increased and cost decreased by recycling the L-Ala-tRNA product. Since the GABA metabolic pathway generates L-alanine, MurM is used to recycle the L-Ala-tRNA product without releasing free L-Ala (see FIGS. 40-42).

Figure 57:
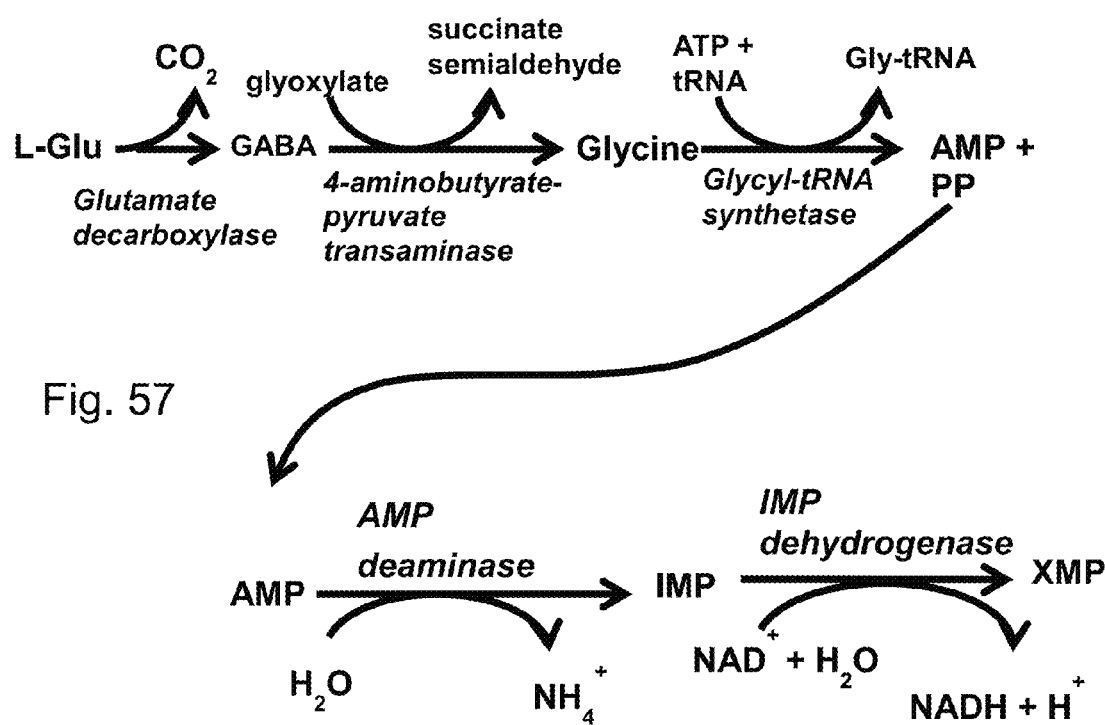
FIG. 57 is a reaction scheme for monitoring the activity of the enzymes in the GABA metabolic pathway by coupling it to the production of NADH via glycyl-tRNA synthetase and the AMP assay. An analogous reaction scheme can be drawn in which the activity of the enzymes in the GABA metabolic pathway are coupled the production of light by bacterial luciferase (i.e. by coupling the production of NADH to the bacterial luciferase catalyzed oxidation of a low molecular weight aldehyde, as described above).

Turning next to FIG. 57, and described above, the inventors disclose a method to monitor the activity of the enzymes involved in the synthesis and breakdown of 4-aminobutyrate (GABA) by coupling the GABA metabolic pathway to the aminoacylation of tRNA by glycine. This process is analogous to that shown with FIG. 52, except that 4-aminobutyrate pyruvate transaminase catalyzes the following reaction: GABA+glyoxylate→Glycine+succinate semialdehyde. Glycyl-tRNA synthetase is then used to catalyze the aminoacylation of tRNA by glycine, resulting in the release of AMP (Gly+ATP+tRNA→Gly-tRNA+AMP+PPi). To monitor glutamate decarboxylase activity, the glutamate decarboxylase reaction (L-Glu→GABA+$CO_2$) is coupled to the subsequent conversion of GABA to Gly, which is then used to aminoacylate tRNA as described above. The activity of a particular enzyme in the pathway (i.e., glutamate decarboxylase, 4-aminobutyrate pyruvate deaminase) can be monitored by decreasing the concentration of the enzyme such that the step that it catalyzes is rate-limiting in the assay. This will result in the rate of the reaction being entirely dependent on the activity of that (rate-limiting) enzyme.

Figure 58:
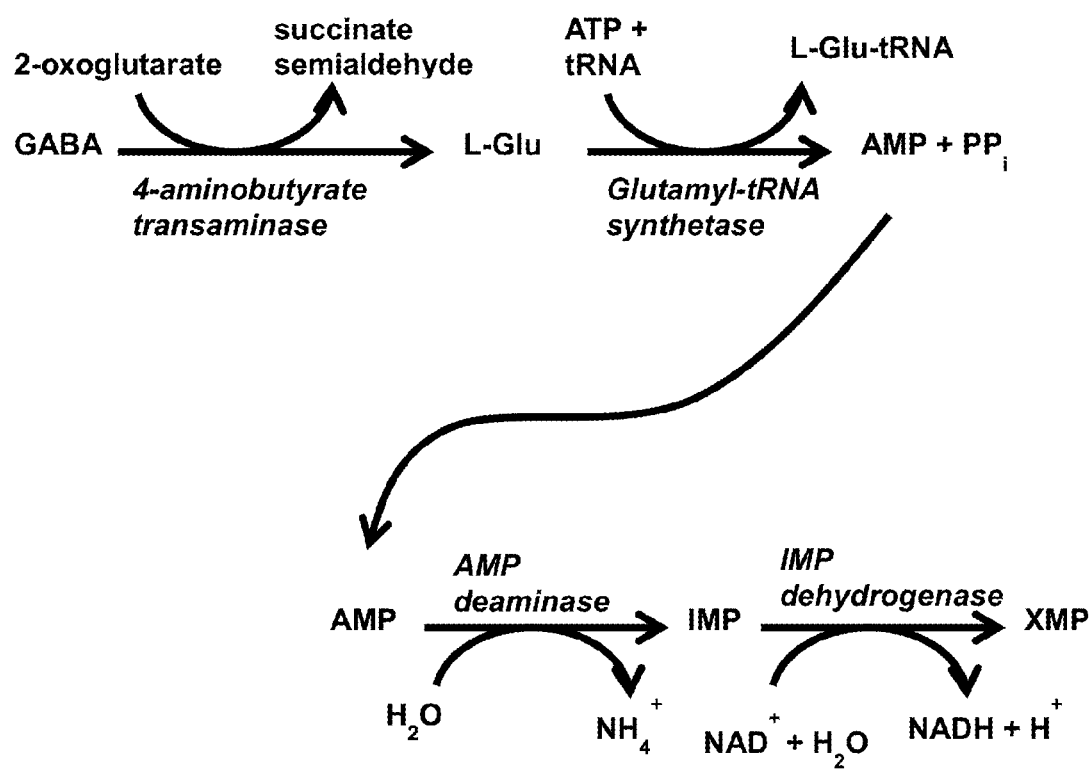
FIG. 58 is a reaction scheme for monitoring the activity of the enzymes in the GABA degradation pathway by coupling it to the production of NADH via glutamyl-tRNA synthetase and the AMP assay. An analogous reaction scheme can be drawn in which the activity of the enzymes in the GABA metabolic pathway are coupled the production of light by bacterial luciferase (i.e. by coupling the production of NADH to the bacterial luciferase catalyzed oxidation of a low molecular weight aldehyde, as described above)

Turning next to FIGS. 58 and 58, and described above, the inventors disclose a method to monitor the activity of 4-aminobutyrate transaminase, which catalyzes the conversion of 4-aminobutyrate (GABA) to L-glutamic acid by coupling this GABA metabolic pathway to the aminoacylation of tRNA by glutamate 4-aminobutyrate transaminase catalyzes the conversion of GABA+2-oxoglutarate to L-glutamate+succinated semialdehyde. The activity of 4-aminobutyrate transaminase is monitored by following the production of L-glutamate. This is done by using glutamyl-tRNA synthetase to catalyze the aminoacylation of tRNA by L-glutamate, releasing AMP as a product (L-Glu+ATP+tRNA→L-Glu-tRNA+AMP+$PP_i$).

Since the GABA degradation pathway is coupled to the glutamyl-tRNA synthetase assay through the production of L-glutamate, the L-Glu-tRNA product must be recycled without regenerating the L-Glu substrate. This can be achieved by: (1) using a nondiscriminating glutaminyl-tRNA synthetase to synthesize L-Glu-tRNA$^{Gln}$, (2) using a Gln- or Asn-dependent transamidases (e.g. GatCAB) to convert L-Glu-tRNA$^{Gln}$ to L-Gln-tRNA$^{Gln}$, and (3) hydrolyzing the L-Gln-tRNA$^{Gln}$ product with, for example, the M129K variant of D-tyrosyl-tRNA deacylase. In this approach, the concentration of the Gln- or Asn-dependent transamidase must be sufficiently high that the L-Glu-tRNA$^{Gln}$ product is converted to L-Gln-tRNA$^{Gln}$ before it gets hydrolyzed.

Continuing, and described above, the inventors disclose a general method to screen for inhibitors of any enzyme that can be coupled to the production of AMP, including aminoacyl-tRNA synthetases, DNA ligases, ubiqutin and ubiquitin-like ligases, cAMP phosphodiesterases, polyA deadenylases, and ribonucleases. See FIG. 31. To screen for inhibitors, the assay is designed such that the concentration of the targeted enzyme is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on the targeted enzyme include varying the concentration of the targeted enzyme in the assay and monitoring the effect that this has on inhibition of the assay.

Continuing, and described above, the inventors disclose a general method to screen for inhibitors of an enzyme in a pathway that can be coupled to the production of AMP. See FIG. 32. To screen for inhibitors, the assay is designed such that the concentration of the targeted enzyme is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on the targeted enzyme include varying the concentration of the targeted enzyme in the assay and monitoring the effect that this has on inhibition of the assay.

Continuing, and described above, the inventors disclose a method to screen for inhibitors of tyrosyl-tRNA synthetase. See FIGS. 33-37. To screen for inhibitors, the assay is designed such that the concentration of tyrosyl-tRNA synthetase is sufficiently low that the reaction it catalyzes is rate-limiting. Inhibitors identified by this initial screen are subjected to a subsequent secondary screen in which tyrosyl-tRNA synthetase is not present in the assay mix to verify that the inhibitor is acting on tyrosyl-tRNA synthetase. Alternative means of verifying that the inhibitor is acting on tyrosyl-tRNA synthetase include varying the tyrosyl-tRNA synthetase concentration in the assay and monitoring the effect that this has on inhibition of the assay, replacing cycloditryosine synthetase with D-tyrosyl-tRNA deacylase and monitoring the effect of the inhibitor on the aminoacylation of tRNA by D-tyrosine, and replacing cycloditryosine synthetase with the M129K variant of D-tyrosyl-tRNA deacylase and monitoring the effect that the inhibitor has on the aminoacylation of tRNA by L-tyrosine.

Continuing, and described above, the inventors disclose a method to screen for inhibitors of an aminoacyl-tRNA synthetase. See FIGS. 43-46. To screen for inhibitors, the assay is designed such that the concentration of the targeted enzyme is sufficiently low that the reaction it catalyzes is rate-limiting. Inhibitors identified by this initial screen are subjected to a subsequent secondary screen in which the aminoacyl-tRNA synthetase is not present in the assay mix to verify that the inhibitor is acting on the aminoacyl-tRNA synthetase. Alternative means of verifying that the inhibitor is acting on the aminoacyl-tRNA synthetase include varying the aminoacyl-tRNA synthetase concentration in the assay and monitoring the effect that this has on inhibition of the assay.

Continuing, and described above, the inventors disclose a method to screen for inhibitors of D-tyrosyl-tRNA deacylase. See FIGS. 38-40. To screen for inhibitors, the assay is designed such that the concentration of the D-tyrosyl-tRNA deacylase is sufficiently low that the reaction it catalyzes is rate-limiting. Inhibitors identified by this initial screen are subjected to a subsequent secondary screen in which D-tyrosyl-tRNA deacylase is not present in the assay mix to verify that the inhibitor is acting on the targeted enzyme. Alternative means of verifying that the inhibitor is acting on D-tyrosyl-tRNA deacylase include varying the concentration of D-tyrosyl-tRNA deacylase in the assay and monitoring the effect that this has on inhibition of the assay; another alternative is to replace D-tyrosyl-tRNA deacylase with the cyclodityrosine synthetase and monitor the effect this has on the inhibition of the tRNA aminoacylation reaction.

Continuing, and described above, the inventors disclose a method to screen for inhibitors of cyclodityrosine synthetase and other members of the cyclodipeptide synthase family. See FIGS. 35-37. To screen for inhibitors, the assay is designed such that the concentration of the cyclodityrosine synthetase/cyclodipeptide synthase is sufficiently low that the reaction it catalyzes is rate-limiting. Inhibitors identified by this initial screen are subjected to a subsequent secondary screen in which cyclodityrosine synthetase/cyclodipeptide synthase is not present in the assay mix to verify that the inhibitor is acting on the targeted enzyme. Alternative means of verifying that the inhibitor is acting on the targeted enzyme include varying the concentration of cyclodityrosine synthetase/cyclodipeptide synthase in the assay and monitoring the effect that this has on inhibition of the assay; alternatively, cyclodityrosine synthetase/cyclodipeptide synthase can be replaced with the M129K variant of D-tyrosyl-tRNA deacylase, monitoring the effect of the inhibitor on the aminoacylation of tRNA and comparing it to the effect that the inhibitor has when cyclodityrosine synthetase/cyclodipeptide synthase is present.

Continuing, and described above, the inventors disclose a method to screen for inhibitors of *Streptococcus pneumonia* MurM. See FIG. 46. MurM is an aminoacyl-tRNA ligase that transfers the aminoacyl moieties from L-Ser-tRNA and L-Ala-tRNA to the stem peptide lysine in Lipid II in the cell wall proteoglycan of *Streptococcus pneumoniae*. MurM is essential for clinically observed penicillin resistance in *Streptococcus pneumoniae*. Inhibitors of MurM could lead to drugs that disrupt the resistance of *Streptococcus pneumonia* to penicillin. To screen for inhibitors, the assay is designed such that the concentration of the MurM is sufficiently low that the reaction it catalyzes is rate-limiting. Inhibitors identified by this initial screen are subjected to a subsequent secondary screen in which MurM is not present in the assay mix to verify that the inhibitor is acting on the targeted enzyme. Alternative means of verifying that the inhibitor is acting on the targeted enzyme include varying the concentration of MurM in the assay and monitoring the effect that this has on inhibition of the assay; alternatively, MurM can be replaced with the M129K variant of D-tyrosyl-tRNA deacylase, AlaX, or a similar L-Ala-tRNA editing protein, and the effect of the inhibitor on the aminoacylation of tRNA by L-Ala can be monitored and compared to the effect that the inhibitor has when MurM is present.

Continuing, and described above, the inventors disclose a method to screen for inhibitors of Gln- and Asn-dependent transamidases (e.g. GatCAB, GatDE). See FIG. 47. To screen for inhibitors, the assay is designed such that the concentration of the Gln- or Asn-dependent transamidase is sufficiently low that the reaction it catalyzes is rate-limiting. Inhibitors identified by this initial screen are subjected to a subsequent secondary screen in which Gln- or Asn-dependent transamidase is not present in the assay mix to verify that the inhibitor is acting on the targeted enzyme. Alternative means of verifying that the inhibitor is acting on the targeted enzyme include varying the concentration of Gln- or Asn-dependent transamidase in the assay and monitoring the effect that this has on inhibition of the assay; alternatively, Gln- or Asn-dependent transamidase can be replaced with the M129K variant of D-tyrosyl-tRNA deacylase, and the effect that the inhibitor has on the aminoacylation of tRNA by L-Glu can be and compared to the effect that the inhibitor has when Gln- or Asn-dependent transamidase is present.

Continuing, and described above, the inventors disclose a method to screen for inhibitors of pre-transfer editing by aminoacyl-tRNA synthetases. See FIGS. 48 and 49. To screen for inhibitors, the assay is designed such that the concentration of the aminoacyl-tRNA synthetase) is sufficiently low that pre-transfer editing is the rate-limiting step. Inhibitors identified by this initial screen are subjected to a subsequent secondary screen in which the aminoacyl-tRNA synthetase is not present in the assay mix to verify that the inhibitor is acting on the targeted enzyme and not another enzyme in the assay mix.

Figure 51:
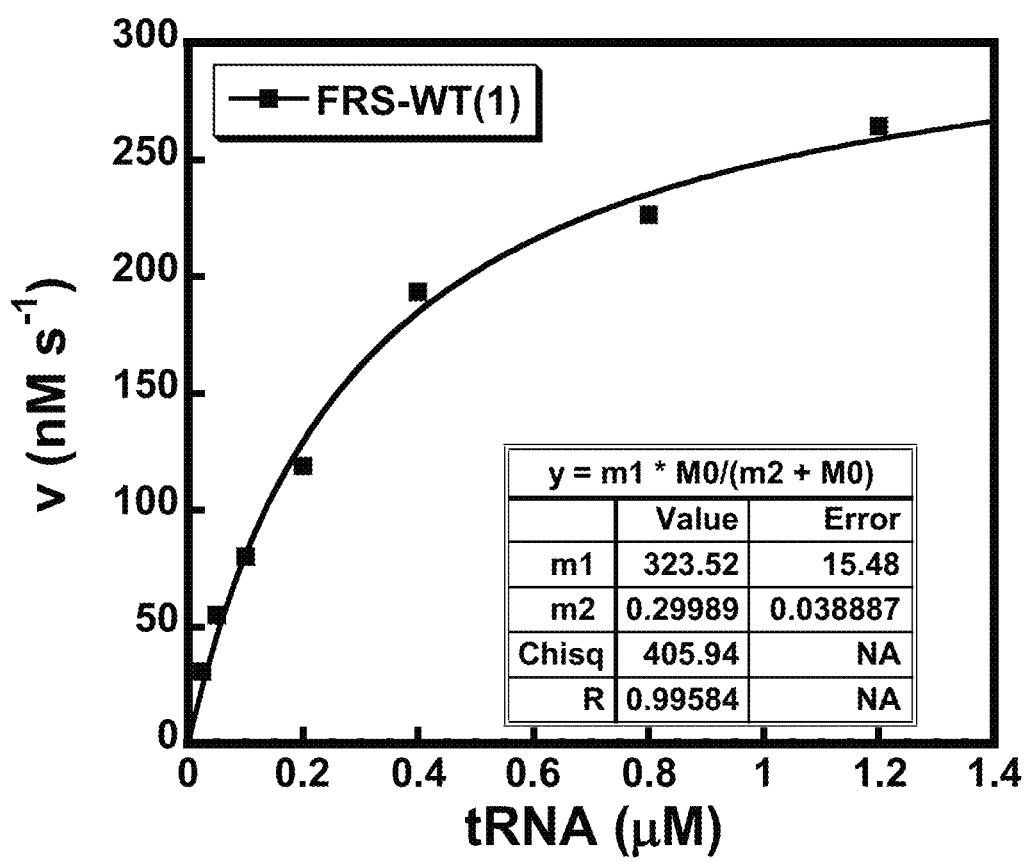
FIG. 51 is an assay for post-transfer editing of Tyr-tRNAPhe by wild-type *Saccharomyces cerevisiae* phenylalanyl-tRNA synthetase. The editing activity of wild type phenylalanyl-tRNA synthetase was monitored by using an editing-deficient variant of phenylalanyl-tRNA synthetase (D243A) to generate Tyr-tRNAPhe. In the absence of the wild-type enzyme, the all of the tRNAPhe becomes aminoacylated with tyrosine and no additional AMP is generated. The subsequent addition of wild type phenylalanyl-tRNA synthetase results in hydrolysis of the Tyr-tRNAPhe, allowing the aminoacylation reaction (and the release of AMP) to proceed. Since the conditions are adjusted to make the editing activity of the wild-type phenylalanyl-tRNA synthetase rate-limiting, the $V_{max}$ and $K_m$ values determined in the assay are for the editing of Tyr-tRNAPhe by the wild type enzyme. The concentrations of L-tyrosine and ATP in the assay are 1 mM and 2 mM, respectively. The concentrations of the wild-type and D243A variants of phenylalanyl-tRNA synthetase are 0.05 µM and 0.25 µM, respectively. The concentration of tRNA was varied from 0-1.2 µM. The rate of the post-transfer editing reaction was monitored by following the change in absorbance at 340 nm due to the production of NADH, as described above with the assay for monitoring aminoacyl-tRNA synthetase activity. Data were fit to the Michaelis-Menten equation to determine $V_{max}$ and $K_m$ values for the post-transfer editing reaction (m1 and m2, respectively).

Continuing, and described above, the inventors disclose a method to screen for inhibitors of post-transfer editing by aminoacyl-tRNA synthetases and other aminoacyl-tRNA editing proteins. See FIGS. 50 and 51. To screen for inhibitors, the assay is designed such that the concentration of the aminoacyl-tRNA synthetase containing the functional editing domain (or the editing protein) is sufficiently low that post-translational editing is the rate-limiting step. Inhibitors identified by this initial screen are subjected to a subsequent secondary screen in which the aminoacyl-tRNA synthetase is not present in the assay mix to verify that the inhibitor is acting on the targeted enzyme and not another enzyme in the assay mix. Alternatively, the aminoacyl-tRNA synthetase containing the editing domain can be replaced by the M129K variant of D-tyrosyl-tRNA deacylase (which hydrolyzes L-aminoacyl-tRNAs) and the effect that the inhibitor has on this assay can be compared to the effect that it has when the aminoacyl-tRNA synthetase containing the functional editing domain (or the editing protein) is present.

Continuing, and described above, the inventors disclose a general method to screen for inhibitors of an enzyme in a pathway that can be coupled to the aminoacylation of tRNA. See FIG. 32. To screen for inhibitors, the assay is designed such that the concentration of the targeted enzyme is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on the targeted enzyme include varying the concentration of the targeted enzyme in the assay and monitoring the effect that this has on inhibition of the assay.

Continuing, and described above, the inventors disclose a method to screen for inhibitors of ubiquitin- and ubiquitin-like ligases. See FIG. 52. To screen for inhibitors, the assay is designed such that the concentration of the targeted enzyme is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on the targeted enzyme include varying the concentration of the targeted enzyme in the assay and monitoring the effect that this has on inhibition of the assay.

Continuing, and described above, the inventors disclose a method to screen for inhibitors of tyrosine hydroxylase. See FIG. 53. To screen for inhibitors, the assay is designed such that the concentration of tyrosine hydroxylase is sufficiently low that the reaction it catalyzes is rate-limiting. Inhibitors identified by this initial screen are subjected to a subsequent secondary screen in which tyrosine hydroxylase is not present in the assay mix to verify that the inhibitor is acting on tyrosine hydroxylase. Alternative means of verifying that the inhibitor is acting on tyrosine hydroxylase include varying its concentration in the assay and monitoring the effect that this has on inhibition of the assay.

Continuing, and described above, the inventors disclose a method to screen for inhibitors of every enzyme in the dopamine-norepinephrine-epinephrine biosynthetic pathway by coupling the production of epinephrine to the aminoacylation of tRNA by methionine. See FIG. 54. To screen for inhibitors of the enzymes in the dopamine-norepinephrine-epinephrine biosynthetic pathway, the assay is designed such that the concentration of the targeted enzyme is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on targeted enzyme include varying the concentration of the enzyme in the assay and monitoring the effect that this has on inhibition of the assay. Alternatively, every enzyme in the pathway can be screened simultaneously by ensuring that the concentrations of the enzymes are adjusted such that the rate of each step in the pathway is approximately equal. Inhibitors identified by this initial screen are subjected to subsequent secondary screens in which one or more of the enzymes in the assay is not present in the assay mix to determine which enzyme the inhibitor is acting on. Alternatively, the concentrations of each enzyme in the pathway can be varied in the assay to determine which enzyme is affected by the inhibitor.

Continuing, and described above, the inventors disclose a method to screen for inhibitors of the enzymes involved in the synthesis and breakdown of 4-aminobutyrate (GABA) by coupling the GABA metabolic pathway to the aminoacylation of tRNA by alanine. See FIGS. 55 and 56. To screen for inhibitors of the enzymes in the GABA metabolic pathway, the assay is designed such that the concentration of the targeted enzyme (i.e., either glutamate decarboxylase or 4-aminobutyreate pyruvate transaminase) is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on targeted enzyme include varying the concentration of the targeted enzyme in the assay and monitoring the effect that this has on inhibition of the assay. Alternatively, every enzyme in the pathway can be screened simultaneously by ensuring that the concentrations of the enzymes are adjusted such that the rate of each step in the pathway is approximately equal. Inhibitors identified by this initial screen are subjected to subsequent secondary screens in which one or more of the enzymes in the assay is not present in the assay mix to determine which enzyme the inhibitor is acting on. Another alternative is to vary the concentration of each enzyme in the pathway to determine which enzyme is affected by the inhibitor.

Continuing, and described above, the inventors disclose a method to screen for inhibitors of the enzymes involved in the synthesis and breakdown of 4-aminobutyrate (GABA) by coupling the GABA metabolic pathway to the aminoacylation of tRNA by glycine. See FIG. 57. To screen for inhibitors of the enzymes in the GABA metabolic pathway, the assay is designed such that the concentration of the targeted enzyme (i.e., either glutamate decarboxylase or 4-aminobutyreate pyruvate transaminase) is sufficiently low that the reaction it catalyzes is rate-limiting. Inhibitors identified by this initial screen are subjected to a subsequent secondary screen in which the targeted enzyme is not present in the assay mix to verify that the inhibitor is acting on the targeted enzyme. Alternative means of verifying that the inhibitor is acting on targeted enzyme include varying the concentration of the targeted enzyme in the assay and monitoring the effect that this has on inhibition of the assay. Alternatively, every enzyme in the pathway can be screened simultaneously by ensuring that the concentrations of the enzymes are adjusted such that the rate of each step in the pathway is approximately equal. Inhibitors identified by this initial screen are subjected to subsequent secondary screens in which one or more of the enzymes in the assay is not present in the assay mix to determine which enzyme the inhibitor is acting on. Another alternative is to vary the concentration of each enzyme in the pathway to determine which enzyme is affected by the inhibitor.

Figure 59:
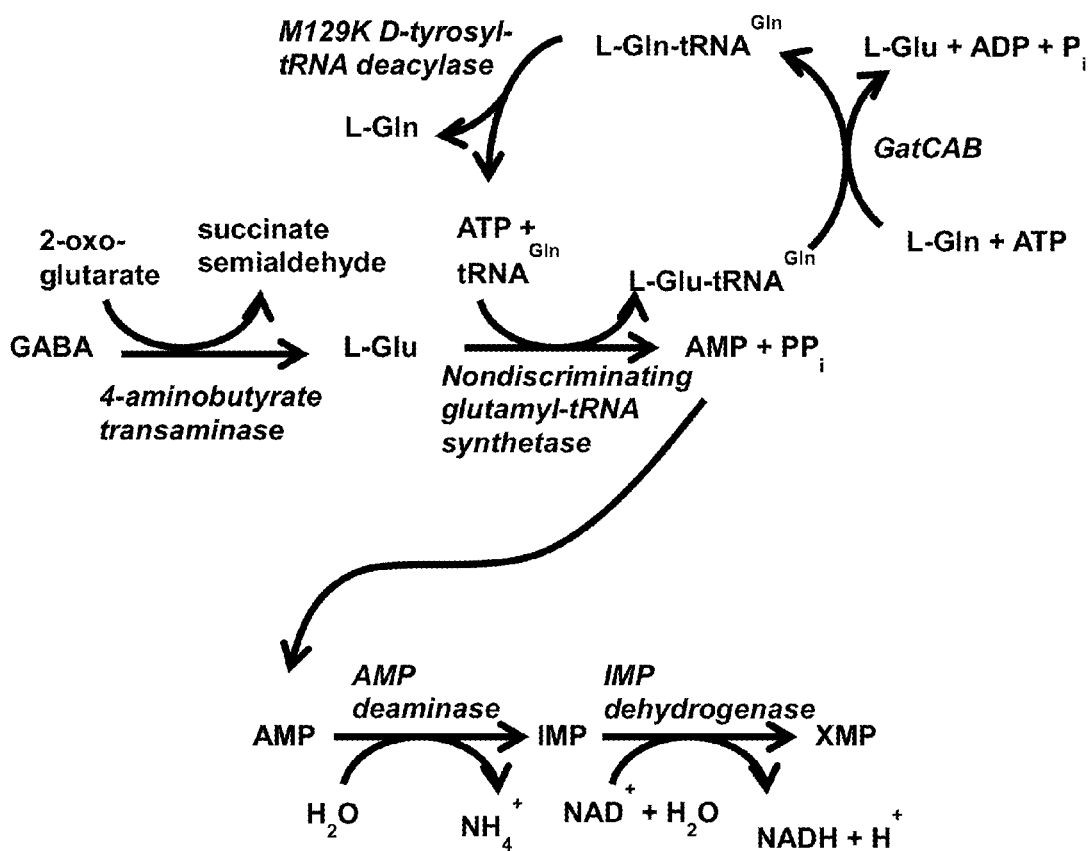
FIG. 59 is a reaction scheme for monitoring the activity of the enzymes in the GABA degradation pathway in which the L-Glu-tRNA product is recycled. An analogous reaction scheme can be drawn in which the activity of the enzymes in the GABA metabolic pathway are coupled the production of light by bacterial luciferase (i.e. by coupling the production of NADH to the bacterial luciferase catalyzed oxidation of a low molecular weight aldehyde, as described above).

Continuing, and described above, the inventors disclose a method to screen for inhibitors of 4-aminobutyrate (GABA) transaminase by coupling the conversion of GABA to L-glutamate to the aminoacylation of tRNA by L-glutamate. See FIGS. 58 and 59. To screen for inhibitors of 4-aminobutyrate transaminase, the assay is designed such that the concentration of 4-aminobutyrate transaminase is sufficiently low that the reaction it catalyzes is rate-limiting. Inhibitors identified by this initial screen are subjected to a subsequent secondary screen in which the 4-aminobutyrate transaminase is not present in the assay mix to verify that the inhibitor is acting on the targeted enzyme. Alternative means of verifying that the inhibitor is acting on 4-aminobutyrate transaminase include varying the concentration of 4-aminobutyrate transaminase in the assay and monitoring the effect that this has on inhibition of the assay.

Some of the abbreviations used are as follows: adenosine 5'-monophosphate (AMP), inosine 5'-monophosphate (IMP), xanthine 5'-monophosphate (XMP), adenosine 5'-triphosphate (ATP), pyrophosphate ($PP_i$), oxidized and reduced nicotine adenine dinucleotide ($NAD^+$ and NADH, respectively), cyclic AMP (cAMP), tris(hydroxymethyl)aminomethane (TRIS), phosphodiesterase (PDE), small ubiquitin-like modifier (SUMO), *Escherichia coli*(*E. coli*), *Saccharomyces cerevisiae* (*S. cerevisiae*), γ-aminobutyric acid (GABA), tris(hydroxymethyl)aminomethane (TRIS), cyclodityrosine synthase (CDYS), D-tyrosyl-tRNA deacylase (DTD), cytochrome P450 CYP121 (CYP121), amino acid (AA), L-tyrosine (L-Tyr), D-tyrosine (D-Tyr), aminoacyl-tRNA synthetase (aaRS), tyrosyl-tRNA synthetase (TyrRS), covalent bond ("—"), noncovalent bond ("•"), polymerase chain reaction (PCR), *Mycobacterium tuberculosis* (*M. tuberculosis*), and *Thermus thermophilus* (*T. thermophilus*).

While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:

1. A method of conducting an enzymatic reaction assay that result in adenosine 5'-monophosphate (AMP) production, comprising the steps of:
   reacting one or more compounds that producing AMP;
   deaminating the AMP using AMP deaminase to produce IMP; and
   oxidizing the IMP in the presence of IMP dehydrogenase and NAD+ to produce XMP and NADH.

2. The method of claim 1 further comprising the step of monitoring an absorbance of the assay at 340 nm.

3. The method of claim 1 further comprising the step of coupling a production of the NADH to a bacterial luciferase catalyzed oxidation of a low molecular weight aldehyde.

4. The method of claim 1 further comprising the step of monitoring an activity of the one or more enzymes coupled to the production of the AMP.

5. The method of claim 1 wherein the reaction involves one or more of aminoacyl-tRNA synthetases, DNA ligases, ubiqutin and ubiquitin-like ligases, cAMP phosphodiesterases, polyA deadenylases, and ribonucleases.

6. The method of claim 1 further comprising the step of aminoacylation of a tRNA by an amino acid.

7. The method of claim 6 further comprising the step of substantially continuously recycling the tRNA.

8. The method of claim 7 further comprising the steps of recycling the tRNA using one of an editing domain, an editing protein, an editing protein containing an editing domain, cyclodipeptide synthases, and aminoacyl-tRNA using enzymes, such as Penicillin Resistance Factor MurM and FEM ligases.

9. The method of claim 7 further comprising the step of one of removing and converting the amino acid from the assay after hydrolysis of an aminoacyl-tRNA product.

10. The method of claim 6 further comprising the step of monitoring one of a pre-transfer editing activity of a aminoacyl-tRNA synthetase, a post-transfer editing activity of the aminoacyl-tRNA synthetase, and a post transfer editing activity of an aminoacyl-tRNA editing protein.

11. The method of claim 6 further comprising monitoring an activity of an enzyme in a pathway coupled to the aminoacylation of the tRNA.

12. The method of claim 1 further comprising the step of continuously recycling an ubiquitin substrate using deubiquitinating enzymes.

13. The method of claim 6 further comprising the step of monitoring one of tyrosine hydroxylase by coupling tyrosine hydroxylase to the aminoacylation of the tRNA by L-DOPA.

14. The method of claim 6 further comprising the step of monitoring the activity of one or more enzymes in a dopamine-norepinephrine-epinephrine biosynthetic pathway.

15. The method of claim 6 further comprising the step of monitoring an activity of an enzyme involved in a synthesis and breakdown of 4-aminobutyrate (GABA).

16. The method of claim 1 further comprising the step of screening for inhibitors of one or more enzymes that may be coupled to the production of the AMP.

17. The method of claim 6 further comprising the step of screening for inhibitors of enzymes that may be coupled to the aminoacylation of the tRNA.

18. A kit, containing
   a compound of claim 1; and
   an assay buffer.

* * * * *